(12) United States Patent
Laezza et al.

(10) Patent No.: US 10,889,543 B2
(45) Date of Patent: Jan. 12, 2021

(54) FINE-TUNE MODULATORS OF NEURONAL EXCITABILITY FOR NEUROPSYCHIATRIC DISORDERS

(71) Applicant: THE BOARD OF REGENTS OF THE UNIVERSITY OF TEXAS SYSTEM, Austin, TX (US)

(72) Inventors: Fernanda Laezza, Galveston, TX (US); Jia Zhou, Galveston, TX (US); Zhiqing Liu, Galveston, TX (US); Syed Ali, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/461,793

(22) PCT Filed: Nov. 20, 2017

(86) PCT No.: PCT/US2017/062566
§ 371 (c)(1),
(2) Date: May 16, 2019

(87) PCT Pub. No.: WO2018/094335
PCT Pub. Date: May 24, 2018

(65) Prior Publication Data
US 2019/0270705 A1    Sep. 5, 2019

Related U.S. Application Data

(60) Provisional application No. 62/424,488, filed on Nov. 20, 2016.

(51) Int. Cl.
*C07D 207/16*     (2006.01)
*C07C 237/52*     (2006.01)
(Continued)

(52) U.S. Cl.
CPC .......... *C07D 207/16* (2013.01); *A61K 31/401* (2013.01); *A61K 31/427* (2013.01);
(Continued)

(58) Field of Classification Search
CPC .................................................. C07D 207/16
See application file for complete search history.

(56) References Cited

U.S. PATENT DOCUMENTS

2006/0003391 A1*  1/2006  Ring ................ G01N 33/57423
                                                                            435/7.23

* cited by examiner

*Primary Examiner* — Shawquia Jackson
(74) *Attorney, Agent, or Firm* — Hylton-Rodic Law PLLC

(57) ABSTRACT

The present invention relates to novel small molecule modulators of Nav1.6 channels of the general formulae (I), (II), (III) and (IV), and the uses thereof.

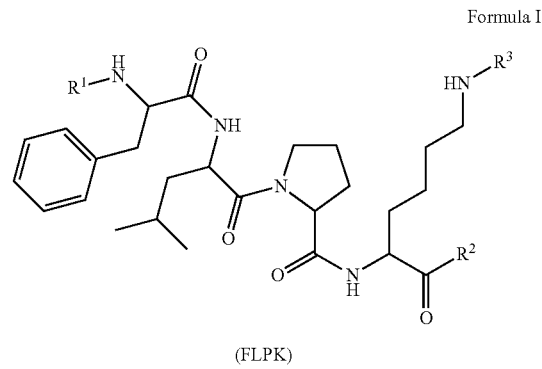

(FLPK)    Formula I

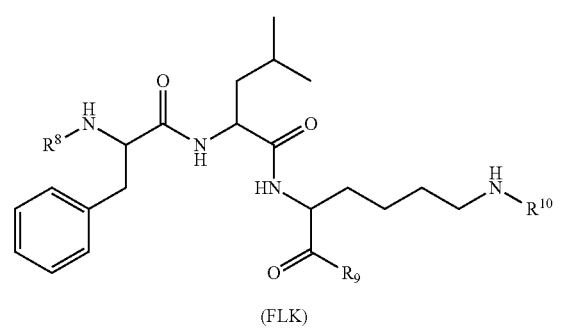
(FLK)    Formula II

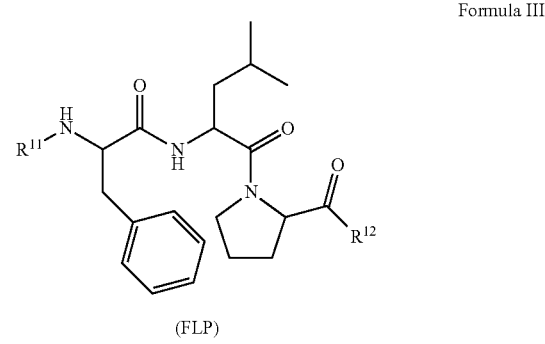
(FLP)    Formula III

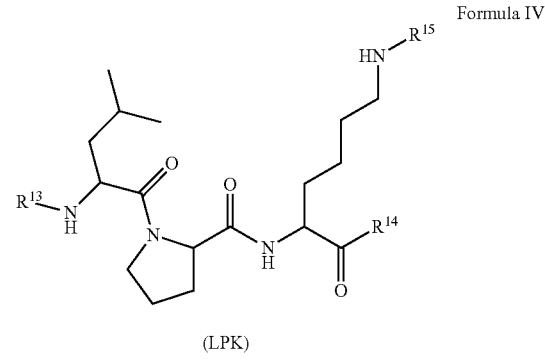
(LPK)    Formula IV

16 Claims, 24 Drawing Sheets

(51) Int. Cl.
*C07D 413/12* (2006.01)
*C07D 417/12* (2006.01)
*A61K 31/5377* (2006.01)
*A61K 38/18* (2006.01)
*C07K 5/087* (2006.01)
*A61K 31/401* (2006.01)
*C07K 5/107* (2006.01)
*A61K 45/06* (2006.01)
*C07K 5/083* (2006.01)
*A61K 31/427* (2006.01)

(52) U.S. Cl.
CPC ...... *A61K 31/5377* (2013.01); *A61K 38/1825* (2013.01); *A61K 45/06* (2013.01); *C07C 237/52* (2013.01); *C07D 413/12* (2013.01); *C07D 417/12* (2013.01); *C07K 5/0808* (2013.01); *C07K 5/0812* (2013.01); *C07K 5/1016* (2013.01)

I

J

FINE-TUNE MODULATORS OF NEURONAL EXCITABILITY FOR NEUROPSYCHIATRIC DISORDERS

CROSS REFERENCE TO RELATED APPLICATIONS

This application is a U.S. national stage application of International Application No. PCT/US2017/062566, filed Nov. 20, 2017, which claims the benefit of the filing date of U.S. Application 62/424,488, filed Nov. 20, 2016, the contents of which are hereby incorporated by reference in their entirety.

STATEMENT OF FEDERALLY SPONSORED RESEARCH AND DEVELOPMENT

This invention was made with government support under NIH/NIMH Grant No. R01 MH095995-A1 and MH111107 awarded by the National Institutes of Health (NIH) and National Institute of Mental Health (NIMH). The government has certain rights in the invention.

FIELD OF THE INVENTION

The field of the invention relates generally to small molecule modulators of Nav1.6 channel.

BACKGROUND

This background information is provided for the purpose of making information believed by the applicant to be of possible relevance to the present invention. No admission is necessarily intended, nor should it be construed, that any of the information disclosed herein constitutes prior art against the present invention.

Psychiatric diseases and addictive behaviors are neural circuitry disorders that lead to dysfunction of high-order psychological domains. As indicated by the NIMH and NIDA, these diseases are in great need of targeted therapeutic remedies.

The pore-forming α-subunit of the voltage-gated Na+ (Nav) channels (Nav1.1-Nav1.9) provides the basis for neuronal electrical excitability in the brain. These channels are regulated by a number of brain-specific accessory proteins. One of the critical accessory proteins is fibroblast growth factor 14 (FGF14), a member of the intracellular FGFs (iFGFs; FGF11-13) associated with several brain disorders. FGF14 binds directly to the C-tail of Nav channel and regulates neuronal excitability by controlling the channel expression and gating properties.

FGF14 is a physiologically relevant accessory protein of Nav channels that has been associated with neurological disorders such as ataxia, schizophrenia, and depression. See e.g., van Swieten J. C., et al., American journal of human genetics 72:191-199 (2003); Rodriguez-Murillo, L., et al., Neuropsychopharmacology: official publication of the American College of Neuropsychopharmacology 39:934-943 (2014); Verbeek, E. C., et al., PLoS ONE 7(5):e37384 (2012); Rush, A. M., et al. The European journal of neuroscience 23:2551-2562 (2006). Furthermore, FGF14 is a functionally relevant component of the axonal initial segment (AIS). Through isoform-specific interactions with the intracellular C-terminal tail of neuronal Nav channels (Nav1.1, Nav1.2, Nav1.6), FGF14 controls channel gating and axonal targeting in neurons. In translational studies, interest in FGF14 continues to rise with a growing list of associative links to diseases of the cognitive and affective domains such as neurodegeneration, depression, anxiety, addictive behaviors [1-5] and recently schizophrenia[6]. See e.g., E. Brusse, I., et al., *Spinocerebellar ataxia associated with a mutation in the fibroblast growth factor 14 gene (SCA27): A new phenotype*, Mov Disord, 21: 396-401 (2006); Laezza, F., et al., Role of the axonal initial segment in psychiatric disorders: function, dysfunction, and intervention, Frontiers in psychiatry, 5:109 (2014); Laezza, F., et al., Genetic deletion of fibroblast growth factor 14 recapitulates phenotypic alterations underlying cognitive impairment associated with schizophrenia, Translational Psychiatry (2016), in press.

Numerous Genome-Wide-Association Studies (GWAS) have reported Single nucleotide polymorphisms (SNPs) in FGF14 in the context of neuropsychiatric disorders (Di Re J., Laezza F. Intracellular fibroblast growth factor 14: emerging risk factor for neuropsychiatric disorders, Front Cell Neurosci, 2017). Although all these SNPs are in the FGF14 intronic region and thus their role on the protein expression and function are unclear, they might provide guidance for future investigations. A Brazilian pilot study on early onset/familial schizophrenia found a link between early-onset schizophrenia and FGF14. See e.g., Gadelha A., et al., Linkage replication for chromosomal region 13q32 in schizophrenia: evidence from a Brazilian pilot study on early onset schizophrenia families. PLoS One. 7:e52262 (2012). GWAS in German cohort found an association between FGF14 and schizophrenia, which is corroborated by a linkage study of familial schizophrenia in Canadian families of Celtic or German descent. See e.g., Brzustowicz L. M., et al., Linkage of familial schizophrenia to chromosome 13q32. Am. J. Hum. Genet. 1999; 65(4):1096-103. Additionally, SNPs in FGF14 have been associated with dependence on alcohol and illegal substances in humans, and a fine-mapping study found several SNPs to be associated with major depressive disorder in a study of Dutch twins. See e.g., Drgon T., et al., "Replicated" genome wide association for dependence on illegal substances: genomic regions identified by overlapping clusters of nominally positive SNPs. Am J Med Genet B Neuropsychiatr Genet. 156:125-38 (2011). Furthermore, an FGF14 SNP is associated with volumetric changes in the entorhinal cortex in AD patients. See e.g., Yang T., et al., Detecting genetic risk factors for alzheimer's disease in whole genome sequence data via lasso screening. Proc. IEEE Int. Symp. Biomed. Imaging 985-989 (2015).

Furthermore, voltage-gated sodium (Nav) channels interact with auxiliary proteins, including intracellular fibroblast growth factor 13 (FGF13), which modulate their biophysical properties in different regions within the CNS and PNS. FGF13 has been associated with epilepsy in humans and in preclinical models and in preclinical models of neuroinflammatory pain. See e.g., Puranam, R. S., et al., Disruption of Fgf13 causes synaptic excitatory-inhibitory imbalance and genetic epilepsy and febrile seizures plus. J Neurosci. 35:8866-81 (2015). These protein-protein interactions (PPI) are necessary to maintain neuronal excitability, and FGF13 dysfunction is associated with epilepsy and neuropathic pain.

It has been found that voltage-gated sodium (Nav) channels are transmembrane proteins that facilitate the influx of sodium ions ($I_{Na}$ current) in excitable cells, and thus they are involved in the initiation and propagation of action potentials. See e.g., Hodgkin A. L. & Huxley A. F., The Journal of physiology 117:500-544 (1952). Furthermore, Nav channels are composed of a pore-forming α-subunit (220-260 kDa) and an auxiliary β-subunits (32-36 KDa). See e.g., Catterall, W. A., Neuron 26:13-25 (2000). To date, nine isoforms of Nav channels (Nav1.1-Nav1.9) have been functionally characterized and a tenth (Nax) has been identified. See e.g., Yu, F. H. & Catterall, W. A., Genome Biol 4(3):207 (2003). Nav channel isoforms exhibit differential distributions, electrophysiological properties, and pharmacological properties. See e.g., Felts P. A., et al., Molecular brain research 45:71-82 (1997); Catterall, W. A., et al., Pharmacological reviews 57:397-409 (2005).

A number of neurological and psychiatric disorders, including Dravet syndrome, congenital insensitivity to pain, primary erythromelalgia, paroxysmal extreme pain disorder, cardiac arrhythmias, Brugada syndrome, and autism, are linked to Nav1.1, Nav1.2, and Nav1.6 channels. See e.g., Savio-Galimberti E., et al., Frontiers in pharmacology 3:124 (2012); Eijkelkamp, N., et al., Brain: a journal of neurology, 135 (Pt 9):2585-2612 (2012); O'Brien J. E. & Meisler M. H., Frontiers in genetics 4:213 (2013); Woodruff-Pak, D. S., et al., Behavioral neuroscience 120(2):229-240 (2006); Payandeh, J., et al., Nature 475:353-358 (2011); Liu G., et al. Neuropharmacology 44:413-422 (2003); Ragsdale, D. S., et al., *Proceedings of the National Academy of Sciences of the United States of America*, 93:9270-9275 (1996).

Among these three isoforms of Nav channels, Nav1.6 is expressed throughout soma and axon of different neuronal cells, and Nav1.6 has a significant contribution in persistent current, resurgent current, and repetitive neuronal firing. See e.g., Catterall W. A., et al., *Pharmacological reviews* 57:397-409 (2005); Schaller, K. L. & Caldwell, J. H., Cerebellum 2:2-9(2003). Both loss of function or gain of function from Nav1.6 channel mutations are related to malfunction of neuronal excitability. In animal models, mouse Scn8a (med) mutants showed dystonia, tremor, movement disorders, and sleep disorder. Furthermore, a number of de novo mutations have been identified in patients linked to epilepsy, ataxia, and cognitive disorders. See e.g., Savio-Galimberti E., et al, Frontiers in pharmacology 3:124 (2012).

Selective pharmacological modulators of Nav1.6 sodium channels are urgently needed. Most drugs targeting Nav channels on the market, including local anesthetic, antiepileptic, and antiarrhythmic agents, are proposed to interact with amino acid residues within the transmembrane S6 segment in Domain 4. See e.g., Payandeh J., et al., Nature 475:353-358 (2011). This site is highly conserved across all Nav channel isoforms, as such most Nav channel drugs show lack of selectivity across all Nav channel isoforms. See e.g., Fozzard H. A., et al., Frontiers in pharmacology 2:68 (2011); England, S. & de Groot, M. J. British journal of pharmacology 158:1413-1425 (2009).

This lack of specificity results in unwanted side effects such as inhibition of cardiac Nav1.5 channel. Therefore, there is an unmet need to develop novel, selective compounds targeting Nav channels. Currently, there is an ongoing effort both in industry and academia to develop isoform-specific inhibitors targeting Nav channels via high-throughput screening. Although there has been some success in the discovery of subtype specific Nav1.6 channel blockers based on structure-activity relationship (SAR) of Nav1.6 channels, novel approaches are still required to develop subtype specific compounds targeting Nav1.6 channels. See e.g., Yu H. B., et al., Acta pharmacologica Sinica 37:34-43 (2016); Rivara, M., et al., Bioorganic & medicinal chemistry letters 22:6401-6404 (2012).

BRIEF DESCRIPTION OF THE FIGURES

FIG. 2A: Chart (A) HEK293 cells were transiently transfected with CLuc-FGF14 and CD4-Nav1.6-NLuc and treated with ZL0141 (gray), ZL148 (green), ZL0181 (blue), ZL182 (orange) at 50 μM or DMSO (0.5%, control. The assembly of LCA pair was detected as luminescence response (RLU) upon addition of D-luciferin substrate at time zero; data are mean±SEM. Chart (B) Bar graph represents % maximal luminescence of treated compounds (50 μM), which is normalized to control (0.5% DMSO). The Statistical significance of the treated groups was compared to control using t-test (*$p<0.01$ or **$p<0.01$).

FIG. 2B: Chart (C) The peptidomimetics were tested against full-length luciferase reporter. Chart (D) Dose-response modulation of ZL0148, ZL0181 and ZL0182; data are mean±SEM. Panel A shows the SPR sensogram of WT FGF14 binding to Nav1.6.

FIG. 2C: Chart (E) The SPR sensogram of ZL0181 (10-200 μM) to Nav1.6 C-tail and Chart (F) the fitted saturation binding curves.

FIG. 2D: Chart (G) The SPR sensogram of ZL0181 (10-200 μM) to Nav1.6 C-tail and Chart (H) the fitted saturation binding curves.

FIG. 2E: (I) Electrostatic surface representation of ZL0181 peptidomimetic (magenta) was docked at the interface of FGF14:Nav1.6 homology model complex. (J) Ribbon representation of docking pose shows the interactions of ZL0181 (magenta) with Nav1.6 channel (yellow ribbon) and FGF14 (green ribbon). ZL0181 directly interacts with key residues ARG83, E156, T194 (FGF14) and N1833, K1853, R1854, R1892 (Nav1.6).

FIGS. 9A-E. Representative traces of Na+ transient currents (INa+) recorded from HEK-Nav1.6 cells transiently expressing (A, B) FGF13-1b, (D,E) FGF13-1a in response to depolarizing voltage steps in the presence of 30 µM ZL192 or DMSO. (C), (F) Bar graphs represent peak current densities derived from panel (A) and (B) at voltage step −5 mV. $p<0.05$, with ANOVA Dunn's test. n=8-17 cells per group.

DESCRIPTION

Figure 1:
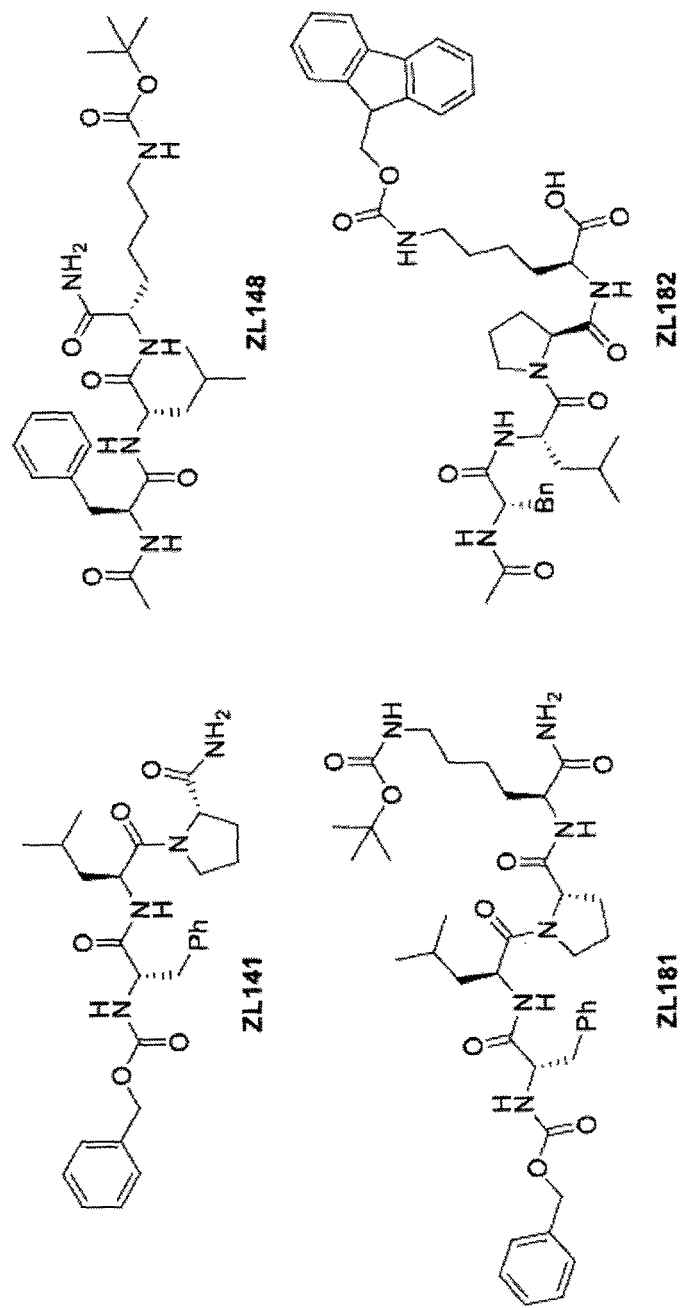
FIG. 1. Chemical Structures of Certain Embodiments of the Invention. Chemical structures of certain embodiments of the invention (namely, compounds ZL0141, ZL0148, ZL0181, and ZL0182).

All publications mentioned herein are incorporated by reference to the extent they support the present invention.

1.0 Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977), which is incorporated herein by reference in its entirety, for further examples of pharmaceutically acceptable salt).

The term "HBTU" refers to 3-[Bis(dimethylamino)methyliumyl]-3H-benzotriazol-1-oxide hexafluorophosphate (also known as 2-(1H-benzotriazol-1-yl)-1,1,3,3-tetramethyluronium hexafluorophosphate).

The term "HOBt" refers the following structure, known as 1-hydroxybenzotriazole, (including hydrates and polymorphs, thereof):

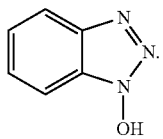

The term "DIEA" refers to N,N-Diisopropylethylamine (also known as Hünig's base, DIPEA, and ethyldiisopropylamine).

The term "DCM" refers to dichloromethane (also known as methylene chloride).

The term "TFA" refers to trifluoroacetic acid.

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —(CH$_2$)$_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —NH$_2$ group.

An "amido" group refers to an —CONH$_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-CH$_2$— etc.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkyl sulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—C(O)NR$_2$), unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —NH$_2$, —NH($C_{1-4}$alkyl), —N(C1-4alkyl)$_2$, —NO2, —S($C_{1-4}$alkyl), —SO$_2$($C_{1-4}$alkyl), —CO$_2$($C_{1-4}$alkyl), and —O($C_{1-4}$alkyl).

ZL0181 is used throughout this description interchangeably with ZL181 to refer to:

ZL0181

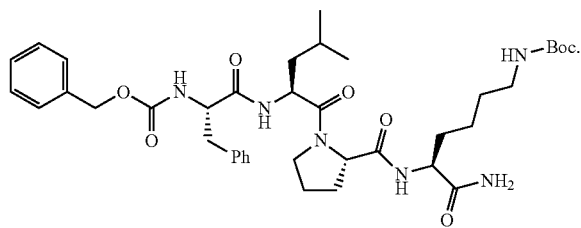

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

It is to be understood that both the foregoing descriptions are exemplary, and thus do not restrict the scope of the invention.

2.0 Novel Peptidomimetic Compounds

Current medications in psychiatry suffer of specificity as they rely on old neuropharmacology of target broad indiscriminate class of molecules that are expressed everywhere in the brain. There is a need for targeted, fine-tune regulators of the brain circuit that can lead to targeted therapeutics with limited side effects.

The inventors have discovered and validated a peptide-derivative mapped to the FGF14:Nav1.6 complex interface and shown it has in vitro-to-ex vivo activity in the brain circuit. See example, FIGS. 2-5 of the present application.

Furthermore, the inventors have discovered certain small molecules can selectively target Nav1.6 channels in the presence of FGF14.

2.1 Compounds of Formula I

The present invention provides a compound of the Formula I and pharmaceutically acceptable salts thereof, wherein:

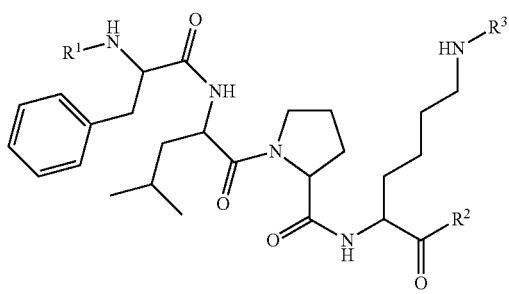

Formula I (FLPK)

wherein:

$R^1$ and $R^3$ are independently selected from H, alkyl, arylalkyl, —(CO)$R^4$, —(CO)O$R^5$, or Fmoc; where $R^4$ is alkyl, arylalkyl, or aryl; $R^5$ is alkyl, arylalkyl, or aryl;

$R^2$ is H, —OH, alkoxy, or —N$R^6R^7$; where $R^6$ and $R^7$ are independently selected from H, alkyl, aryl, or heteroaryl; or $R^6$ and $R^7$ are optionally joined to form a N-containing heterocycle with 1-4 heteroatoms; and wherein, if $R^2$ is OH, then $R^1$ and $R^3$ are not both hydrogen.

In certain embodiments, each chiral carbon of the compounds of Formula I may independently be R- or S configuration.

In some embodiments of Formula I, $R^1$ is —(CO)$R^4$, wherein $R^4$ is methyl.

In some embodiments of Formula I, $R^1$ is —(CO)O$R^5$, wherein $R^5$ is benzyl.

In some embodiments of Formula I, $R^1$ is —(CO)$R^4$, wherein $R^4$ is phenyl.

In some embodiments of Formula I, wherein $R^3$ is H, Boc, or Fmoc.

In some embodiments of Formula I, $R^2$ is —N$R^6R^7$.

In some embodiments of Formula I, $R^2$ is alkoxy

In some embodiments of Formula I, $R^2$ is methoxy.

In further embodiments of invention, the compound of Formula I is one of:

ZL0173

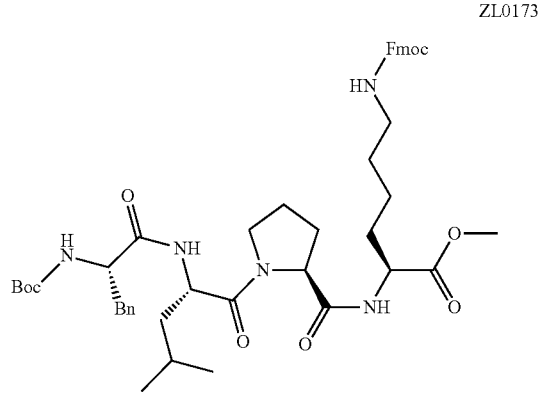

ZL0175

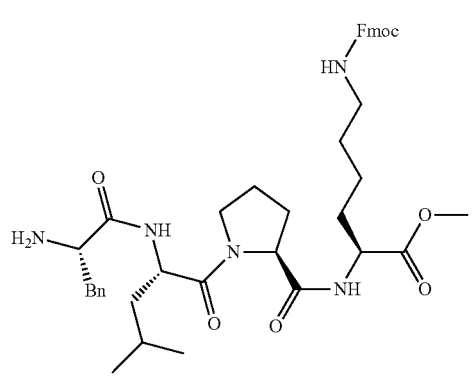

ZL0177
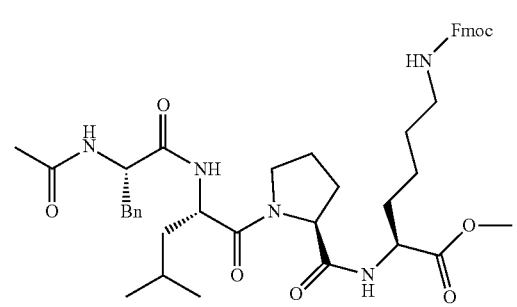
ZL0182
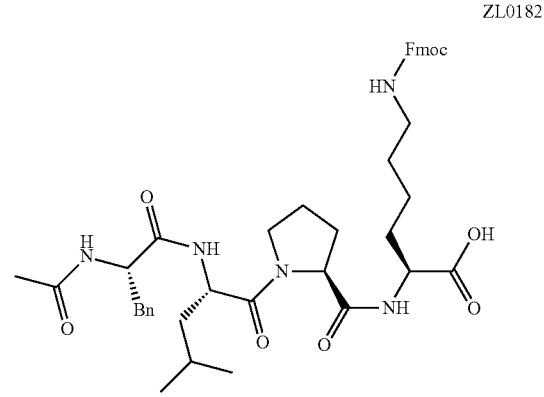
ZL0183
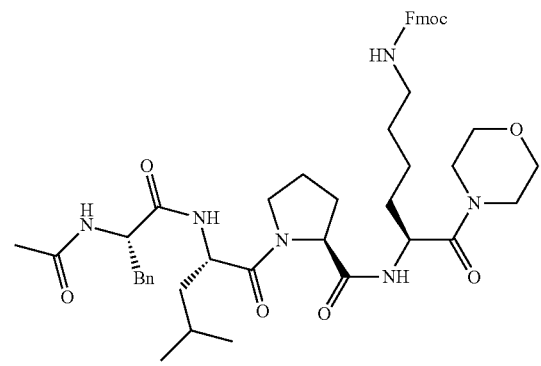
ZL0184
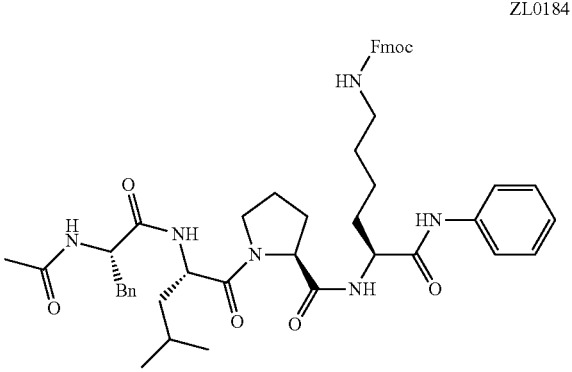
ZL0185
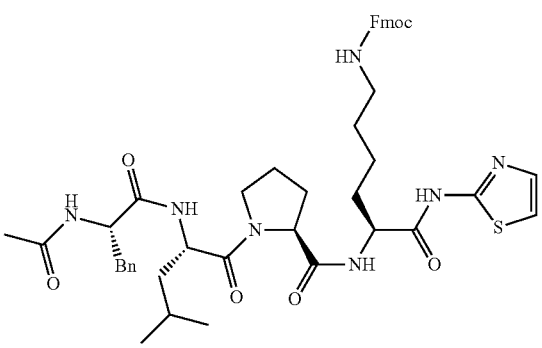
ZL0181
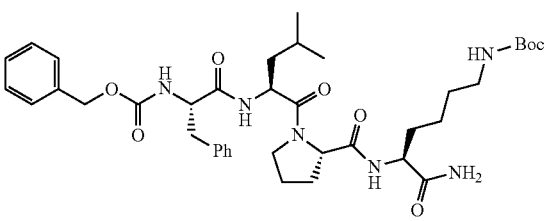
ZL0186
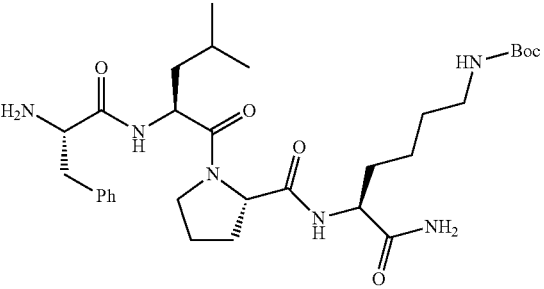
ZL0188
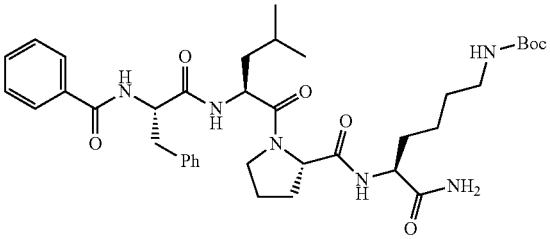
ZL0192
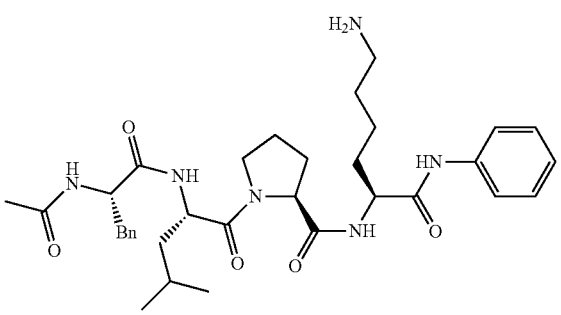
2.2 Synthesis of Compounds of Formula I
The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain compounds of Formula I can be prepared as exemplified by the following synthetic scheme (Scheme 1):

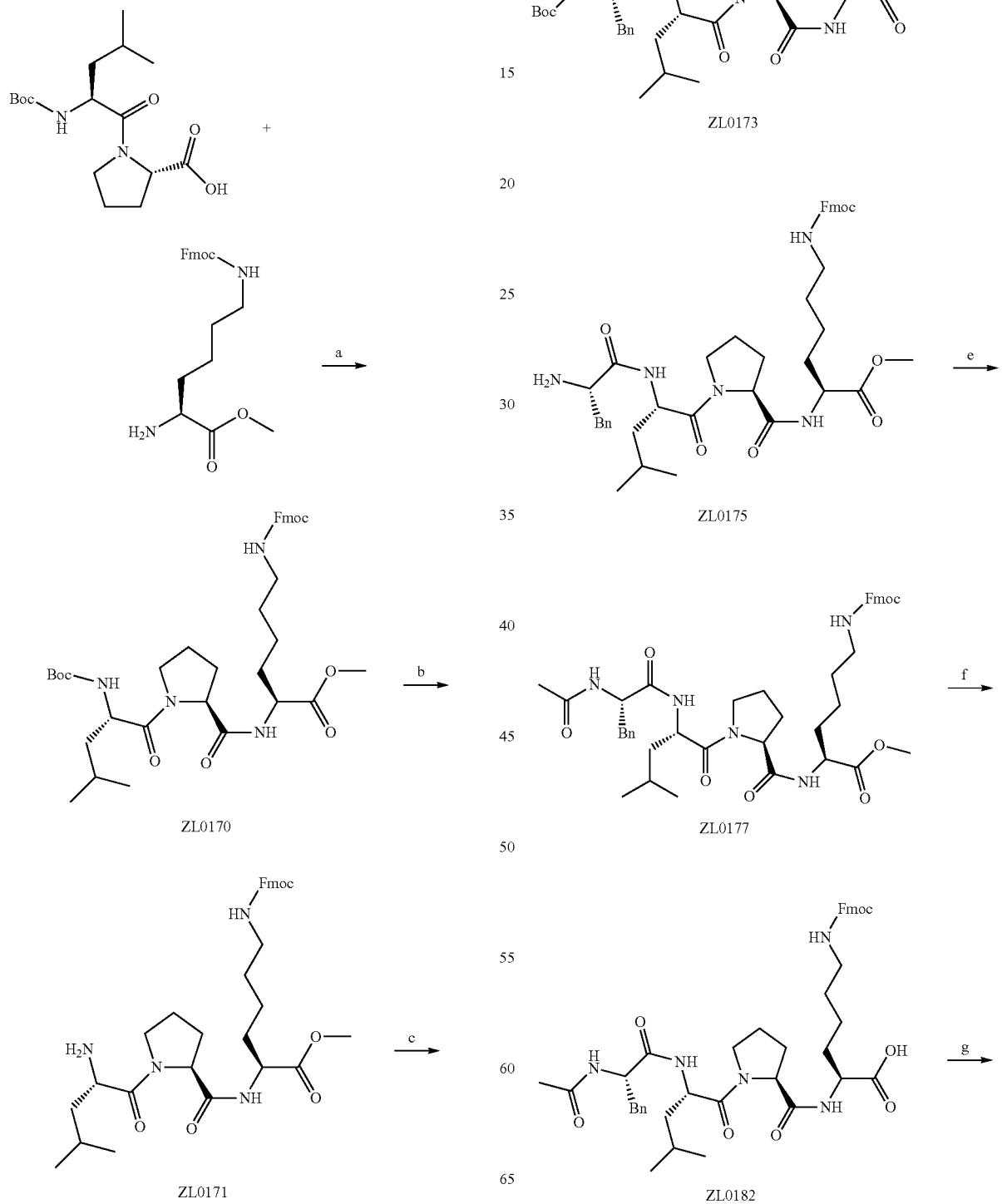

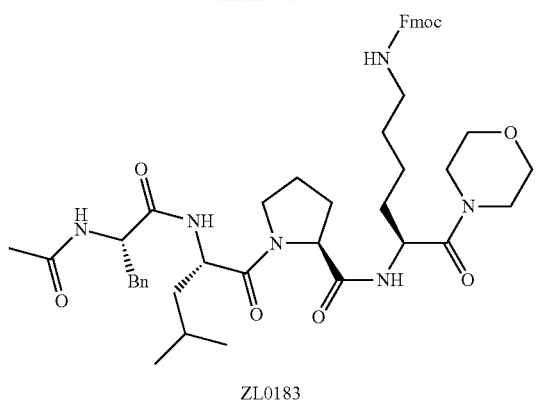

ZL0183

Reagents and conditions:
a HBTU, HOBt, DIEA, DCM, rt, quant.;
b TFA, DCM, rt, 87%;
c (tert-butoxycarbonyl)-L-phenylaianine, HBTU, HOBt, DIEA, DCM, rt, 81%;
d TFA, DCM, rt, quant.;
e CH₃COCl, Et₃N, DCM, rt, 91%;
f LiOH·H₂O, CH₃OH/H₂O, rt, 91%.
g morpholine, HBTU, HOBt, DIEA, DCM, rt, quant.

In some embodiments, preparation of certain compounds of Formula I may occur via a condensation reaction (to introduce an amide moiety) as exemplified with the preparation of compounds ZL0184 and ZL0188:

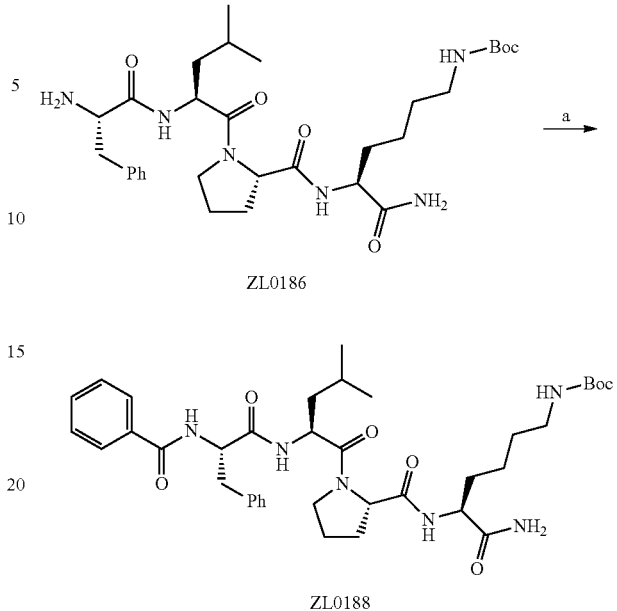

Reagents and conditions:
a benzoyl chloride, Et₃N, DCM, rt, 43%.

In some embodiments, preparation of certain compounds of Formula I may occur via removal of a N-protecting group (such as Fmoc) as exemplified with the preparation of compound ZL0192:

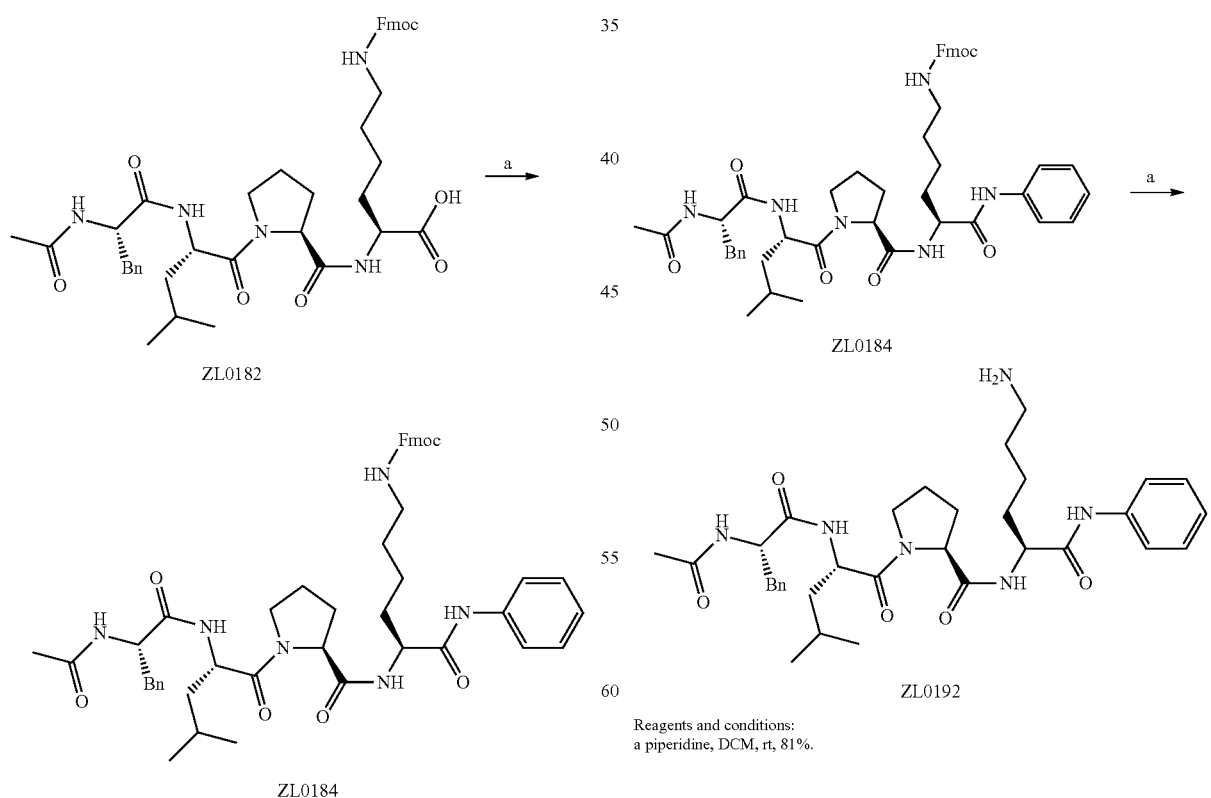

Reagents and conditions:
a piperidine, DCM, rt, 81%.

Reagents and conditions:
a aniline, HBTU, HOBt, DIEA, DCM, rt, 90%.

In some embodiments, preparation of certain compounds of Formula I may occur as exemplified (for the preparation of ZL0181) in Scheme 2 below:

Scheme 2. Synthetic Route for Certain Compounds of Formula I

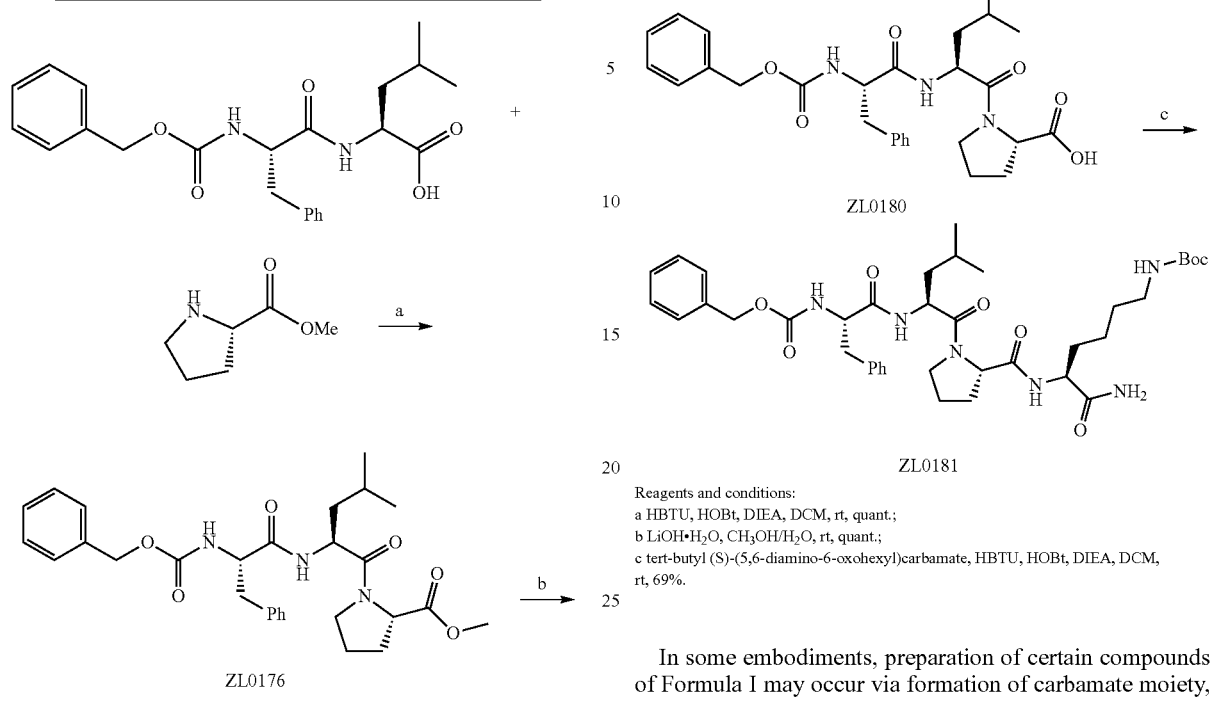

Reagents and conditions:
a HBTU, HOBt, DIEA, DCM, rt, quant.;
b LiOH·H₂O, CH₃OH/H₂O, rt, quant.;
c tert-butyl (S)-(5,6-diamino-6-oxohexyl)carbamate, HBTU, HOBt, DIEA, DCM, rt, 69%.

In some embodiments, preparation of certain compounds of Formula I may occur via formation of carbamate moiety, as exemplified with the preparation of compound ZL0186:

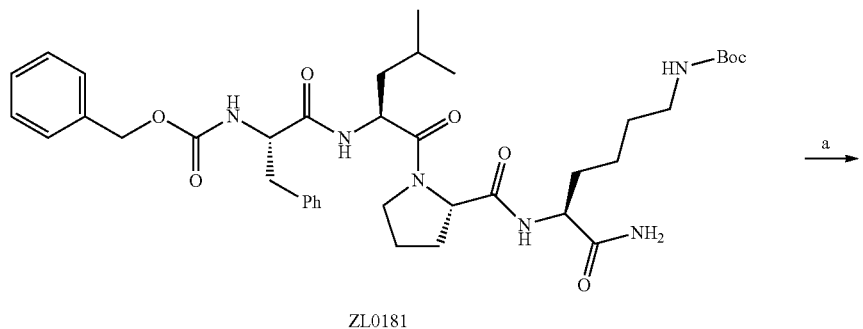

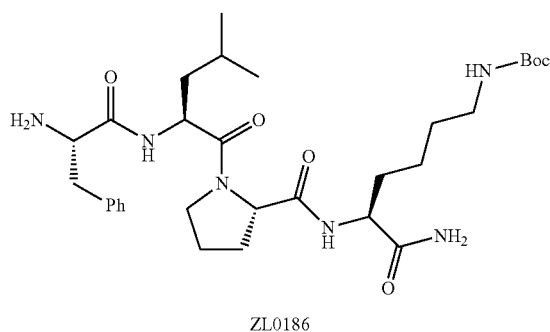

Reagents and conditions:
a 10% Pd/C, CH₃OH, H₂, rt, 91%.

2.3 Compounds of Formula II

The present invention provides a compound of the Formula II and pharmaceutically acceptable salts thereof,

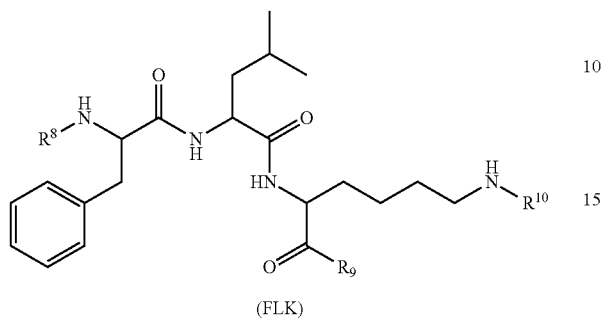

Formula II (FLK)

wherein:
R$^8$ and R$^{10}$ are independently selected from H, alkyl, arylalkyl, —(CO)R$^4$, —(CO)OR$^5$, or Fmoc; where R$^4$ is alkyl, arylalkyl, or aryl; where R$^5$ is alkyl, arylalkyl, or aryl;
R$^9$ is H, —OH, alkoxy, or —NR$^6$R$^7$, where R$^6$ and R$^7$ are independently selected from H, alkyl, aryl, or heteroaryl; or R$^6$ and R$^7$ are optionally joined to form a N-containing heterocycle with 1-4 heteroatoms; and
wherein, when R$^9$ is OH, then R$^8$ and R$^{10}$ are not both hydrogen.

In certain embodiments, each chiral carbon of the compounds of Formula II may independently be R- or S configuration.

In some embodiments, R$^8$ is H, —(CO)R$^4$, or —(CO)OR$^5$.

In some embodiments, when R$^8$ is —(CO)OR$^5$ and R$^5$ is benzyl.

In some embodiments, R$^9$ is —NH$_2$.

In some embodiments, R$^{10}$ is H, Boc, or Fmoc.

In some embodiments, the compounds of Formula II is one of:

ZL0142

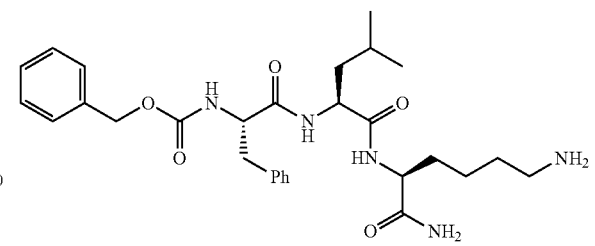

ZL0145

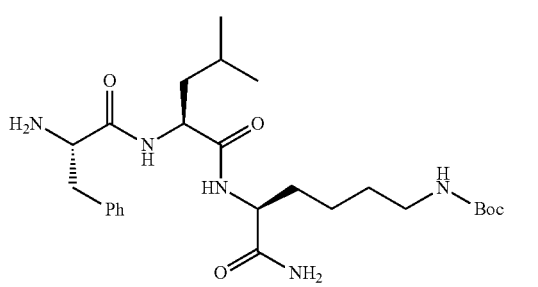

ZL0146

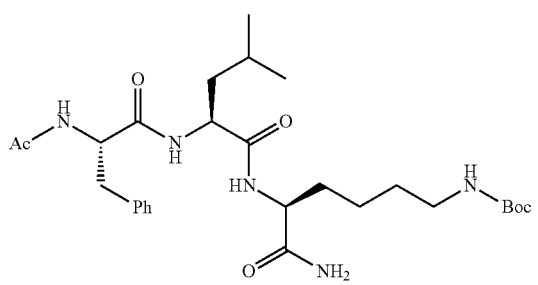

ZL0148

2.4 Synthesis of Compounds of Formula II

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain compounds of Formula II can be prepared via a condensation reaction as exemplified by preparation of compounds ZL0142, ZL0146, and ZL0148, as shown in the following synthetic scheme (Scheme 3):

Scheme 3. Synthetic Route for Certain Compounds of Formula II

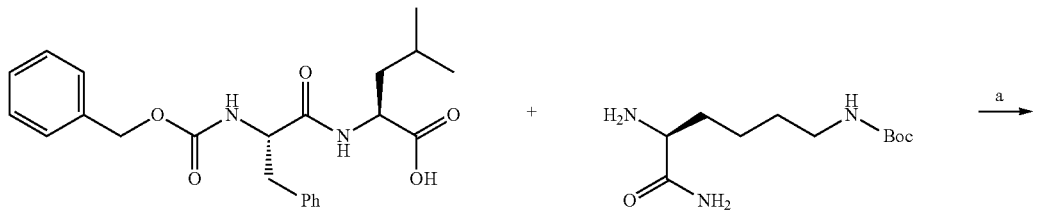

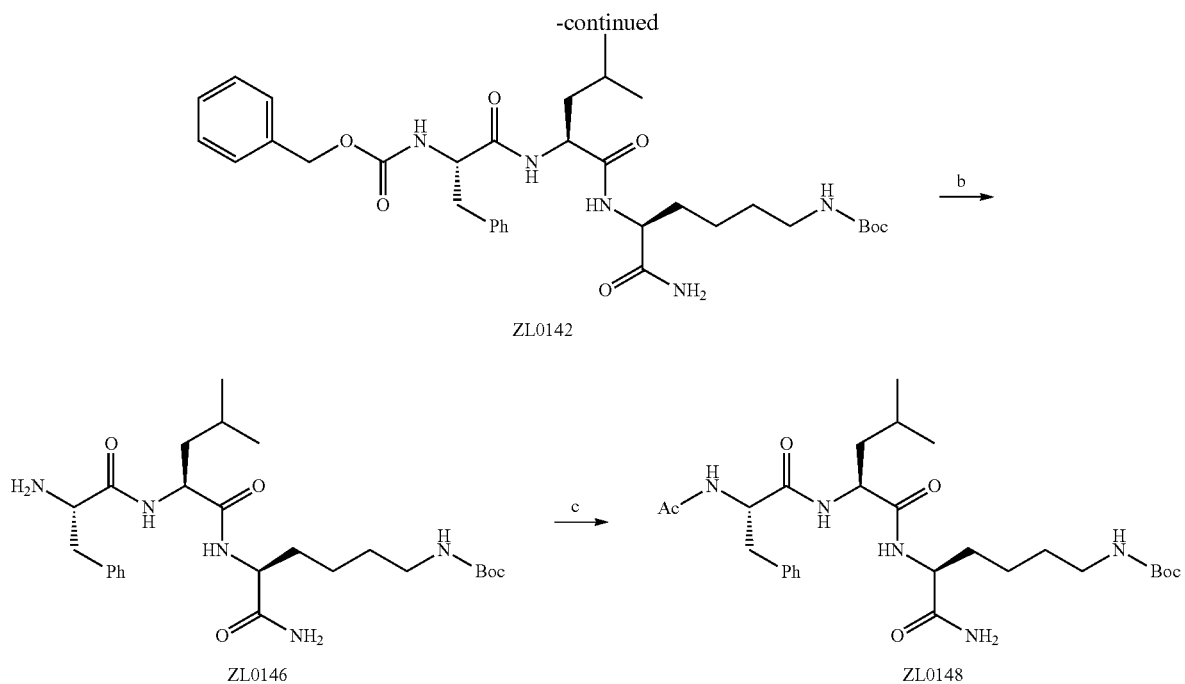

ZL0142

ZL0146    ZL0148

Reagents and conditions:
a HBTU, HOBt, DIEA, DCM, rt, 61%;
b 10% Pd/C, H₂, CH₃OH, rt, quant.;
c CH₃COCl, NEt₃, DCM, rt, 29%.

In some embodiments, preparation of certain compounds of Formula II may occur via removal of a N-protecting group, such as Boc, as exemplified with the preparation of compound ZL0145:

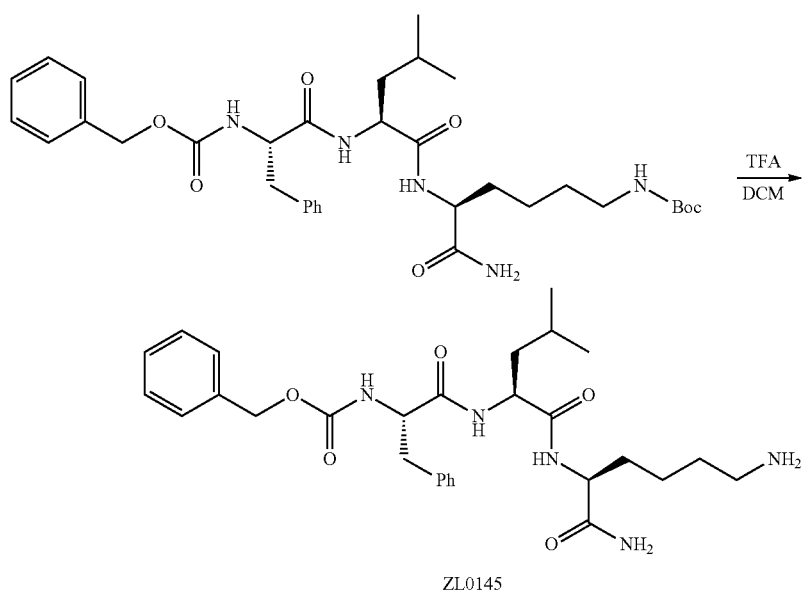

ZL0145

2.5 Compounds of Formula III

The present invention provides a compound of the Formula III and pharmaceutically acceptable salts thereof, Formula III

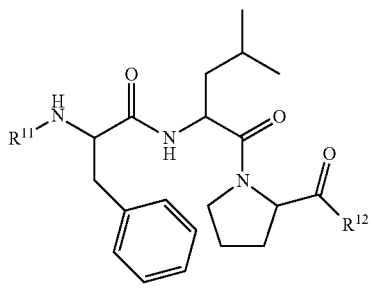

(FLP)

wherein:

$R^{11}$ is H, alkyl, arylalkyl, —(CO)$R^4$, —(CO)O$R^5$, or Fmoc, where $R^4$ is alkyl, arylalkyl, or aryl, where $R^5$ is alkyl, arylalkyl, or aryl;

$R^{12}$ is H, —OH, alkoxy, or —N$R^6R^7$, where $R^6$ and $R^7$ are independently selected from H, alkyl, aryl, or heteroaryl, or $R^6$ and $R^7$ are optionally joined to form a N-containing heterocycle with 1-4 heteroatoms; and wherein if $R^{12}$ is OH, then $R^{11}$ is not hydrogen.

In certain embodiments, each chiral carbon of the compounds of Formula III may independently be R- or S configuration.

In some embodiments, $R^{12}$ is —OH, methoxy, or —NH$_2$.

In further embodiments, compounds of Formula III may be a compound of Formula IIIa, wherein $R^{11}$ is —(CO)O$R^5$ and $R^5$ is benzyl:

Formula IIIa

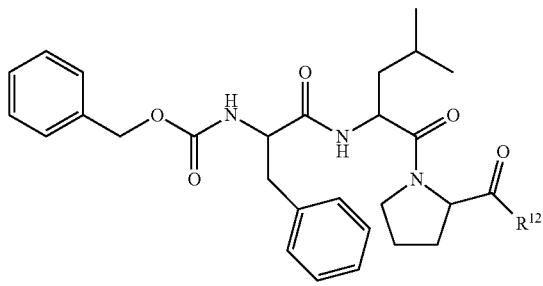

In some embodiments, the compound of Formula III is one of:

ZL0141

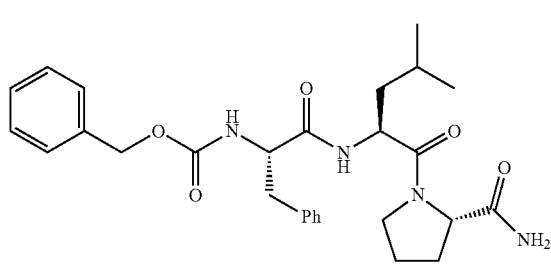

ZL0176

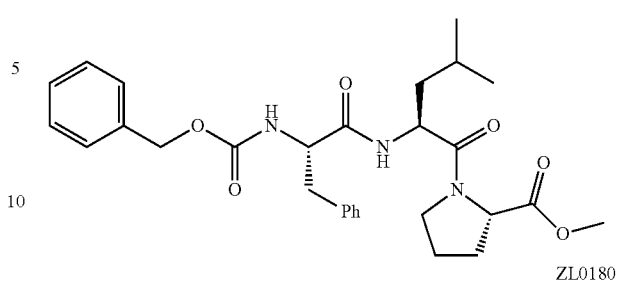

ZL0180

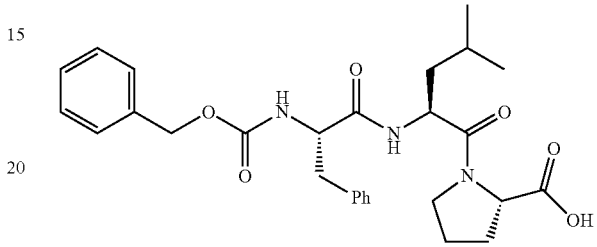

2.6 Synthesis of Compounds of Formula III

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain compounds of Formula III can be prepared via a condensation reaction (to introduce an amide moiety) as exemplified with the preparation of compound ZL0141, below and compounds ZL0176 and ZL0180 (see Scheme 2, above):

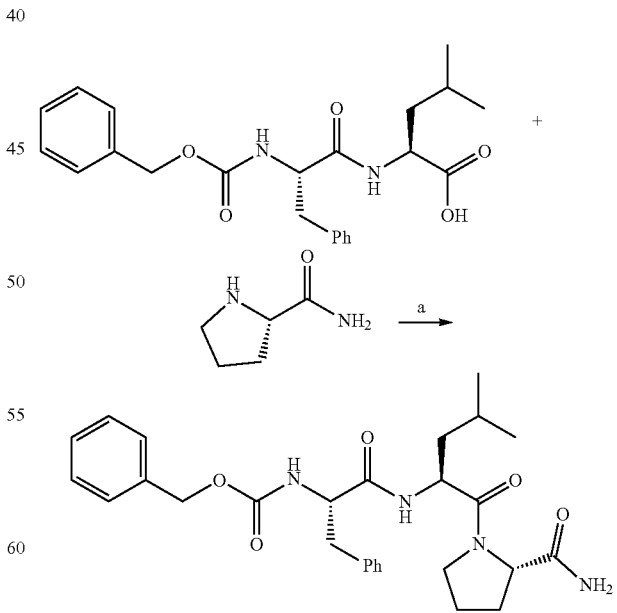

ZL0141

Reagents and conditions:
a HBTU, HOBt, DIEA, DCM, rt, quant.

2.7 Compounds of Formula IV

The present invention provides a compound of the Formula IV and pharmaceutically acceptable salts thereof,

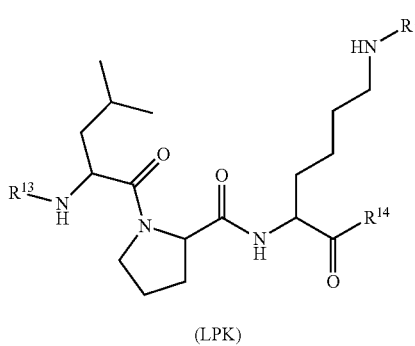

(LPK)

wherein:

$R^{13}$ and $R^{15}$ are independently selected from H, alkyl, arylalklyl, —(CO)$R^4$, —(CO)O$R^5$, or Fmoc, where $R^4$ is alkyl, arylalkyl, or aryl, where $R^5$ is alkyl, arylalkyl, or aryl; and $R^{14}$ is H, —OH, alkoxy, or —N$R^6R^7$, where $R^6$ and $R^7$ are independently selected from H, alkyl, aryl, or heteroaryl, or $R^6$ and $R^7$ are optionally joined to form a N-containing heterocycle with 1-4 heteroatoms; and wherein if $R^{14}$ is OH, then $R^{13}$ and $R^{15}$ are not both hydrogen.

In certain embodiments, each chiral carbon of the compounds of Formula IV may independently be R- or S configuration.

In some embodiments, $R^{13}$ is H, —(CO)$R^4$, or —(CO)O$R^5$.

In further embodiments, wherein $R^{13}$ is acetyl or Boc.

In some embodiments, $R^{14}$ is —NH$_2$ or methoxy.

In some embodiments, wherein $R^{15}$ is H, Boc, or Fmoc.

In some embodiments, the compound of Formula IV is one of:

ZL0143

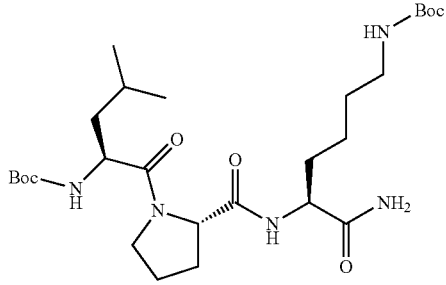

ZL0170

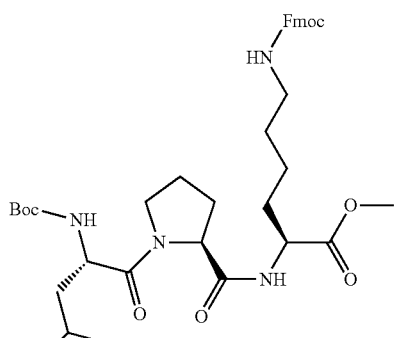

ZL0147

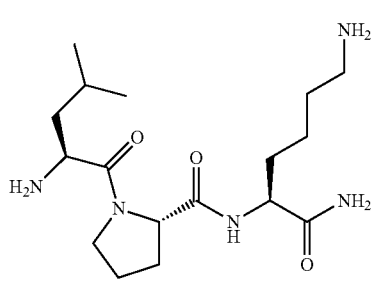

ZL0171

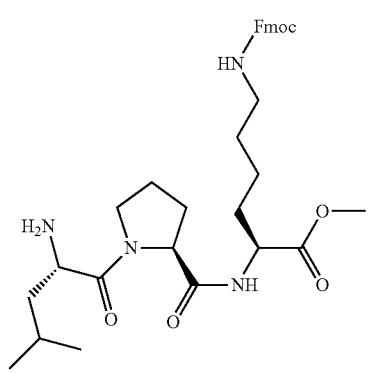

ZL0172

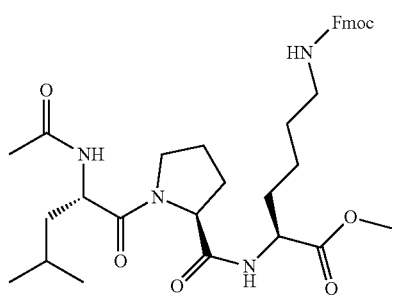

2.8 Synthesis of Compounds of Formula IV

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain compounds of Formula IV can be prepared via a condensation reaction, as exemplified by preparation of compound ZL0143, or by deprotection of a N-protecting group(s) (such as Boc or Fmoc) as exemplified by preparation of compound ZL0147:

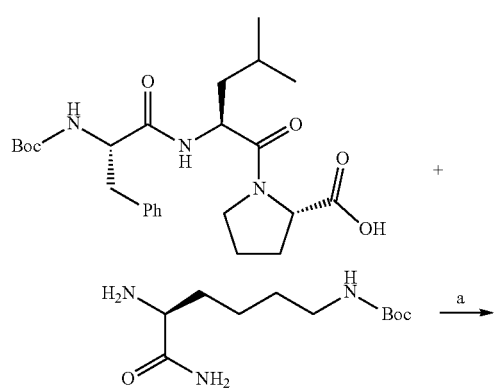

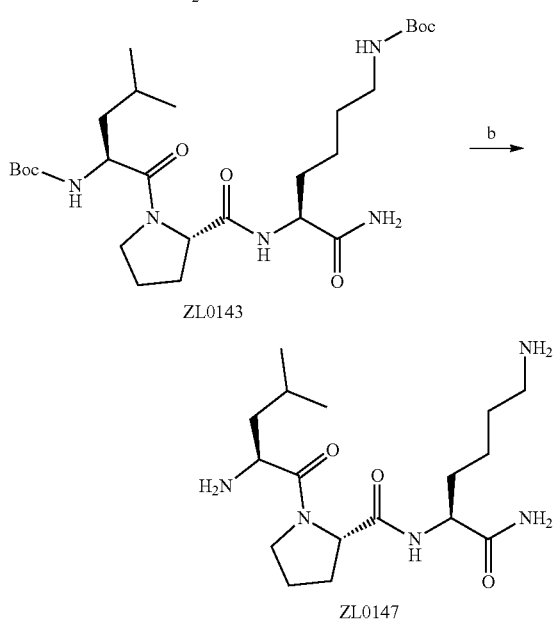

ZL0143

ZL0147

Reagents and conditions:
a HBTU, HOBt, DIEA, DCM, rt, quant.;
b TFA, DCM, rt, quant.

Additionally, certain compounds of Formula IV can be prepared via a condensation reaction, as exemplified by preparation of compounds ZL0170 (Scheme 1, above), or by preparation of compound ZL0171 (Scheme 1, above).

Furthermore, certain compounds of Formula IV can be prepared via an amidation reaction, as exemplified by preparation of compound ZL0172:

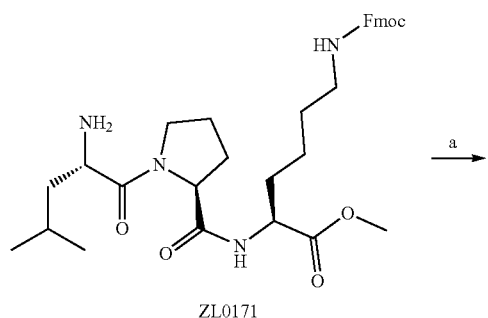

ZL0171

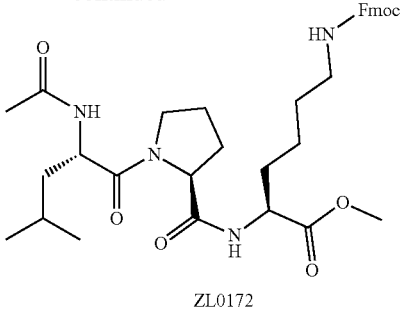

ZL0172

Reagents and conditions:
a CH$_3$COCl, Et$_3$N, DCM, rt, 81%.

3.0 Method of Use

In some embodiments, one or more of the compounds of Formulas I-IV may be used to modulate Nav1.6 Channels.

In some embodiments, one or more of the compounds of Formulas I-IV may be used to modulate Nav1.6 Channels alone.

In some embodiments, one or more of the compounds of Formulas I-IV may used in the presence of an accessory protein, such as FGF14 and/or FGF13, to modulate Nav1.6 channel. In some embodiments, one or more of the compounds of Formulas I-IV may be used in the presence, or absence, of FGF14 to treat mood disorders, depression, anxiety, addiction and other diseases associated with the reward circuit. In other embodiments, one or more of the compounds of Formulas I-IV may used in the presence of an accessory protein, such as FGF14 to modulate cognitive function. Additionally, one or more of the compounds of Formulas I-IV may be used in the presence of FGF14 to treat epileptic seizures.

In some embodiments, the invention encompasses a method of treating mood disorders, depression, anxiety, addiction and other diseases associated with the reward circuit, epileptic seizures, and/or modulate cognitive function, said method comprising administering one or more compounds of Formulas I-IV to a subject, optionally with an accessory protein such as FGF13 and/or FGF14.

In other embodiments, ZL181 may be used to treat mood disorders, depression, anxiety, addiction and other diseases associated with the reward circuit, or epileptic seizures, or to modulate cognitive function.

In further embodiments, one or more of the compounds of Formulas I-IV may be used in the presence of an accessory protein, such as FGF13, to modulate Nav1.6 channels. In some embodiments, one or more of the compounds of Formulas I-IV may be used in the presence, or absence, of FGF13 to treat epilepsy or neuroinflammatory pain.

In some embodiments, ZL192 may be used to treat epilepsy or neuroinflammatory pain.

In further embodiments, ZL181 may be used to modulate Nav1.6 channels.

In further embodiments, ZL181 may be used in the presence of FGF14 to modulate Nav1.6 channels.

In other embodiments, ZL192 may be used to modulate Nav1.6 channels.

In other embodiments, ZL192 may be used in the presence of FGF13 to modulate Nav1.6 channels.

In some embodiments, the invention encompasses a method of treating mood disorders, depression, anxiety, addiction and other diseases associated with the reward circuit, epileptic seizures, and/or modulate cognitive function comprising administering compound ZL181 to a subject, optionally with an accessory protein such as FGF13 and/or FGF14.

In some embodiments, the invention encompasses a method of treating epilepsy or neuroinflammatory pain, said method comprising administering one or more of the compounds of Formulas I-IV to a subject, optionally in the presence of an accessory protein, such as FGF13 and/or FGF14.

In some embodiments, the invention encompasses a method of treating epilepsy or neuroinflammatory pain comprising administering compound ZL192 to a subject, optionally with an accessory protein such as FGF13.

In some embodiments, the invention encompasses a method of modulating one or more Nav1.6 Channels, comprising contacting one or more cells with one or more compounds of Formulas I-IV, optionally with an accessory protein such as FGF13 and/or FGF14.

In some embodiments, the invention encompasses a method of modulating one or more Nav1.6 Channels, comprising contacting one or more cells with ZL181 and/or ZL192, optionally with an accessory protein such as FGF13 and/or FGF14.

4.0 EXAMPLES

The following examples are provided solely to illustrate the present invention and are not intended to limit the scope of the invention, described herein.

Figure 3A:
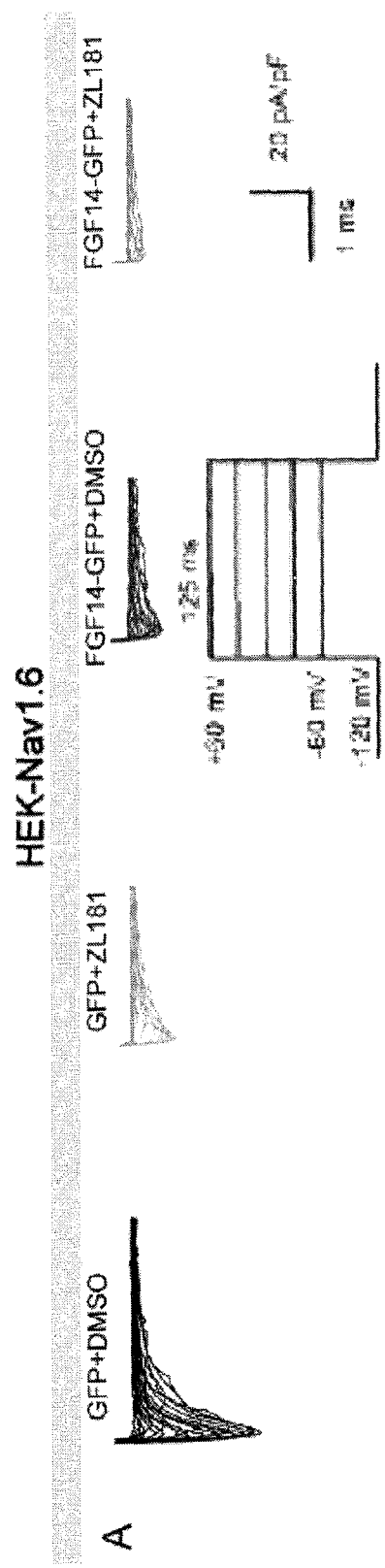
FIG. 3A-D. Compounds of the invention, as exemplified using compound ZL0181, modulates Nav1.6 channels alone and works synergistically with FGF14 to further modulate Nav1.6 channels. Chart (A) Representative traces of voltage-gated Na+ currents ($I_{Na}$) recorded from HEK-Nav1.6 cells transiently expressing GFP or FGF14-GFP in response to voltage steps from −120 mV to +60 mV from a holding potential of −70 mV (inset). Only selected current traces in response to voltage steps are shown. GFP-expressing cells were treated with 0.15% DMSO (black traces) or with 20 μM ZL0181 (orange traces), whereas FGF14-GFP-expressing cells were treated either with 0.15% DMSO (blue traces) or with 20 μM ZL0181 (gray traces). Chart (B) current-voltage relationships of $I_{Na}$ from the experimental groups described in A. Chart (C) Bar graphs representing peak current densities measured in individual HEK-Nav1.6 cells expressing GFP (treated with 0.15% DMSO; black bar), GFP (treated with 20 μM ZL0181; orange bar) FGF14 (treated with 0.15% DMSO; blue bar), or FGF14 (treated with 20 μM ZL0181; gray bar). Data are mean±S.E. Treatment with ZL0181 to cells expressing GFP (orange bar) suppresses peak current densities in comparison with DMSO-treated control (**$p<0.01$, Kruskal-Wallis, post hoc Dunn test). Treatment of ZL0181 to cells expressing FGF14-GFP (gray bar) suppresses peak current densities in comparison with DMSO-treated control (#$p<0.05$, unpaired t test). Chart (D) Voltage dependences of $I_{Na}$ activation and Chart (E) steady-state inactivation were measured and means±S.E. Values are plotted as a function of the membrane potential. The activation and inactivation data were fitted with the Boltzmann function. Chart (F) Treatment with ZL0181 inhibits Na+ current in a dose-response manner in Nav1.6 channels alone. Chart (G) Treatment with ZL0181 inhibits Na+ current in a dose-response manner in Nav1.6 channels with expression of FGF14.
Figure 3B:
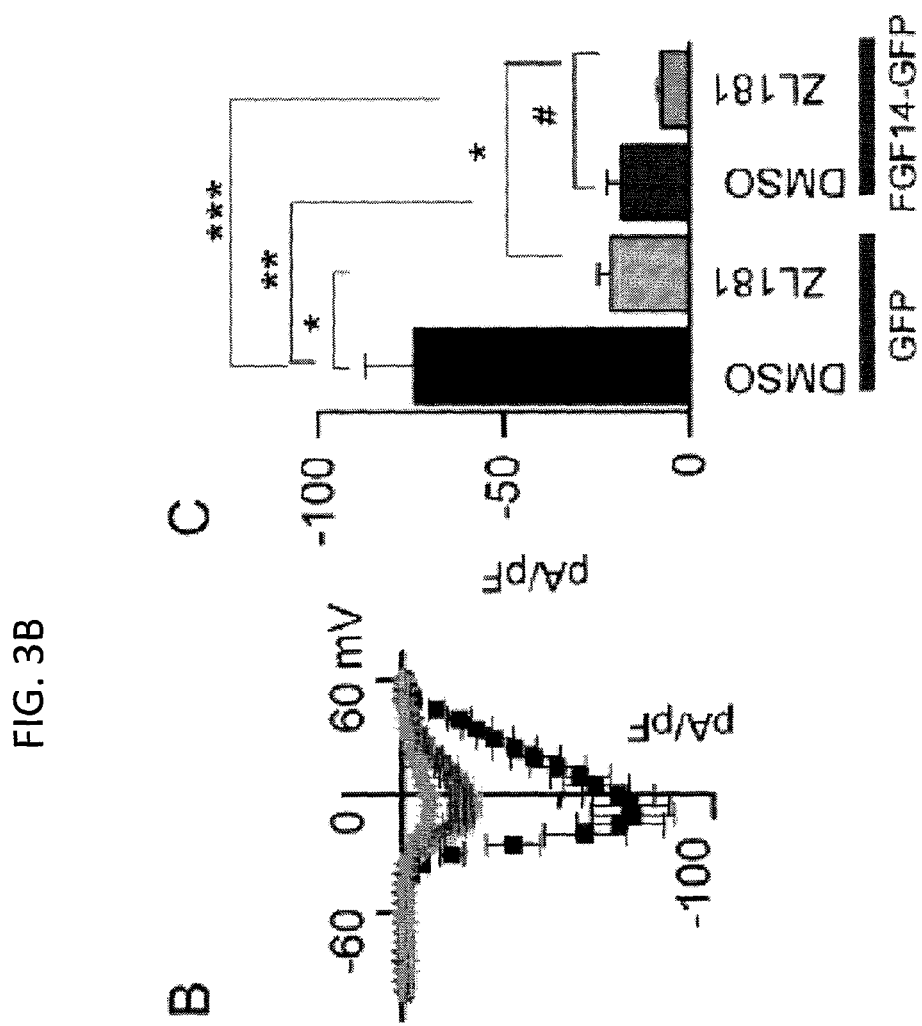
Figure 3C:
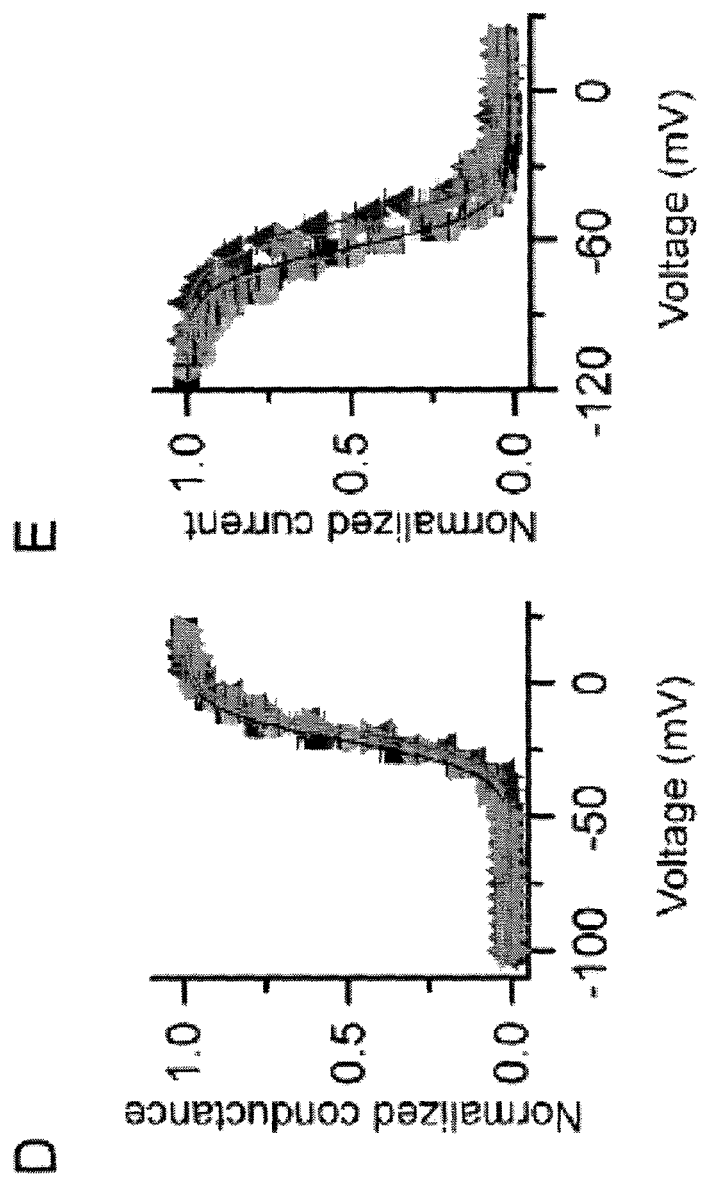

Example 1. The Compounds of the Invention, as Exemplified by, Compound ZL0181 Peptidomimetic Modulates Nav1.6 Channels Alone and Works Synergistically with FGF14 to Modulate Nav1.6 Channels To determine the role of compounds of the invention in Nav1.6 channels alone and Nav1.6 channels in the presence of FGF14, 2×2 experimental groups using compound ZL0181, an exemplary embodiment, were designed. HEK-Nav1.6 cells were transiently transfected with GFP or FGP-GFP and treated with either DMSO (0.15% final concentration, control group) or ZL0181 (20 μM, final concentration) 20-60 min prior to the experiments. As shown in FIG. 3A, rapid rising and fast decaying transient inward Na+ currents were evoked in response to depolarizing voltage steps from Nav1.6 channels transfected with GFP. In cells pretreated with ZL0181 (20 μM), the Nav1.6-mediated peak current density was significantly lower (−20.9±3.4 pA/pF, n=12, $p<0.05$) compared to control (−73.8±13.6 pA/pF, n=12; FIG. 3B, Chart C). ZL0181 does not change activation and inactivation properties of Nav channel alone (FIG. 3C). Thus, ZL0181 inhibits peak current amplitude of Na1.6 current.

The role of ZOL181 in Nav1.6 channel in the presence of FGF14 was then investigated. In agreement with previous studies (see e.g., Shavkunov, A. S., et al., The Journal of Biological Chemistry 288:19370-19385(2013)), it was found that that HEK-Nav1.6 cells expressing FGF14-GFP shows significantly lower Na+ current (INa) amplitudes than cells expressing GFP (−18.1±3.8 pA/pF, n=20, for FGF14-GFP-expressing cells; −73.8±13.6 pA/pF, n=12, for GFP-expressing cells, **$p<0.01$, one-way ANOVA, post hoc Bonferroni, see FIG. 3B, Chart C). Notably, ZL0181 further decreases in Na+ current peak amplitude (−7.4±4.4 pA/pF, n=19, for FGF14-GFP-expressing cells treated with ZL0181 compared with FGF14-GFP-expressing cells (DMSO), $p<0.05$, unpaired t test, see FIG. 3B, Chart C). Furthermore, the role of ZL0181 to modulate the biophysical properties of Nav1.6 channel in the presence of FGF14 was investigated. In consistency with previous studies, voltage dependence of activation and steady-state inactivation kinetics changes in the cells expressing FGF14-GFP compared with control (FIG. 3C). Interestingly, treatment with ZL0181 rescued the depolarizing shift of the steady-state inactivation induced by FGF14-GFP expression back to control levels ($p>0.05$, one-way ANOVA, post hoc Dunnett's test; FIG. 3C). Thus, ZL0181 works synergistically with FGF14 to regulate the peak current amplitude as well as the inactivation kinetics.

Figure 3D:
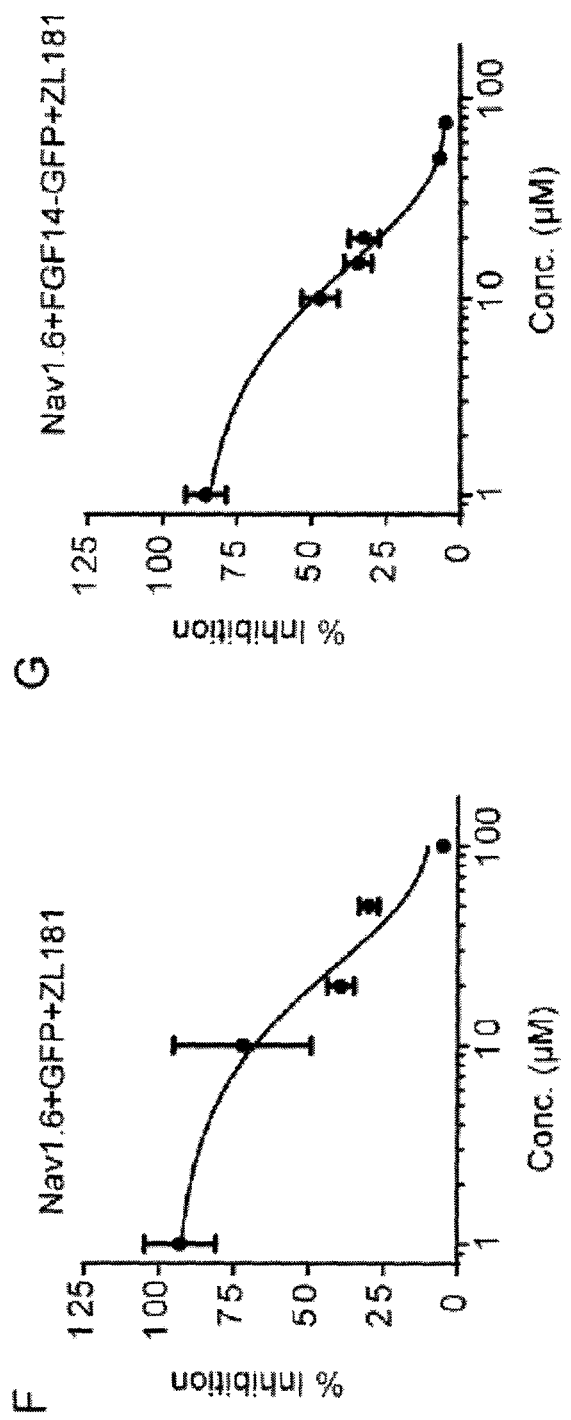

Furthermore, using a range of doses from 1 μM to 100 μM a dose-response profile for ZL0181 in HEK293-Nav1.6 cells alone and HEK-Nav1.6 cells transfected with FGF14 was developed. Compound ZL0181 was surprisingly found to exhibit dose-dependent inhibition of Nav1.6 encoded currents that exhibits an IC50 of 19.67±5.7 μM (FIG. 3D, Chart F), and ZL0181 exhibits dose-dependent inhibition of Nav1.6 encoded currents in presence of FGF14 (IC50=11.55±1.3 μM) (FIG. 3D, Graph G).

The role of ZL0181 in regulating Nav1.1 and Nav1.2 channels was also investigated. Although ZL0181 also suppresses peak current amplitude in Nav1.1 and Nav1.2 channels like Nav1.6 channel, it does neither act synergistically to further suppress Na+ current in presence of FGF14 or rescue the voltage-dependence inactivation property (V1/2) in presence of FGF14 to the control (GFP, DMSO).

Example 2. The Compounds of the Invention, as Exemplified by, Compound ZL0181 Decreases Neuronal Intrinsic Excitability in Nucleus Accumbens (NAc) Medium Spiny Neurons (MSN)

Figure 4A:
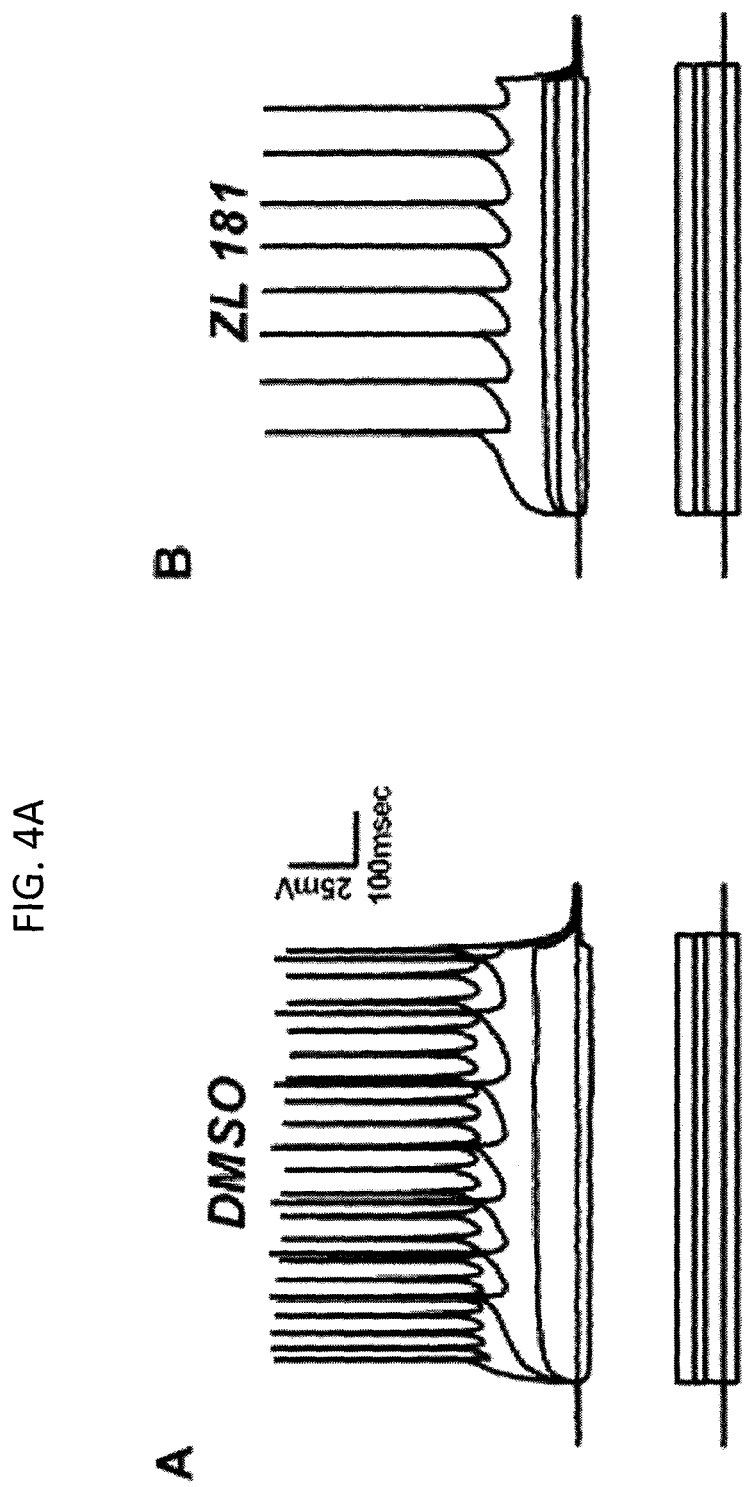
FIGS. 4A-C. The effect of compounds of the invention, as exemplified using compound ZL0181 on neuronal firing in medium spiny neurons of nucleus accumbens. Charts (A-B) Representative traces showing trains of action potentials evoked by current steps of fixed increments in MSNs treated with 0.05% DMSO (A) or 50 µM of ZL0181. Chart (B) Representative traces of action potential are shown at −20, 0, 50, 80 and 110 pA current steps of 800 ms duration. Chart (C) Input-output curve showing reduced number of spikes in MSN treated with ZL0181 compared to DMSO control. Charts (D-E) Graph bars for voltage and current thresholds showing increased voltage and current thresholds for MSN treated with ZL0181 compare to DMSO control. $*p<0.05$, $p<0.01$, $*p<0.005$ with Student t-test.
Figure 4B:
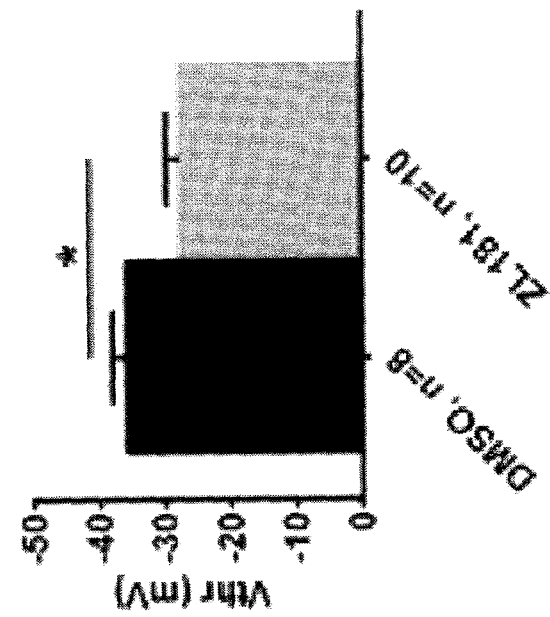
Figure 4B:
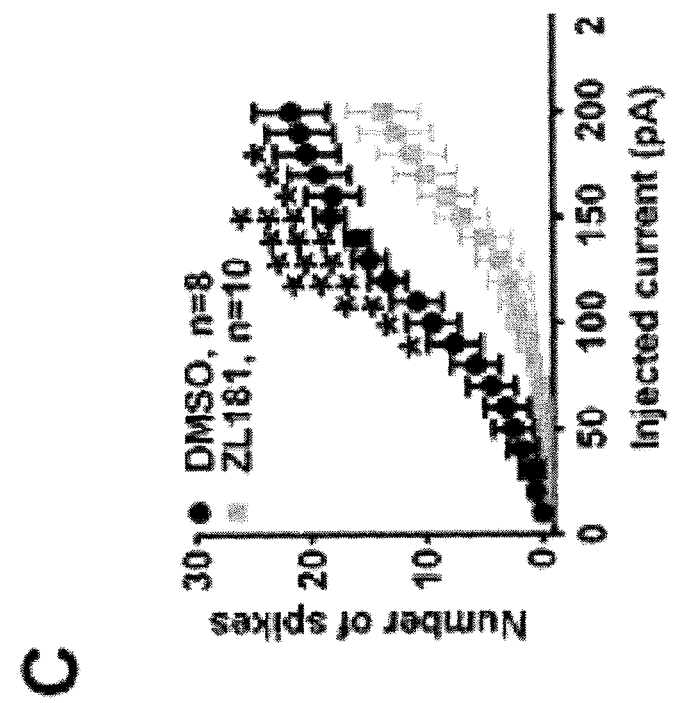
Figure 4C:
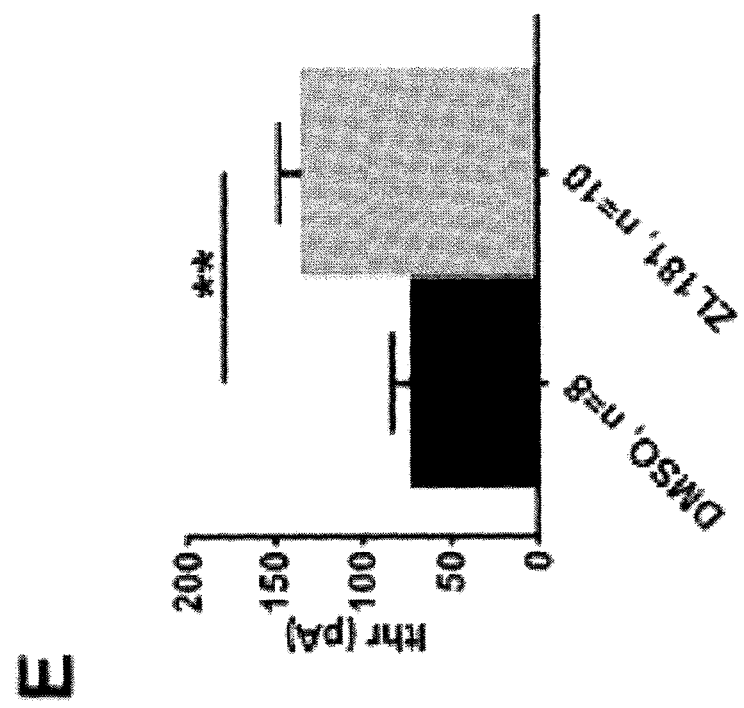
Figure 5:
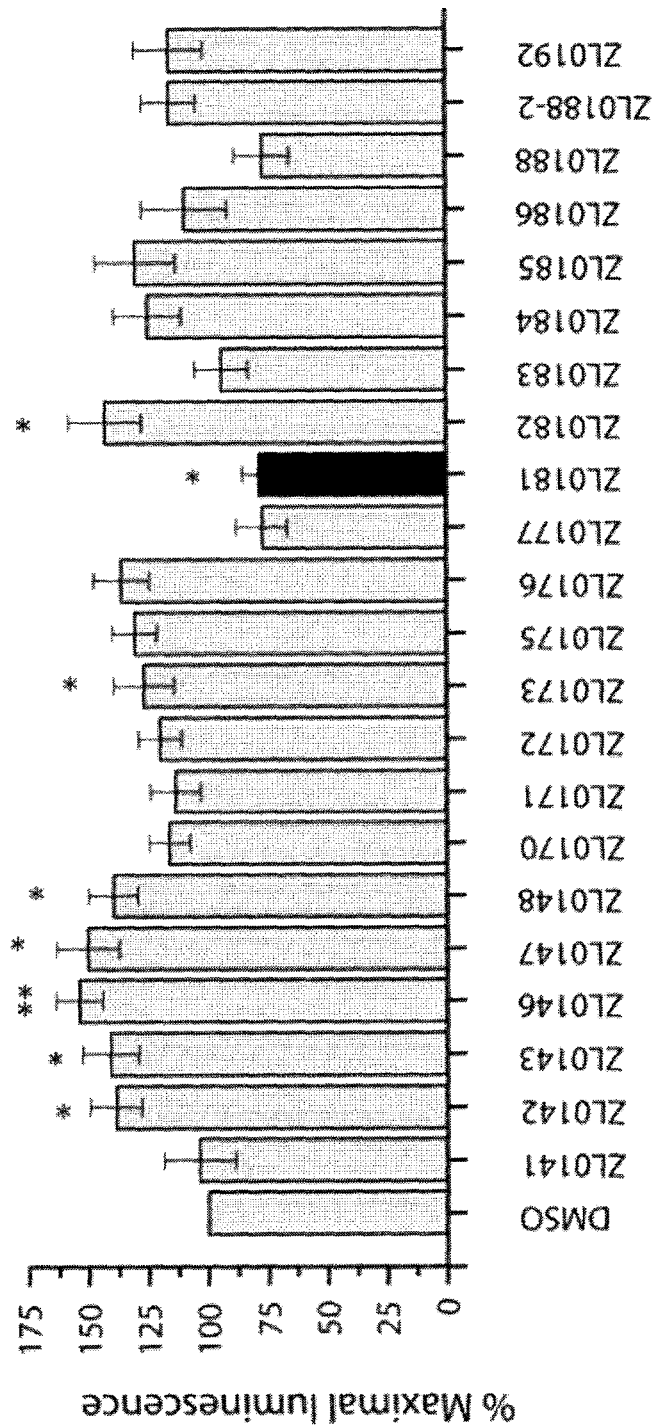
FIG. 5. Validation of peptidomimetics by LCA against the FGF14:Nav1.6. Activity bar chart summarizing the results of validation by LCA (by measuring % maximal luminescence of certain embodiments of the invention).
Figure 6A:
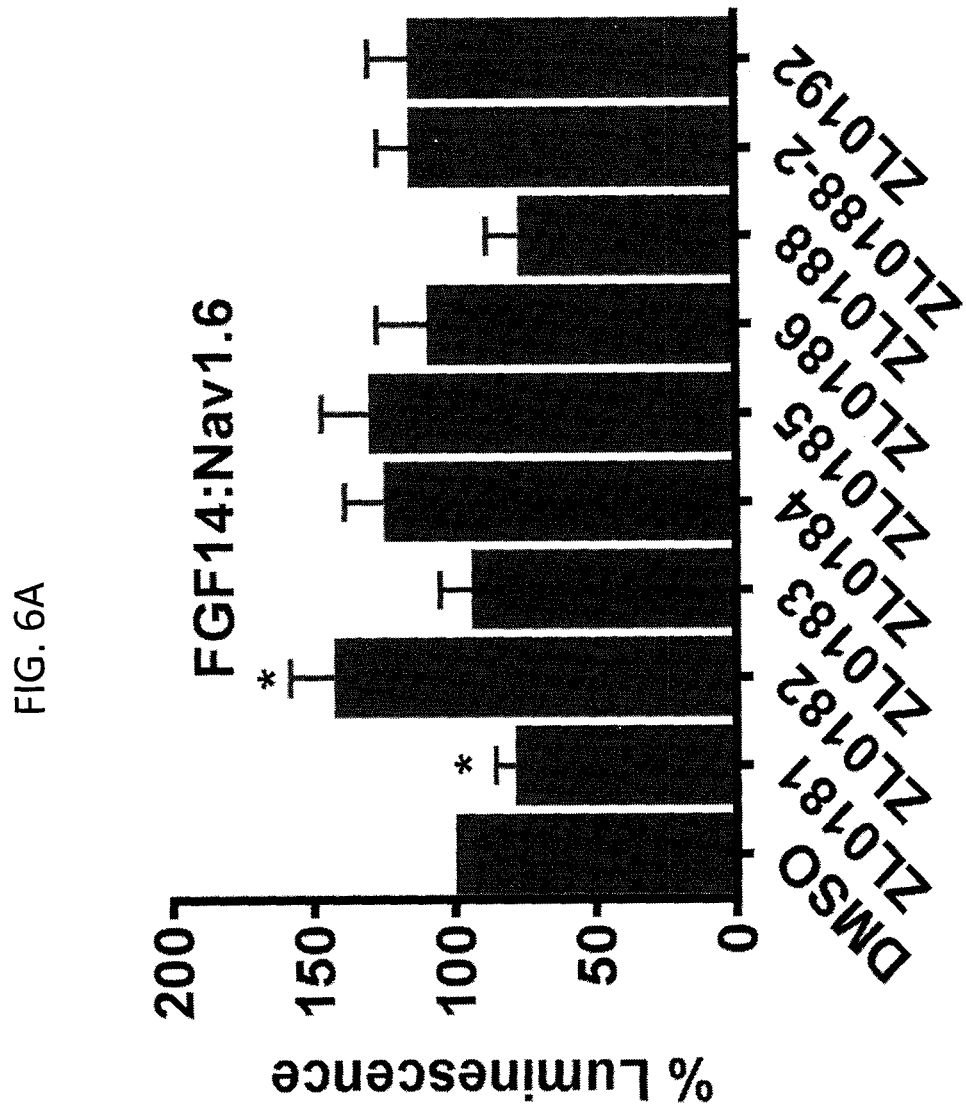
FIGS. 6A-C. Bar graph represents maximal luminescence response (normalized to DMSO) measured upon complementation of construct (A) CLuc-FGF14 with CD4-Nav1.6-Nluc (B) CLuc-FGF13-1a with CD4-Nav1.6-Nluc (C) CLuc-FGF13-1a with CD4-Nav1.6-Nluc, after incubation for two hours with 50 µM peptidomimetics. Data are represented as mean±SEM. $*p<0.05$, $p<0.01$, $*p<001$ with student t-test.
Figure 6B:
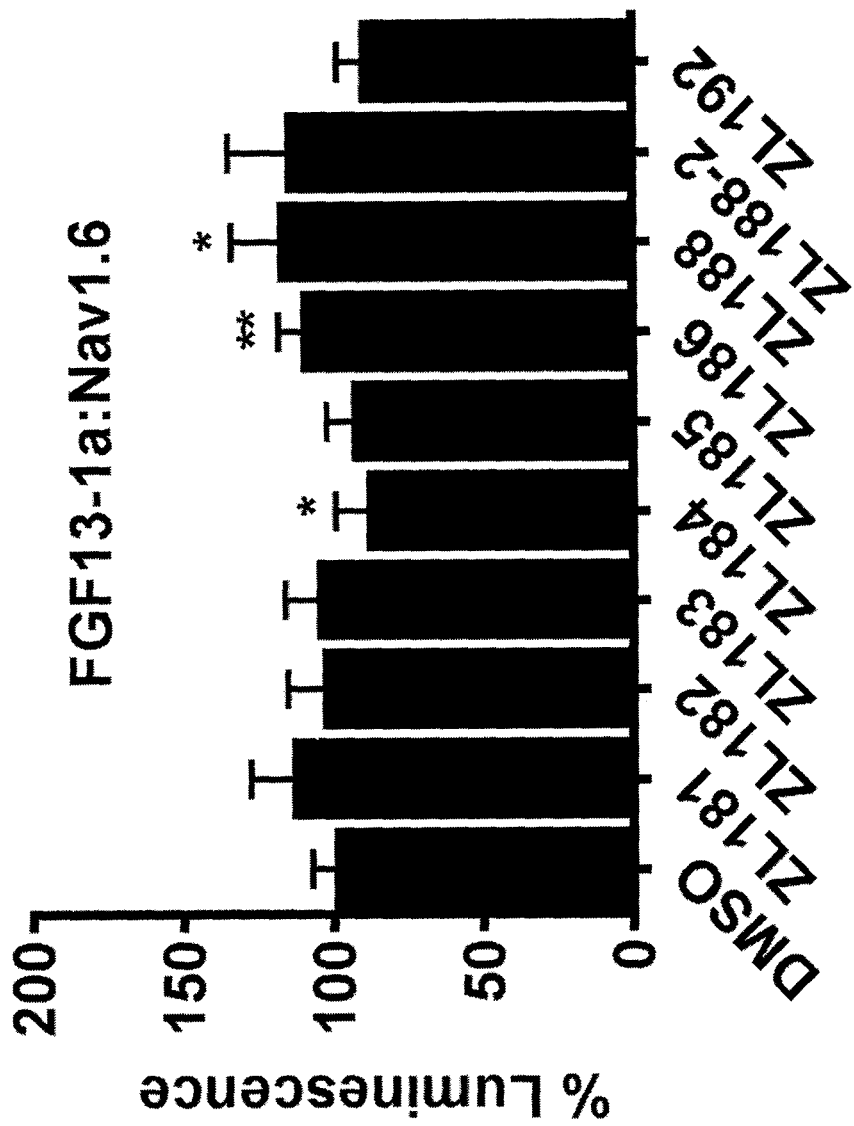
Figure 6C:
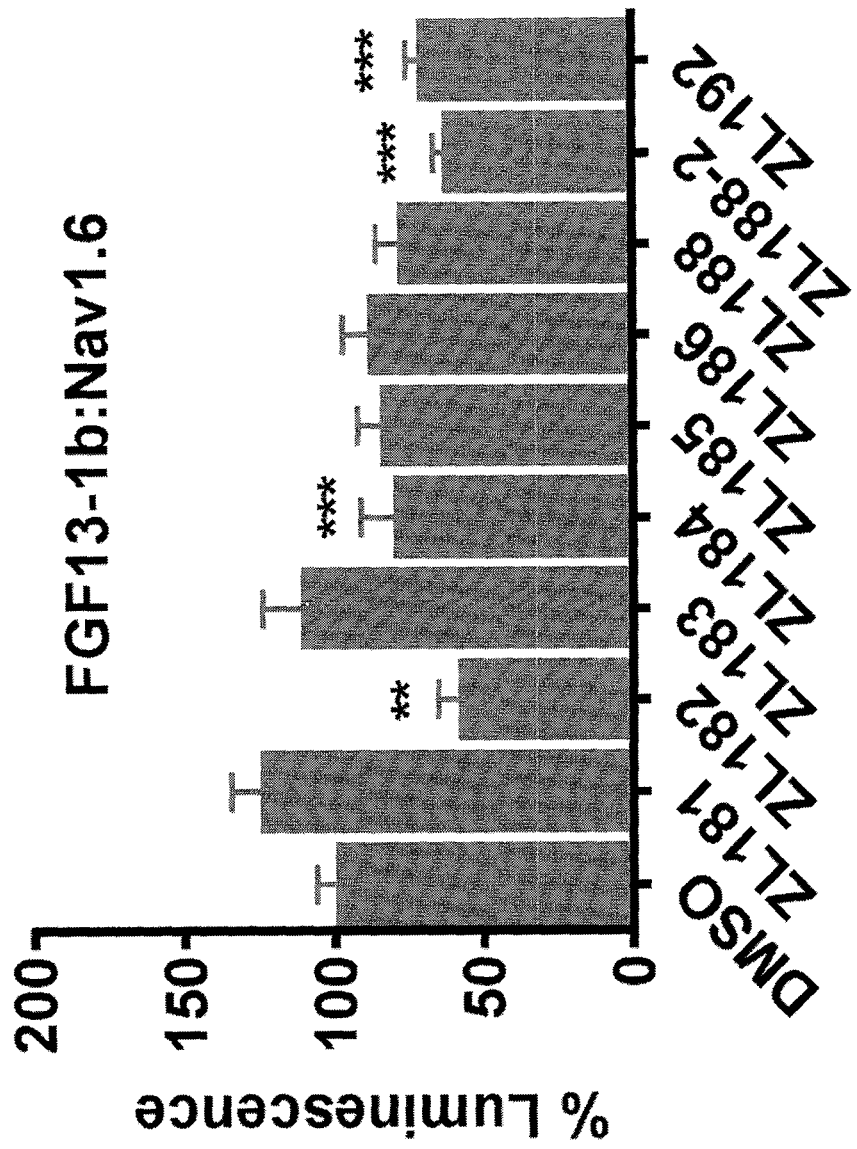
Figure 7:
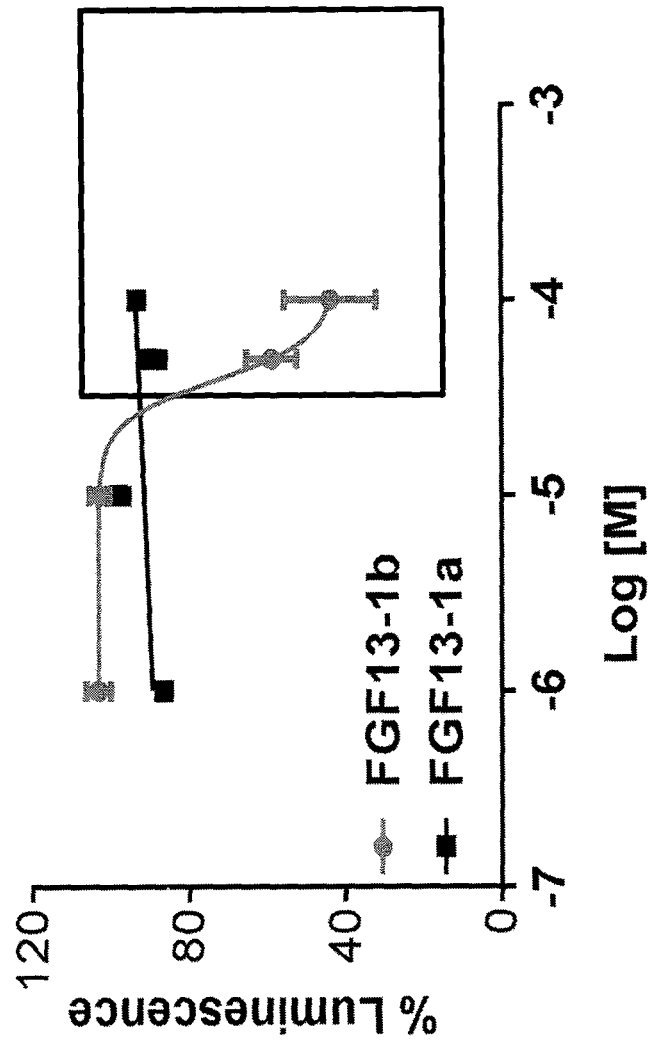
FIG. 7. Dose response curve represents maximal luminescence response (normalized to DMSO) measured upon complementation of CLuc-FGF13-1a/b with CD4-Nav1.6-Nluc at 1, 10, 50 and 100 µM ZL192 incubation.
Figure 8:
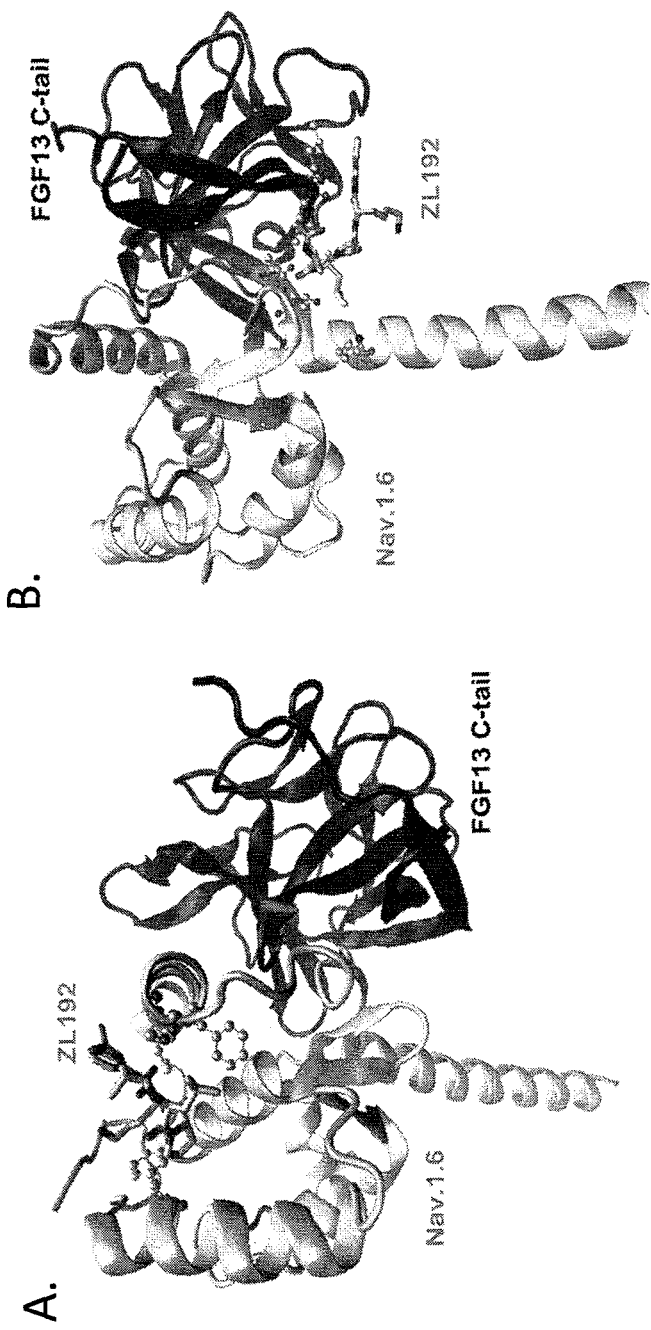
FIGS. 8A-B. Nav1.6 C-tail:FGF13 homology model was built based on the Nav.15 C-tail:FGF13 crystal structure (PDB ID: 4DCK). ZL192 docked on this homology model using the SwissDock software. (A) ZL192 docked in the central pocket of Nav1.6 (highest rank based on free energy, $\Delta G$) (B) ZL192 docked at the Nav1.6 C-tail:FGF13 interface.
Figure 9A:
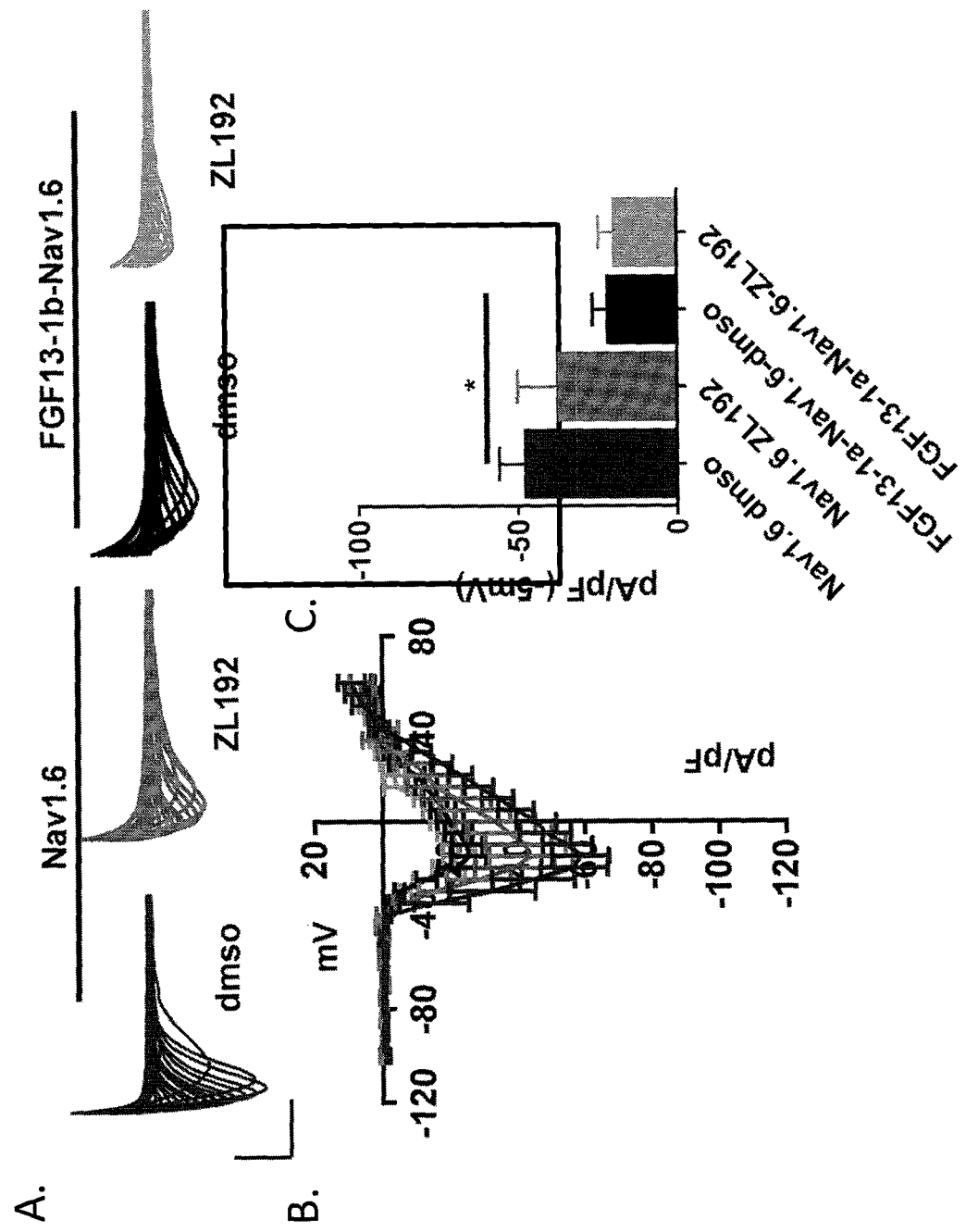
Figure 9B:
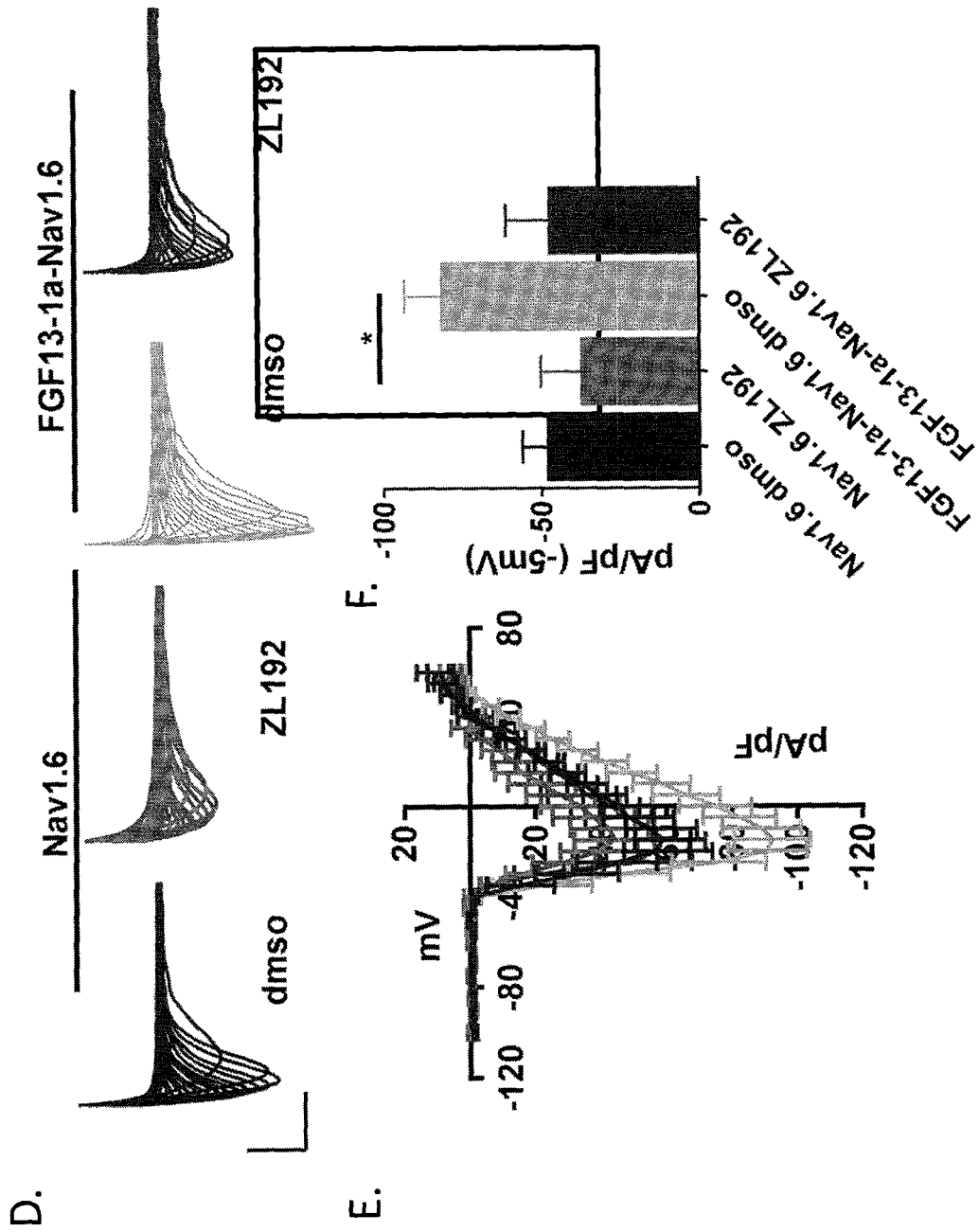
Figure 10A:
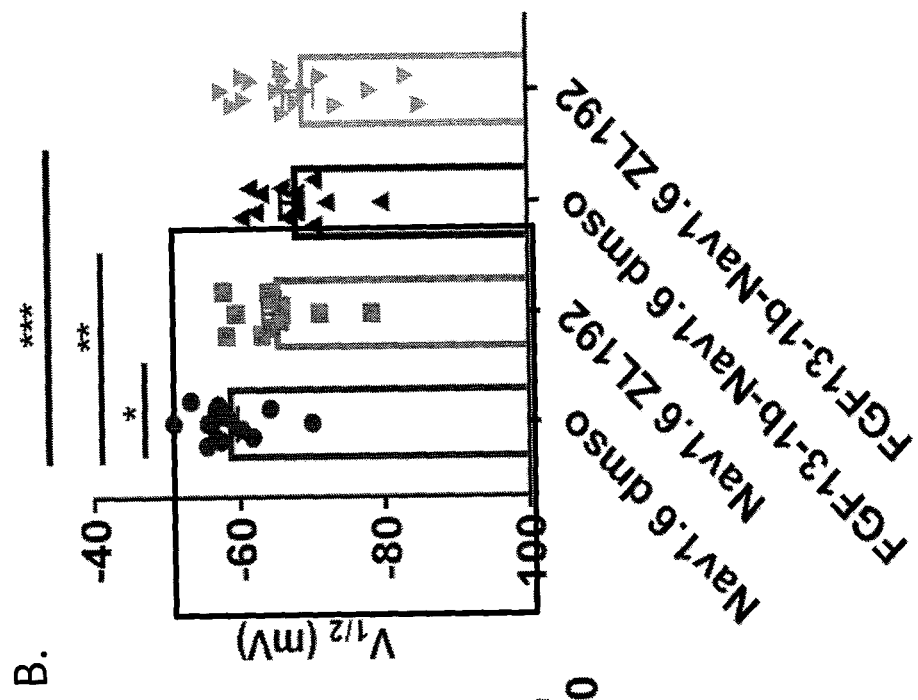
FIGS. 10A-B. Voltage dependence of steady-state inactivation recorded from HEK-Nav1.6 cells transiently expressing (A) FGF13-1b, (C) FGF13-1a in the presence of 30 µM ZL192 or DMSO with Boltzmann fitting. (B) and (D) Bar graphs of V1/2. Data are represented as mean±SEM. $p<0.05$ with ANOVA Bonferroni's multiple comparisons and Holm-Sidak's test. n=8-17 cells per group.
Figure 10A:
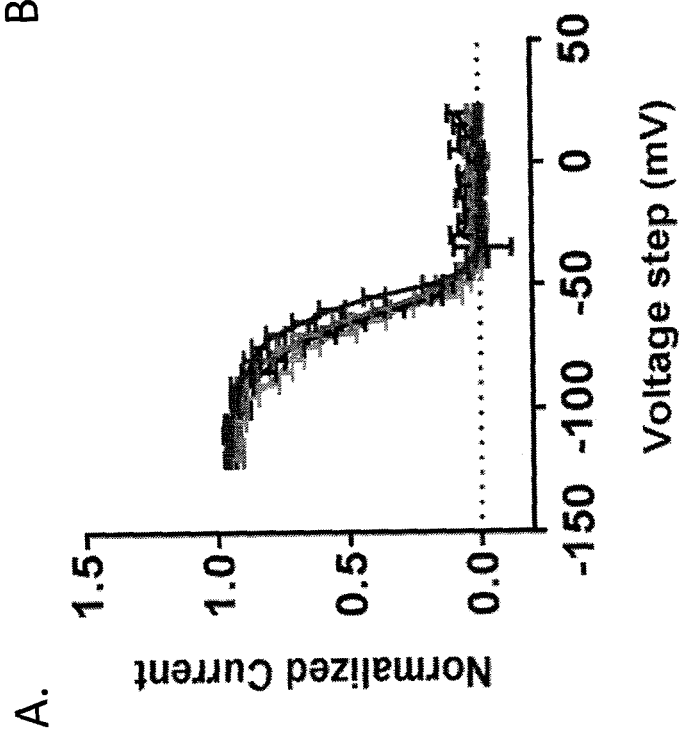
Figure 10B:
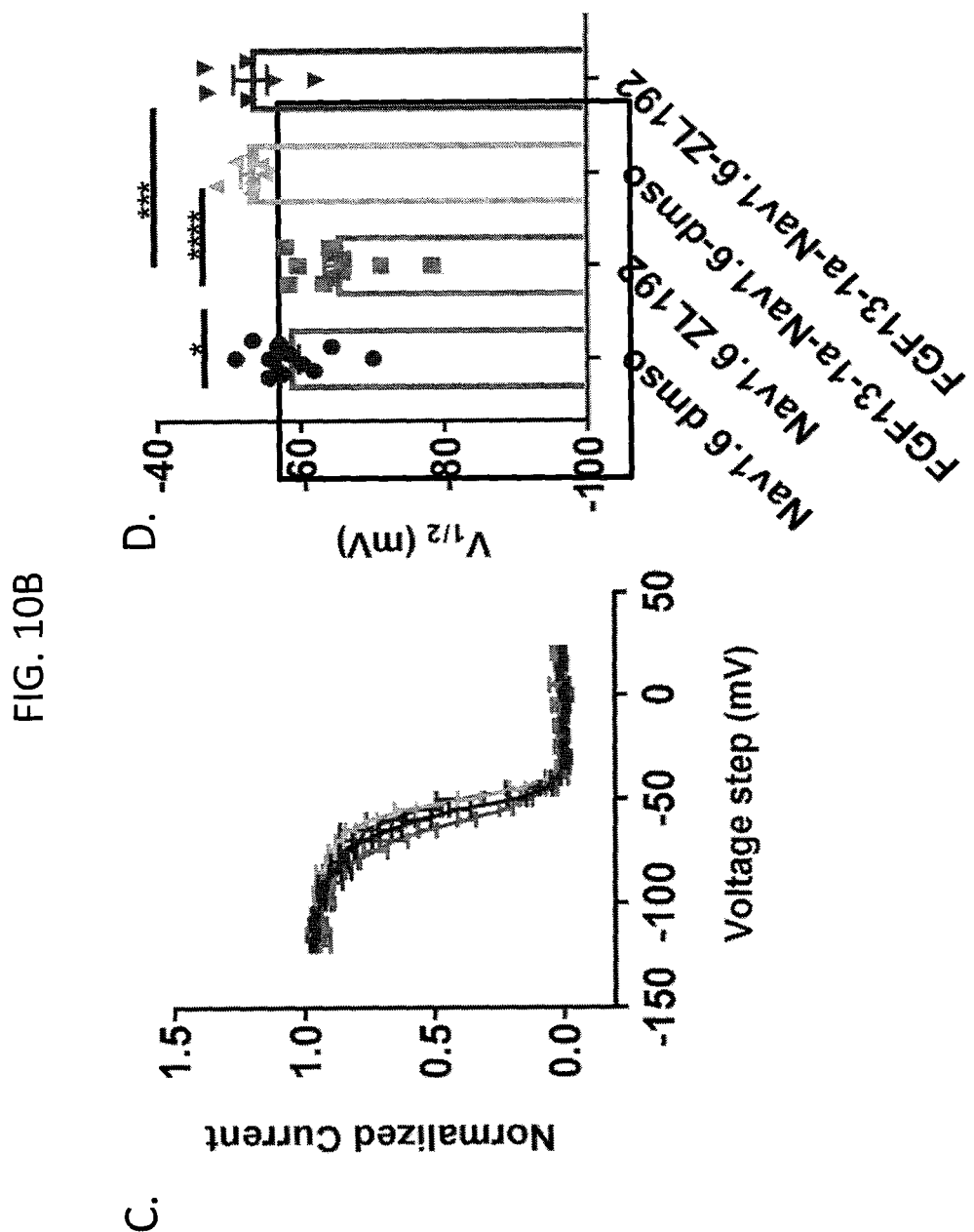
Figure 11:
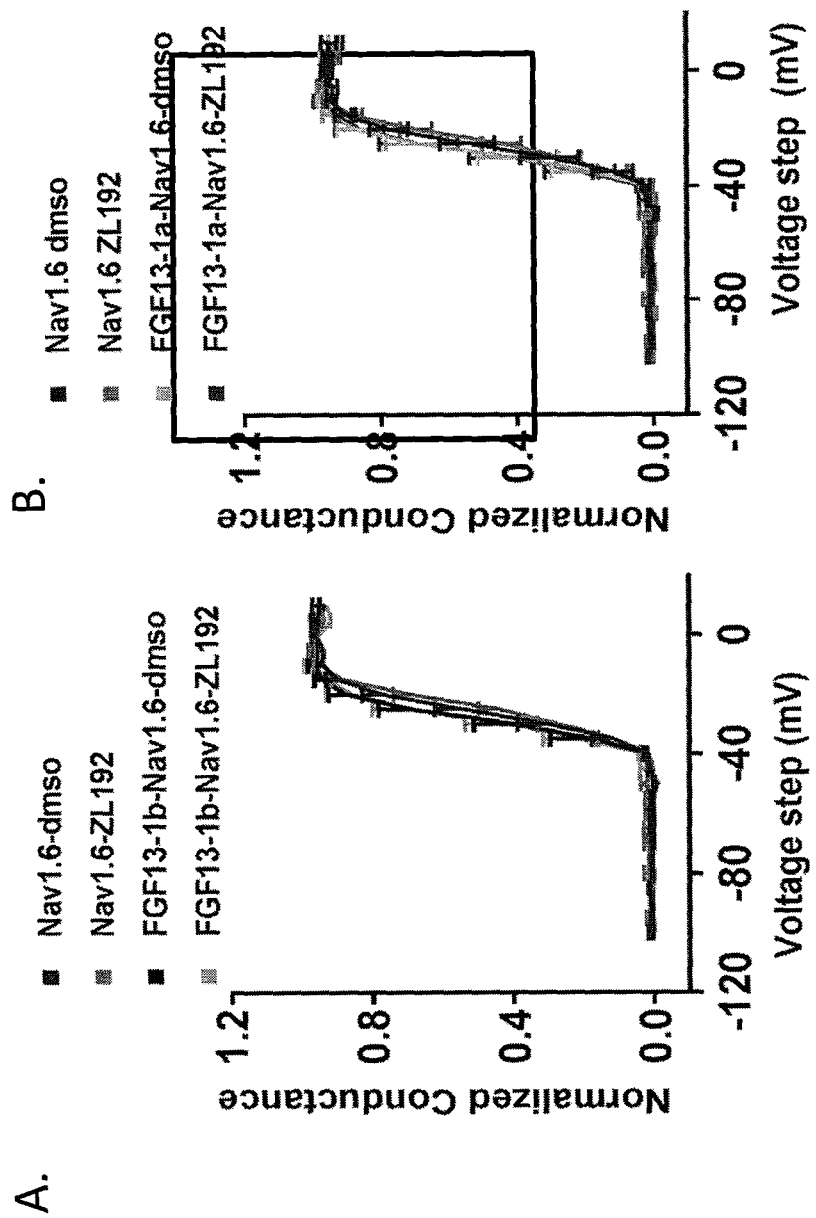
FIGS. 11A-B. Voltage dependence of inactivation recorded from HEK-Nav1.6 cells transiently expressing (A) FGF13-1b, (B) FGF13-1Nav1.6 in the presence of 30 µM ZL192 or DMSO with Boltzmann fitting. n=8-17 cells per group.

It is known in the art that nucleus accumbens plays a critical role in reinforcement-associated learning and in addiction-related behavior. See e.g., Woodruff-Pak, D. S., et al., Behavioral neuroscience 120:229-240 (2006); McKinney, B. C., et al., Genes, brain, and behavior 7:629-638 (2008). It has been shown that Nav1.6 channels are expressed at the nucleus accumbens medium spiny neurons. Shah, B. S., et al., The Journal of Physiology 534(Pt 3):763-776 (2001). The effect of ZL0181 on neuronal firing along with active and passive properties was tested using whole-cell patch clamp techniques in brain tissue slices. Nucleus accumbens medium spiny neurons (MNS) were treated with either DMSO (0.05×) or ZL0181 (50 μM) for one hour in an incubation chamber before being transferred to submerge experimental chamber perfused with oxygenated artificial cerebrospinal fluid for patch clamp experiments. Treatment of MSNs with ZL0181 significantly was found to reduce the number of spikes evoked by rectangular current steps of 10 pA increments compared to DMSO control (FIG. 4A). Input-output curves revealed that the effect of ZL0181 persists across wide spectrum of injected currents (FIG. 4B, Chart C). For instance, at current step of 150 pA the number of spikes in DMSO treated MSNs was 18.4±1.3, n=8 versus 6.9±2.3, n=10 in ZL0181 treated MSNs; $p<0.005$ with Student t-test (FIG. 4B, Chart C). To test the mechanisms underlying neuronal firing reduction and related to sodium channels activity, action potential voltage and current thresholds were measured. Treatment with ZL0181 was found to significantly increase both voltage threshold (−35.9±2.3 mV for DMSO treated MSNs, n=8 versus −27.8±2 mV for ZL0181 treated MSNs, n=10; $p<0.05$ with Student t-test) and current threshold (72.5±11.5 pA for DMSO treated MSNs, n=8 versus 135.8±12.5 pA for ZL0181 treated MSNs, n=10; $p<0.01$ with Student t-test) in MSNs compare to DMSO control (FIG. 4B, Chart D and FIG. 4C, Chart E). Further analysis of neuronal active and passive properties revealed no significant changes in MSN treated with ZL0181 compare to DMSO control. In conclusion, treatment with ZL0181 was found to suppress intrinsic excitability in medium spiny neurons of nucleus accumbens.

Example 3. Methods, Generally

Plasmids.

The CLuc-FGF14, CD4-Nav1.6-NLuc, FGF14-GFP, GFP, and pGL3 expressing full-length Firefly (Photinus pyralis) luciferase fusion constructs were engineered and characterized previously. See e.g., Shavkunov, A., et al. Assay and drug development technologies 10(2):148-160 (2012).

Cell Culture and Transient Transfections.

HEK-Nav1.1, HEK-Nav1.1 and HEK-Nav1.6 were maintained in medium composed of equal volumes of DMEM and F-12 (Invitrogen) supplemented with 0.05% glucose, 0.5 mm pyruvate, 10% fetal bovine serum, 100 units/ml penicillin, 100 µg/ml streptomycin incubated at 37° C. with 5% $CO_2$. For selection of Nav1.1 and Nav1.2, 500 µg/ml G418 (Invitrogen) was used, and for selection of Nav1.6, 80 µg/ml G418 (Invitrogen) was used. Cells were transfected according to manufacturer's instructions at 90-100% confluency using Lipofectamine 2000 (Invitrogen). See e.g., Shavkunov, A., et al. Assay and drug development technologies 10(2):148-160 (2012).

Split-Luciferase Complementation Assay (LCA) and Data Analysis.

Detailed methods for LCA can be found is known in the art. See e.g., Shavkunov A. S., et al., Methods in Molecular Biology 1278:497-514 (2015). Statistical values were calculated as mean and standard error of the mean (mean±SEM), unless otherwise specified. The statistical significance (*$p<0.05$) of different groups was determined by Student's t-test, one-way ANOVA with post-hoc Bonferroni's method or Kruskal-Wallis one-way ANOVA on ranks with post-hoc Dunn's method using Sigma Stat (San Jose, Calif.) and Graph PrismR (La Jolla, Calif.) software. Dose-response modulation was determined by:

$$y = START + (END - START) * x^n / (k^n + x^n)$$

where k, Michaelis constant; n, cooperative sites; x, independent variable; y, dependable variable.

Graphs were plotted in Origin 8.6 Software (Origin Lab Corporation, Northampton, Mass.).

In Vitro Electrophysiology Experiments and Data Analysis.

Detailed methods for path-clamp experiments is known in the art. See e.g., Ali, S. R., et al., Journal of Biological Chemistry 291:11268 (2016).

Protein Expression and Purification.

Detailed methods for protein expression and purification is known in the art. See e.g., Ali, S. R., et al., Journal of Biological Chemistry 291:11268 (2016).

Surface Plasmon Resonance Spectroscopy. SPR experiments were performed on a Biacore T100 instrument (Biacore GE), and the interaction between FGF14 to Nav1.6 channel was studied at 25° C. To analyze the effects of ZL0181 on channel binding, FGF14WT and Nav1.6 C-tail were immobilized using acetate 5.5 with amine coupling kit on CM5 sensor chip, and obtaining RU 3000 and 4500 respectively. No protein was coupled to the control flow channel of the chip. ZL0181 (5-200 µM) in HBS-P+(50 µl/min) buffer (100 mM HEPES, 150 mM NaCl, 0.005% (v/v) P20), pH 7.4 were injected over the chip for 180 s. Next, HB S-P+ buffer without protein were passed over the chip for 180 s to monitor dissociation, and the chip surface was then regenerated with NaCl (200 mM). For each injection of ZL0181 binding to the FGF14WT or the Nav1.6, the nonspecific responses were subtracted from the responses obtained for control prior to data analysis. Maximal equilibrium responses were plotted against the concentrations of ZL0181, and the equilibrium dissociation constant (KD) was calculated from the fitted saturation binding curve. Fitted binding curves were judged to be accurate based on the distribution of the residuals (even and near zero). Graphs were plotted in GraphPad Prism 6 Software (La Jolla, Calif.).

Homology Model of the FGF14:Nav1.6 Complex.

Detailed methods for the FGF14:Nav1.6 complex homology model is known in the art. See e.g., Ali, S. R., et al., Journal of Biological Chemistry 291:11268 (2016).

In Silico Docking of Compound ZL0181.

Docking was performed with Schrödinger Small-Molecule Drug Discovery Suite using the FGF14:Nav1.6 homology model. ZL0181 was prepared with LigPrep, and the FGF14:Nav1.6 complex was prepared with Protein Preparation Wizard. Grids on docking surface were generated with Glide Grid Generator. The docking center was selected at the coordination of X=14.566, Y=−11.536, Z=−12.008. Docking was performed with Glide Ligand Docking using SP-Peptide mode and the top pose with a docking score of −2.223 was selected.

Ex Vivo Electrophysiology Experiments and Data Analysis.

Coronal nucleus accumbens slices were prepared from FGF14−/− or wild type mice either treated with ZL0181 or vehicle control. Evoked action potentials were recorded in regular ASCF solution at 30-31° C. using Axopatch 200B and 700B amplifiers (Molecular Devices, Union City, Calif.). Recordings were filtered at 2 kHz and digitized at 10-20 kHz using a Digidata 1320 analog-to-digital interface and pClamp9 acquisition software (Molecular Devices, Union City, Calif.). Patch pipettes (4-6 MΩ) were prepared from borosilicate glass using a Narishige PC-10 vertical puller (Narishige International Inc., East Meadow, N.Y.). The extracellular bath solution contained (in mM) 130 NaCl, 3.5 KCl, 10 glucose, 1.5 $MgCl_2$, 1.4 $CaCl_2$, 23 $NaHCO_3$, 1.25 $NaH_2PO_4$, osmolarity 300-310, pH 7.4, and the intracellular recording solution contained (in mM) 120 CH3KO3S, 10 KCl, 10 HEPES, 10 glucose, 2 MgCl2, 0.5 EGTA, 2 MgATP, and 0.5 NaGTP, osmolarity 280-290, pH 7.3. Upon forming a whole-cell connection, artificial cerebrospinal fluid containing 10 µM bicuculline (Tocris Bioscience), 30 µM NBQX (Tocris Bioscience), and 100 µM D-APV (Tocris Bioscience) was perfused into the bath solution in order to block synaptic transmission.

After seal formation and membrane rupture, action potential trains were evoked with current step protocol injections of 10 pA increment.

Example 3. In Cell Validation of Compounds of the Invention

Figure 2A:
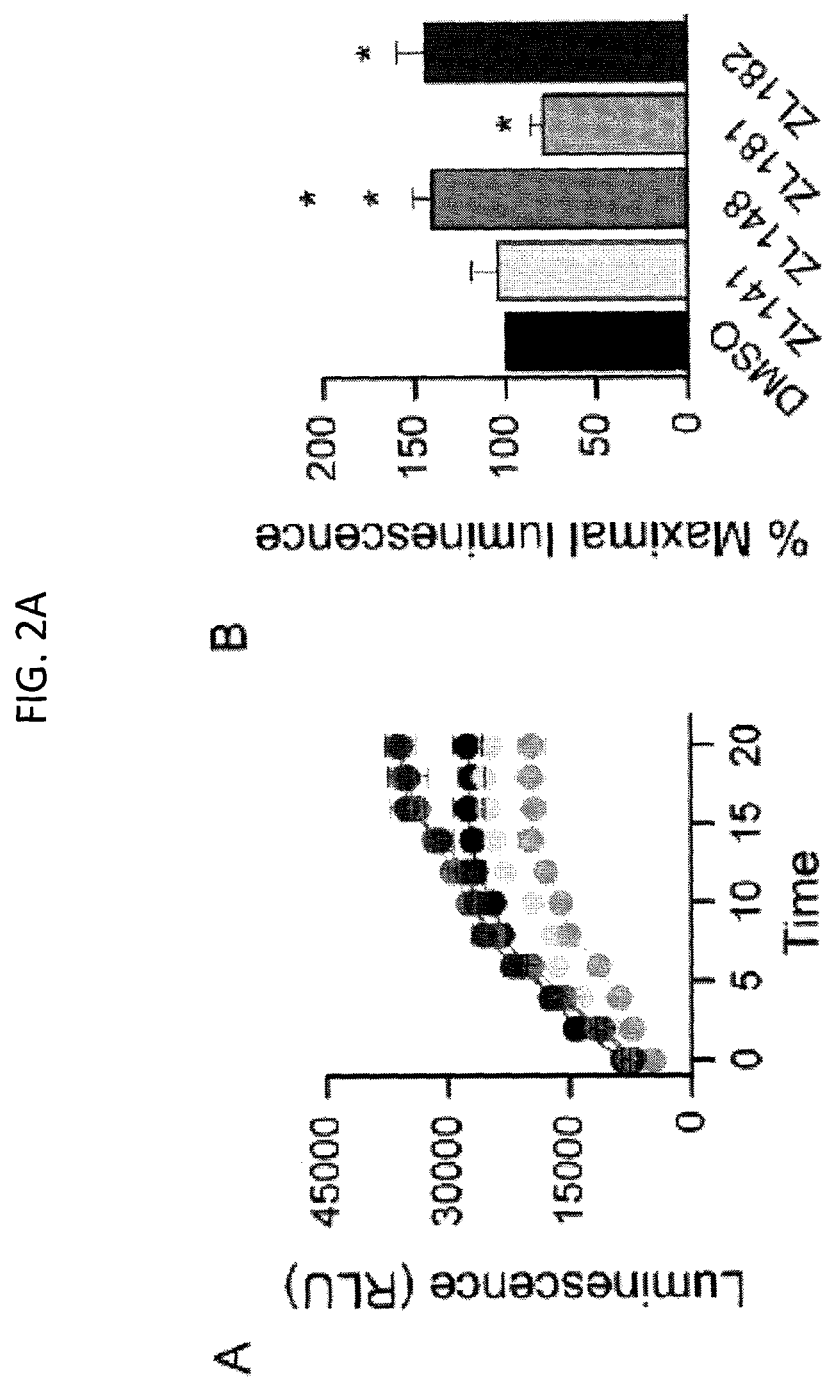
FIGS. 2A-E. Validation of peptidomimetics against the FGF14:Nav1.6 complex, as exemplified using certain compounds of the invention.
Figure 2B:

To monitor the role of compounds of the invention in the FGF14:Nav1.6 complex, certain embodiments of the invention were screened by split-luciferase complementation assay (LCA) where FGF14 and the C-tail of Nav1.6 channels are fused to vectors expressing CLuc and NLuc luciferase reporter. Compounds of the invention, as exemplified by, compounds ZL0141, ZL0148, ZL0181, and ZL0182 (see FIG. 1) were tested at 50 µM in HEK293 cells expressing CLuc-FGF14 and CD4:Nav1.6-NLuc. The changes of luminescence response were observed in the presence of ZL0141 (103±14%, n=5, p>0.05), ZL0148 (132±9%, n=9, *p<0.001, Student's t test), ZL0181 (75±6%, n=9, *p<0.001, Student's t test), and ZL0182 (129±13%, N=9, **p<0.001, Student's t test) compared to control (DMSO, 0.5X) (FIG. 2 A-B). None of the tested compounds interfered with the full-length luciferase enzyme (FIG. 2B, Chart C). Dose-response studies were then performed with compounds ZL0148, ZL0181, and ZL0182 against the FGF14:Nav1.6 complex. Out of the compounds tested, ZL0181 was identified to show dose-response inhibition against the FGF14:Nav1.6 interaction (IC50=63 µM) (FIG. 2B, Chart D).

Figure 2C:
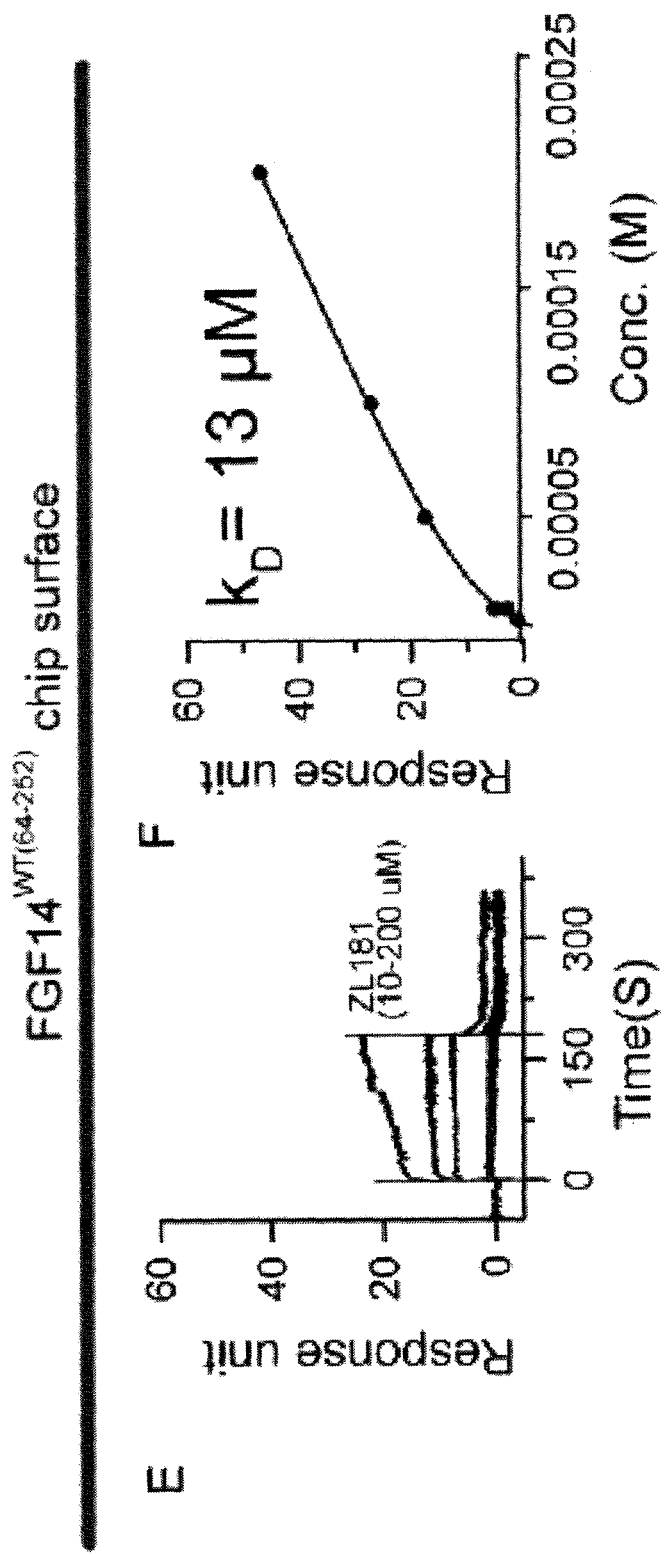
Figure 2D:
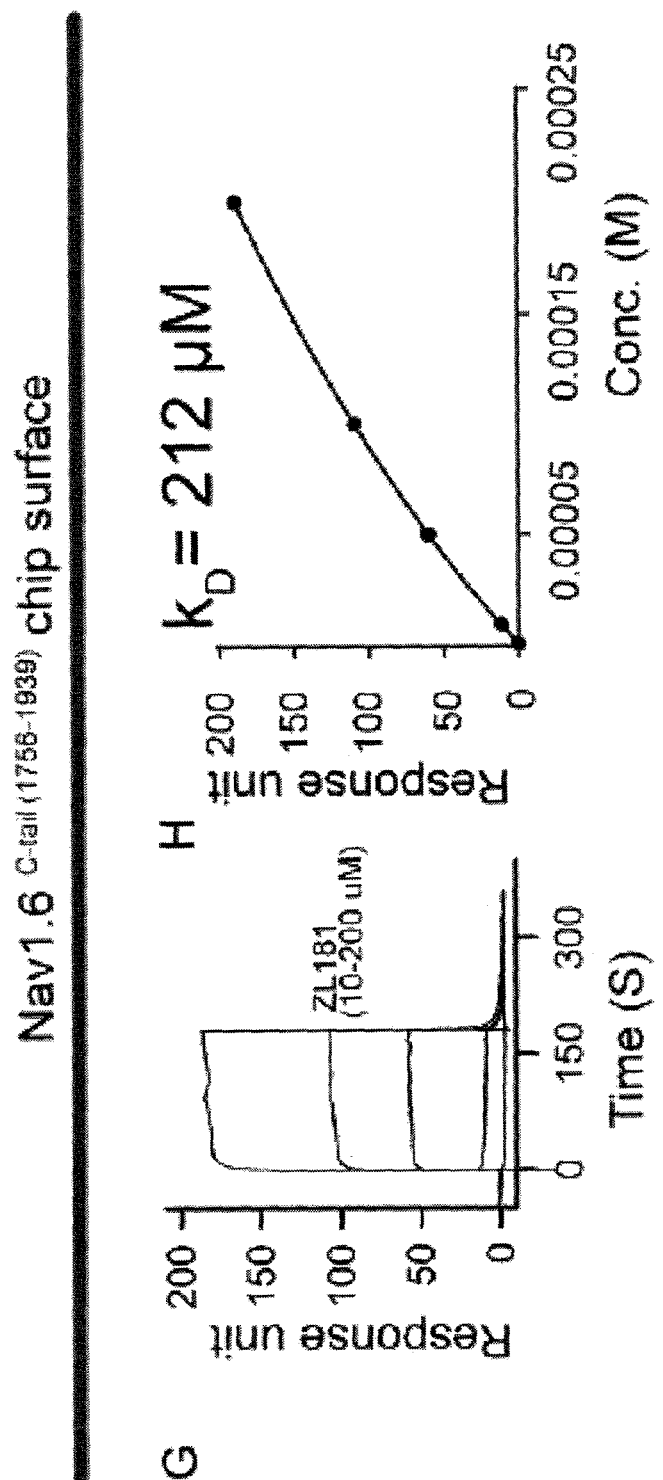
Figure 2E:
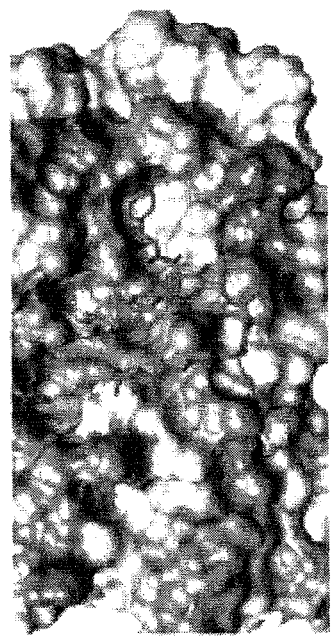
Figure 2E:

The role of ZL0181 was further determined by surface plasmon resonance spectroscopy. To determine the affinity of the ZL0181 to Nav1.6 and FGF14, fixed amount of individual protein was immobilized to a C5 sensor chip surface, and ZL0181 was flowed over the chip surface at different concentration (10-200 µM). The sensogram and fitted saturation binding curve of the ZL0181 to the Nav1.6 and FGF14 is shown in FIG. 2C. The Kd value for FGF14 is lower (13 µM) than that for Nav1.6 (212 µM), indicating that the ZL0181 has a higher affinity to FGF14 protein compared to Nav1.6 C-tail. The data is also consistent with in silico docking results by Schrödinger Small-Molecule Drug Discovery Suite. By using the peptide docking program, ZL0181 can be well docked at the interface of the FGF14:Nav1.6 complex where ZL0181 interacts with key residues R83, E156 and T194 of FGF14 and N1833, L1854, R1854, R1892 of Nav1.6 channels (FIG. 2E, Charts I and J).

Example 4. Synthesis of Compounds of Formula I

Preparation of certain compounds of Formula I, are exemplified by the following syntheses.

Boc-Phe-Leu-Pro-Lys(Fmoc)-OMe (ZL0173)

To a solution of Boc-Phe-OH (838 mg, 3.16 mmol) and ZL0171 (1.25 g, 2.11 mmol) in 20 mL DCM, HBTU (2.4 g, 6.3 mmol), HOBt (285 mg. 2.11 mmol) and DIEA (1361 mg, 10.55 mmol) were added. The mixture was stirred at rt. for 18 hrs. The mixture was washed with 1N NaHSO$_4$, saturated NaHCO$_3$ and Brine. After drying over anhydrous Na$_2$SO$_4$, the solution was concentrated and purified with silica gel column (CHCl$_3$/CH$_3$OH=50/1 to 20/1) to obtain ZL0173 (1.44 g, 81%) as a white foam. $^1$H NMR (300 MHz, CDCl$_3$) δ 8.66 (d, J=8.4 Hz, 0.53H), 7.78 (t, J=6.3 Hz, 2H), 7.62 (d, J=7.1 Hz, 2H), 7.41 (dd, J=13.6, 6.7 Hz, 2H), 7.33 (t, J=7.2 Hz, 2H), 7.25-7.04 (m, 5H), 6.87 (s, 0.51H), 6.69 (s, 0.57H), 5.42 (d, J=9.0 Hz, 1H), 4.87 (s, 1H), 4.70-4.19 (m, 6H), 3.87 (dd, J=15.0, 6.5 Hz, 1H), 3.80-3.68 (m, 3H), 3.63 (m, 1H), 3.36-3.03 (m, 3H), 2.89 (m, 1H), 2.32-1.81 (m, 6H), 1.76-1.43 (m, 7H), 1.34 (d, J=11.5 Hz, 9H), 1.02-0.83 (m, 6H). $^{13}$C NMR (75 MHz, Chloroform-d) δ 172.88, 172.71, 172.61, 172.00, 171.86, 171.25, 171.05, 144.07, 141.34, 129.54, 129.35, 128.32, 128.07, 127.68, 127.05, 126.34, 125.14, 119.97, 77.28, 67.32, 66.59, 60.76, 59.89, 55.23, 52.45, 52.29, 51.84, 49.06, 47.64, 47.27, 31.67, 28.61, 28.27, 25.37, 24.49, 23.40, 21.80, 21.54. ESI-MS (M+H)$^+$ m/z 840.5. HR ESI-MS (M+H)$^+$ m/z=840.4550 (calcd for C$_{47}$H$_{62}$N$_5$O$_9$: 840.4548).

H-Phe-Leu-Pro-Lys(Fmoc)-OMe (ZL0175)

To a solution of ZL0173 (1.38 g, 1.64 mmol) in 4 mL DCM, 2.0 mL TFA was added. The mixture was allowed to stir at rt. for 2 hrs. Then the solution was concentrated to get the crude product ZL0175 (1.4 g, quant.) as a white solid. $^1$H NMR (300 MHz, CDCl$_3$) δ 7.78 (d, J=6.7 Hz, 2H), 7.60 (d, J=4.4 Hz, 2H), 7.41 (t, J=7.3 Hz, 2H), 7.35-7.30 (m, 2H), 7.27-7.00 (m, 5H), 5.44 (s, 1H), 4.81 (m, 1H), 4.63-4.20 (m, 5H), 3.89 (m, 1H), 3.75 (d, J=6.4 Hz, 3H), 3.62 (m, 1H), 3.29-3.09 (m, 3H), 2.70 (m, 1H), 2.10 (m, 8H), 1.77-1.32 (m, 8H), 1.04-0.85 (m, 6H). $^{13}$C NMR (75 MHz, CDCl$_3$) δ 172.56, 171.01, 143.98, 141.30, 129.29, 128.63, 127.69, 127.05, 125.11, 119.98, 77.26, 66.58, 60.01, 52.37, 52.04, 48.73, 47.50, 47.31, 41.55, 40.48, 38.61, 31.65, 29.10, 25.19, 24.67, 23.30, 22.13, 21.86. ESI-MS (M+H)$^+$ m/z 740.4. HR ESI-MS (M+H)$^+$ m/z=740.4022 (calcd for C$_{42}$H$_{54}$N$_5$O$_7$: 740.4023).

Ac-Phe-Leu-Pro-Lys(Fmoc)-OMe (ZL0177)

To a solution of ZL0175 (968 mg, 1.31 mmol) in 5 mL DCM, Et$_3$N (662 mg, 6.54 mmol) and CH$_3$COCl (308 mg, 3.93 mmol) were added. The mixture was stirred at rt. for overnight. The solution was washed with 1N NaHSO$_4$, saturated NaHCO$_3$ and Brine. After drying over anhydrous Na$_2$SO$_4$, the solution was concentrated and purified with silica gel column (CHCl$_3$/CH$_3$OH=50/1 to 20/1) to obtain ZL0177 (930 mg, 91%) as a white foam. $^1$H NMR (300 MHz, CDCl$_3$) δ 8.58 (d, J=8.6 Hz, 0.57H), 7.79 (t, J=6.6 Hz, 2H), 7.61 (d, J=7.4 Hz, 2H), 7.42 (dd, J=13.4, 6.5 Hz, 2H), 7.33 (t, J=6.9 Hz, 2H), 7.19-7.00 (m, 5H), 6.89 (t, J=4.7 Hz, 0.55H), 6.71 (d, J=8.1 Hz, 0.57H), 6.45 (m, 1H), 5.04-4.79 (m, 2H), 4.61 (s, 1H), 4.49-4.17 (m, 4H), 3.92-3.80 (m, 1H), 3.74 (d, J=14.1 Hz, 3H), 3.69-3.57 (m, 1H), 3.13 (m, 3H), 2.93 (dd, J=14.0, 7.7 Hz, 1H), 2.27-1.96 (m, 5H), 1.89 (d, J=10.2 Hz, 3H), 1.70-1.26 (m, 8H), 1.02-0.81 (m, 6H). $^{13}$C NMR (75 MHz, CDCl$_3$) δ 172.69, 171.49, 171.08, 169.64, 143.97, 141.35, 129.44, 129.24, 128.26, 128.11, 127.77, 127.10, 126.54, 124.99, 120.02, 77.26, 67.25, 66.58, 60.72, 59.87, 53.78, 52.46, 51.89, 49.11, 47.66, 47.23, 41.09, 40.40, 38.70, 31.57, 28.66, 25.33, 24.47, 23.36, 23.12, 21.87, 21.61. ESI-MS (M+H)$^+$ m/z 782.4. HR ESI-MS (M+H)$^+$ m/z=782.4125 (calcd for C$_{44}$H$_{56}$N$_5$O$_8$: 782.4129).

Ac-Phe-Leu-Pro-Lys(Fmoc)-OH (ZL0182)

To a solution of ZL0177 (600 mg, 0.77 mmol) in 10 mL CH$_3$OH at 0° C., LiOH.H$_2$O (162 mg, 3.85 mmol) in 4 mL H$_2$O was added. The solution was allowed to stir at 0° C. for 1 hr, and then acidated to pH=3 by 1N NaHSO$_4$. The mixture was extracted by DCM and the organic layer was dried over Na$_2$SO$_4$. After concentration, ZL0182 (536 mg, 91%) was obtained as a white foam. $^1$H NMR (300 MHz, MeOD) δ 8.20 (dd, J=19.0, 7.6 Hz, 1H), 7.79 (d, J=7.5 Hz, 2H), 7.63 (d, J=6.9 Hz, 2H), 7.39 (t, J=7.3 Hz, 2H), 7.31 (d, J=7.3 Hz, 2H), 7.21 (m, 5H), 4.78-4.63 (m, 2H), 4.54-4.30 (m, 4H), 4.18 (t, J=6.6 Hz, 1H), 3.75 (m, 2H), 3.68-3.57 (m, 1H), 3.12 (dd, J=14.0, 5.0 Hz, 2H), 2.88-2.79 (m, 1H), 2.25-2.14 (m, 1H), 2.12-1.97 (m, 2H), 1.94-1.82 (m, 6H), 1.72 (dd, J=13.3, 6.8 Hz, 2H), 1.64-1.56 (m, 2H), 1.49 (s, 3H), 0.96 (d, J=5.8 Hz, 6H). ESI-MS (M+Na)⁺ m/z 790.4. HR ESI-MS (M+Na)⁺ m/z=790.3787 (calcd for C₄₃H₅₃N₅O₈Na: 790.3792).

Ac-Phe-Leu-Pro-Lys(Fmoc)-morpholine (ZL0183)

To a solution of ZL0182 (80 mg, 0.1 mmol) and morpholine (17.4 mg, 0.2 mmol) in 5 mL DCM, HBTU (114 mg, 0.3 mmol), HOBt (14 mg, 0.1 mmol) and DIEA (64.5 mg, 0.5 mmol) were added at 0° C. The mixture was stirred at rt. for 18 hrs. The mixture was washed with 1N NaHSO₄, saturated NaHCO₃ and brine. After drying over anhydrous Na₂SO₄, the solution was concentrated and purified with silica gel column (CHCl₃/CH₃OH=50/1 to 20/1) to obtain ZL0183 (85 mg, quant.) as a colorless oil. ¹H NMR (300 MHz, CDCl₃) δ 8.61 (d, J=8.6 Hz, 1H), 7.78 (t, J=6.9 Hz, 2H), 7.61 (d, J=7.4 Hz, 2H), 7.42 (t, J=7.3 Hz, 2H), 7.32 (t, J=7.5 Hz, 2H), 7.20-7.04 (m, 6H), 6.81 (d, J=8.5 Hz, 1H), 6.48 (d, J=8.6 Hz, 1H), 4.96-4.72 (m, 3H), 4.45-4.35 (m, 2H), 4.26 (dd, J=13.3, 6.7 Hz, 2H), 3.94-3.82 (m, 1H), 3.76-3.46 (m, 9H), 3.28-3.10 (m, 3H), 2.94 (dd, J=13.9, 7.6 Hz, 1H), 2.25-2.12 (m, 2H), 2.07-1.94 (m, 2H), 1.89 (s, 3H), 1.80-1.37 (m, 9H), 0.92 (dd, J=15.8, 6.5 Hz, 6H).

Ac-Phe-Leu-Pro-Lys(Fmoc)-NHPh (ZL0184)

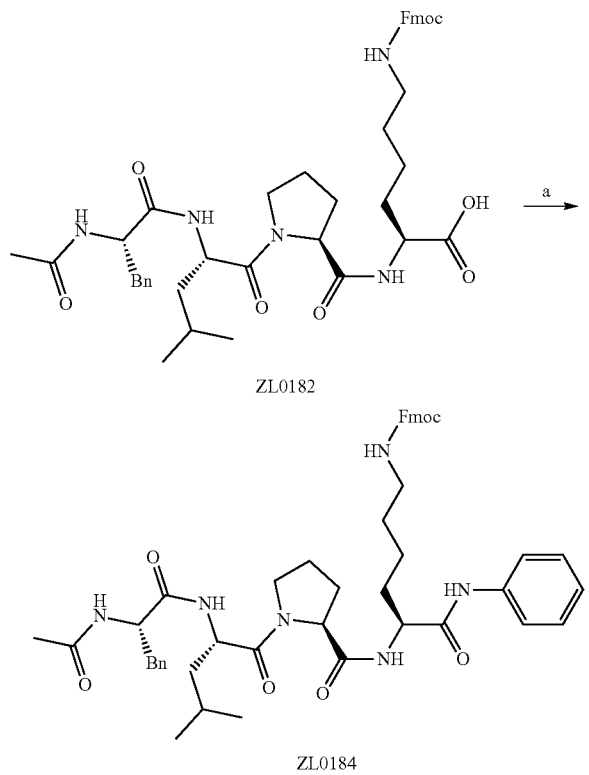

Reagents and conditions:
a aniline, HBTU, HOBt, DIEA, DCM, rt, 90%.

ZL0184 (76 mg, 90%) was synthesized following the procedure of ZL0183. ¹H NMR (300 MHz, CDCl₃) δ 7.78 (d, J=6.9 Hz, 2H), 7.59 (d, J=7.6 Hz, 4H), 7.41 (t, J=7.1 Hz, 2H), 7.32 (m, 3H), 7.17 (m, 7H), 4.94-4.13 (m, 7H), 3.83-2.89 (m, 6H), 2.06 (m, 4H), 1.91 (d, J=12.5 Hz, 3H), 1.86-1.31 (m, 9H), 0.96-0.77 (m, 6H).

Ac-Phe-Leu-Pro-Lys(Fmoc)-NHTz (ZL0185)

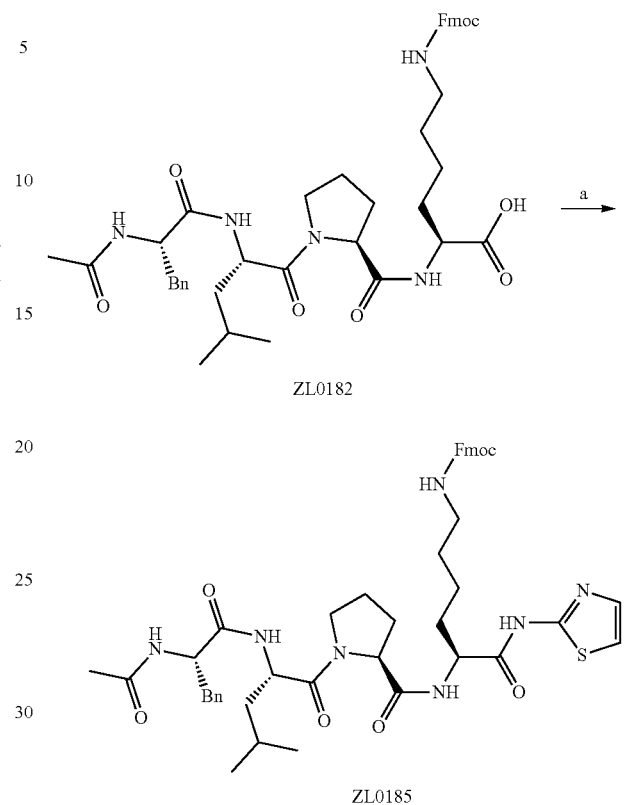

Reagents and conditions:
a thiazol-2-amine, HBTU, HOBt, DIEA, DCM, rt, 94%.

ZL0185 (80 mg, 94%) was synthesized following the procedure of ZL0183. 1H NMR (300 MHz, CDCl3) δ 7.76 (t, J=7.5 Hz, 2H), 7.55 (dd, J=22.6, 5.1 Hz, 3H), 7.44-7.35 (m, 2H), 7.33 (m, 2H), 7.20-6.87 (m, 6H), 6.68 (dd, J=29.3, 8.2 Hz, 1H), 4.90 (m, 3H), 4.63-4.10 (m, 4H), 3.88 (s, 1H), 3.66 (s, 1H), 3.24-2.84 (m, 4H), 2.05 (m, 5H), 1.87 (d, J=9.0 Hz, 3H), 1.78-1.30 (m, 8H), 0.91 (dd, J=17.0, 6.3 Hz, 6H).

Z-Phe-Leu-Pro-Lys(Boc)-NH₂ (ZL0181).

To a solution of ZL0180 (790 mg, 1.55 mmol) and H-Lys(Boc)-NH₂H₂O (436 mg, 1.55 mmol) in 20 mL DCM, HBTU (1762 mg, 4.65 mmol), HOBt (209 mg. 1.55 mmol) and DIEA (1.4 mL, 7.75 mmol) were added. The mixture was stirred at rt. for overnight. The solution was washed with 1 N NaHSO₄, saturated NaHCO₃ and brine. After drying over anhydrous Na₂SO₄, the solution was concentrated and purified with silica gel column (DCM/MeOH=50/1 to 20/1) to obtain ZL0181 (815 mg, 69%) as a white foam. ¹H NMR (300 MHz, MeOD) δ 7.40-7.09 (m, 10H), 5.02 (s, 2H), 4.78-4.25 (m, 4H), 3.85-3.55 (m, 2H), 3.19-2.99 (m, 3H), 2.85 (dd, J=13.8, 9.5 Hz, 1H), 2.24-1.77 (m, 5H), 1.75-1.37 (m, 17H), 0.97 (d, J=6.3 Hz, 6H). ¹³C NMR (300 MHz, MeOD) δ 175.48, 172.84, 172.60, 171.68, 157.10, 156.74, 137.13, 136.77, 129.02, 128.06, 128.01, 127.53, 127.28, 126.34, 78.44, 66.13, 60.17, 56.13, 52.94, 49.50, 47.24, 39.96, 39.81, 37.73, 31.44, 29.11, 28.96, 27.46, 24.63, 24.34, 22.72, 22.38, 20.60. ESI-MS (M+H)⁺ m/z 737.4. HR ESI-MS (M+H)⁺ m/z=737.4224 (calcd for C₃₉H₅₇N₆O₈: 737.4238).

H-Phe-Leu-Pro-Lys(Boc)-NH$_2$ (ZL0186)

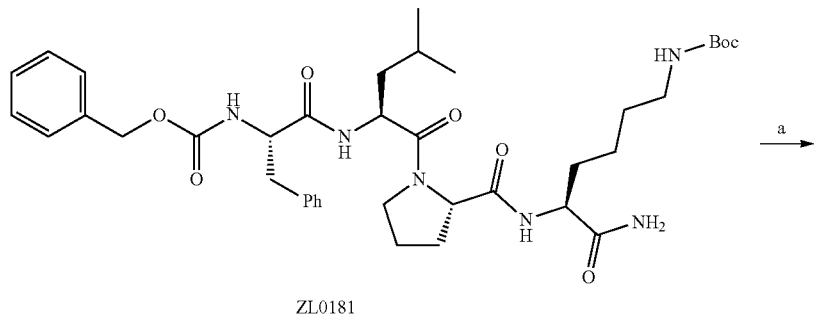

ZL0181

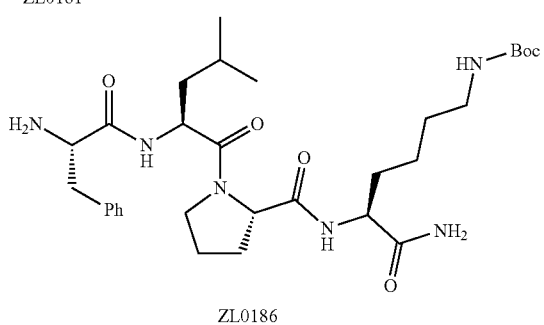

ZL0186

Reagents and conditions:
a 10% Pd/C, CH$_3$OH, H$_2$, rt, 91%.

To a solution of ZL0181 (750 mg, 0.98 mmol) in 10 mL CH$_3$OH, 10% Pd/C (75 mg) was added. Then the mixture was charged H$_2$ and stirred at rt. for overnight. The mixture was filtrated and the filtrate was concentrated to get the crude product. The residue was purified by silica gel column (Hexane/EtOAc=10/1 to 5/1) to obtain ZL0186 (557 mg, 91%) as a white solid. $^1$H NMR (300 MHz, CDCl$_3$) δ 7.87 (d, J=8.3 Hz, 1H), 7.24 (m, 5H), 6.78 (s, 1H), 6.11 (s, 1H), 4.96 (s, 0.49H), 4.74 (s, 1H), 4.52-4.26 (m, 2H), 3.85 (s, 1H), 3.61 (s, 2H), 3.44 (t, J=3.4 Hz, 2H), 3.23-2.97 (m, 3H), 2.78-2.64 (m, 1H), 2.23-1.77 (m, 8H), 1.59 (m, 3H), 1.42 (s, 11H), 0.93 (s, 6H).

Bz-Phe-Leu-Pro-Lys(Boc)-NH$_2$ (ZL0188)

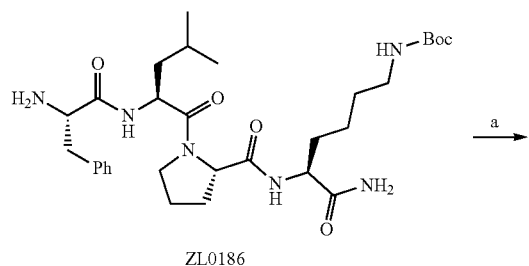

ZL0186

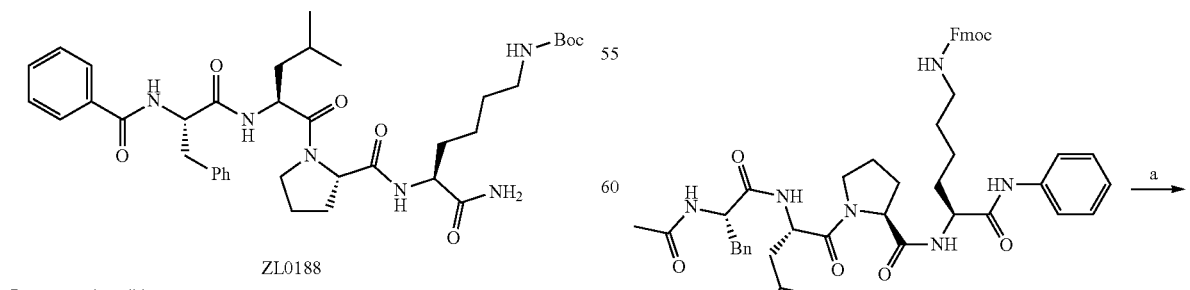

ZL0188

Reagents and conditions:
a benzoyl chloride, Et$_3$N, DCM, rt, 43%.

To a solution of ZL0186 (100 mg, 0.166 mmol) and Et$_3$N (84 mg, 0.83 mmol) in 5 mL DCM, BzCl (70 mg, 0.5 mmol) was added at 0° C. The solution was allowed to stir at rt. for overnight. The solution was washed with 1N NaHSO$_4$, saturated NaHCO$_3$ and brine. After drying over anhydrous Na$_2$SO$_4$, the solution was concentrated and purified with silica gel column (CHCl$_3$/CH$_3$OH=50/1 to 20/1) to obtain ZL0188 (50 mg, 43%) as a colorless oil. $^1$H NMR (300 MHz, CDCl$_3$) δ 8.09 (d, J=7.5 Hz, 1H), 7.76 (s, 2H), 7.66-7.36 (m, 4H), 7.17 (s, 3H), 7.03 (s, 1H), 4.85 (m, 4H), 4.18-3.43 (m, 2H), 3.37-2.90 (m, 4H), 2.42-1.79 (m, 4H), 1.44 (s, 17H), 0.94 (s, 6H).

Ac-Phe-Leu-Pro-Lys-NHPh (ZL0192)

ZL0184

-continued

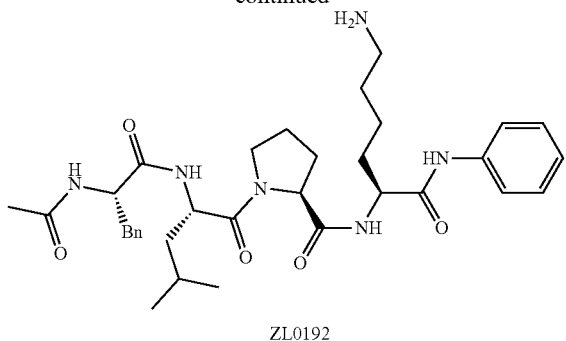

ZL0192

Reagents and conditions:
a piperidine, DCM, rt, 81%.

To a solution of ZL0184 (50 mg, 0.059 mmol) in 3 mL DCM, piperidine (0.5 mL) was added. The solution was stirred at rt. for 1 hr. Then the mixture was concentrated directly and purified by silica gel column (CHCl$_3$/CH$_3$OH=50/1 to 20/1) to obtain ZL0192 (30 mg, 81%) as a white solid.

Example 5. Synthesis of Compounds of Formula II

Preparation of certain compounds of Formula II, are exemplified by the following syntheses.

Z-Phe-Leu-Lys(Boc)-NH$_2$(ZL0142)

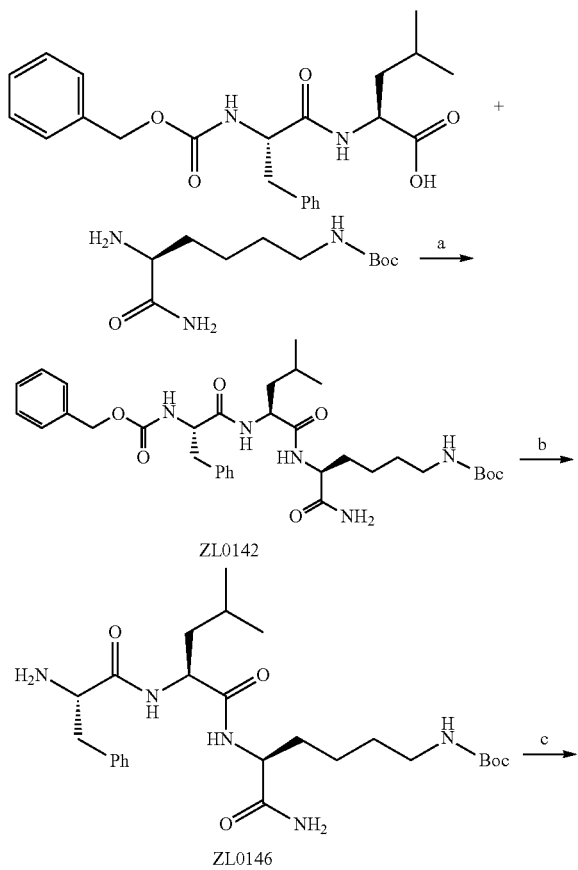

-continued

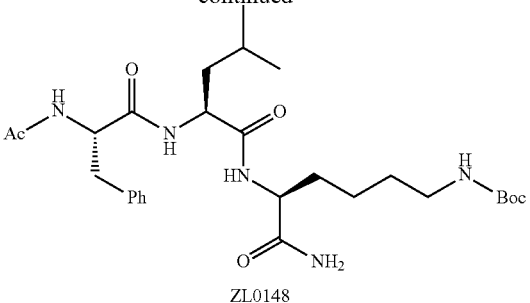

ZL0148

Reagents and conditions:
a HBTU, HOBt, DIEA, DCM, rt, 61%;
b 10% Pd/C, H$_2$, CH$_3$OH, rt, quant.;
c CH$_3$COCl, NEt$_3$, DCM, rt, 29%.

To a solution of Z-Phe-Leu-OH (206 mg, 0.5 mmol) and Lys(Boc)-NH$_2$ (212 mg, 0.75 mmol) in 5 mL DCM, HBTU (569 mg, 1.5 mmol), HOBt (67 mg. 0.5 mmol) and DIEA (323 mg, 2.5 mmol) were added. The mixture was stirred at rt. for 18 hrs. The mixture was washed with 1 N NaHSO$_4$, saturated NaHCO$_3$ and brine. After drying over anhydrous Na$_2$SO$_4$, the solution was concentrated and purified with silica gel column (Hexane/EtOAc=10/1 to 7/1) to obtain ZL0142 (196 mg, 61%) as a light yellow solid. $^1$H NMR (300 MHz, DMSO) δ 8.14 (d, J=8.0 Hz, 0.40H), 7.77 (d, J=8.0 Hz, 0.41H), 7.51 (d, J=8.5 Hz, 0.44H), 7.39-7.28 (m, 5H), 7.27-7.15 (m, 5H), 7.02 (s, 0.59H), 6.74 (t, J=5.3 Hz, 0.51H), 4.94 (s, 2H), 4.41-4.22 (m, 2H), 4.15 (dd, J=7.9, 5.2 Hz, 1H), 3.02 (dd, J=13.8, 3.4 Hz, 1H), 2.87 (m, 2H), 2.73 (m, 1H), 1.62 (m, 2H), 1.56-1.42 (m, 3H), 1.36 (s, 11H), 1.22 (m, 1H), 0.88 (dd, J=13.4, 6.4 Hz, 6H). $^{13}$C NMR (75 MHz, MeOD+CDCl$_3$) δ 175.35, 173.10, 172.98, 157.11, 157.03, 136.99, 136.65, 129.00, 128.07, 127.59, 127.32, 126.38, 66.29, 56.45, 52.93, 52.09, 40.09, 37.43, 31.38, 29.12, 27.45, 24.37, 22.80, 22.14, 20.63. ESI-MS (M+H)$^+$ m/z 640.4. HR ESI-MS (M+H)$^+$ m/z=640.3713 (calcd for C$_{34}$H$_{50}$N$_5$O$_7$: 640.3710).

H-Phe-Leu-Lys(Boc)-NH$_2$ (ZL0146)

To a solution of Z-Phe-Leu-Lys(Boc)-OH (100 mg) in MeOH, 10% Pd/C (10 mg) was added. Under H$_2$, the mixture was allowed to stir at rt. for 2 hrs. The solution was filtrated and the filtrate was concentrated to get the crude product. The residue was purified by silica gel column (Hexane/EtOAc=10/1 to 5/1) to obtain ZL0146 (80 mg, quant.) as a white solid. $^1$H NMR (300 MHz, CDCl$_3$) δ 7.84 (d, J=7.1 Hz, 1H), 7.31 (m, 2H), 7.23-7.13 (m, 3H), 6.73 (s, 1H), 6.08 (s, 1H), 4.96 (s, 1H), 4.44-4.32 (m, 2H), 3.70 (dd, J=8.7, 3.9 Hz, 1H), 3.19 (dd, J=13.7, 3.8 Hz, 1H), 3.08 (m, 2H), 2.79-2.70 (m, 1H), 1.97-1.79 (m, 1H), 1.62 (m, 4H), 1.43 (s, 13H), 0.91 (dd, J=8.8, 6.2 Hz, 6H). ESI-MS (M+H)$^+$ m/z 506.3. HR ESI-MS (M+H)$^+$ m/z=506.3339 (calcd for C$_{26}$H$_{44}$N$_5$O$_5$: 506.3342).

Ac-Phe-Leu-Lys(Boc)-NH$_2$ (ZL0148)

To a solution of H-Phe-Leu-Lys(Boc)-NH$_2$ (43 mg, 0.078 mmol) in 5 mL DCM, Et$_3$N (40 mg, 0.4 mmol) and CH$_3$COCl (19 mg, 0.24 mmol) was added. The mixture was allowed to stir at rt. for overnight. The solution was washed with 1N NaHSO$_4$, saturated NaHCO$_3$ and brine. After drying over anhydrous Na$_2$SO$_4$, the solution was concentrated and purified with silica gel column (Hexane/EtOAc=10/1 to 7/1) to obtain ZL0148 (12 mg, 29%) as a white solid. $^1$H NMR (300 MHz, MeOD) δ 4.63 (s, 2H), 4.44-4.23 (m, 2H), 3.22-2.81 (m, 4H), 1.92 (s, 3H), 1.84 (m, 1H), 1.75-1.59 (m, 4H), 1.44 (s, 13H), 0.95 (dd, J=11.8, 5.9 Hz, 6H). ESI-MS (M+H)$^+$+m/z 548.3. HR ESI-MS (M+H)$^+$ m/z=548.3437 (calcd for C$_{28}$H$_{46}$N$_5$O$_6$: 548.3448).

Z-Phe-Leu-Lys(H)-NH$_2$ (ZL0145)

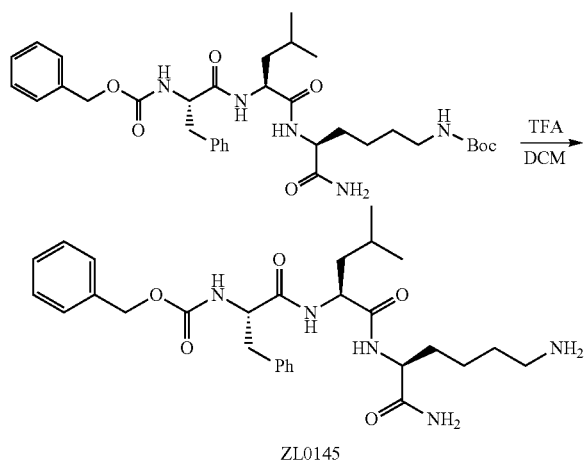

ZL0145

To a solution of Z-Phe-Leu-Lys(Boc)-NH$_2$ (50 mg, 0.078 mmol) in 2 mL DCM, 0.5 mL TFA was added. The mixture was allowed to stir for 2 hrs at rt. Then the solution was concentrated to get the crude product ZL0145 (40 mg, quant.) as a colorless oil. $^1$H NMR (300 MHz, CDCl$_3$) δ 7.81 (s, 1H), 7.46 (s, 2H), 7.34-7.29 (m, 3H), 7.23 (m, 5H), 7.14 (s, 2H), 6.89 (s, 1H), 5.60 (s, 1H), 5.00 (dd, J=30.8, 12.1 Hz, 2H), 4.42 (m, 3H), 3.17-2.91 (m, 4H), 1.82-1.41 (m, 8H), 0.91-0.78 (m, 6H).

Example 6. Synthesis of Compounds of Formula III

Preparation of certain compounds of Formula III, are exemplified by the following syntheses.

Z-Phe-Leu-Pro-NH$_2$ (ZL0141)

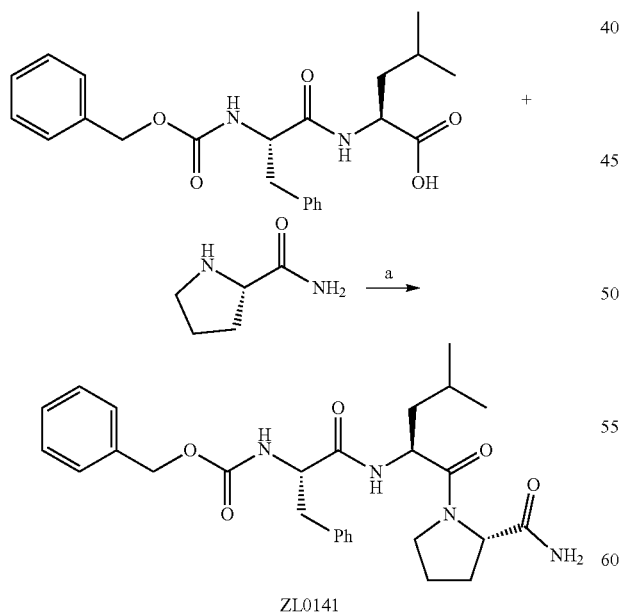

ZL0141

Reagents and conditions:
a HBTU, HOBt, DIEA, DCM, rt, quant.

To a solution of Z-Phe-Leu-OH (206 mg, 0.5 mmol) and Pro-NH$_2$ (86 mg, 0.75 mmol) in 5 mL DCM, HBTU (569 mg, 1.5 mmol), HOBt (67 mg. 0.5 mmol) and DIEA (323 mg, 2.5 mmol) were added. The mixture was stirred at rt. for 18 hrs. The solution was washed with 1 N NaHSO$_4$, saturated NaHCO$_3$ and brine. After drying over anhydrous Na$_2$SO$_4$, the solution was concentrated and purified with silica gel column (Hexane/EtOAc=10/1 to 7/1) to obtain ZL0141 (278 mg, quant.) as a white foam. $^1$H NMR (300 MHz, CDCl3) δ 7.65 (s, 1H), 7.33 (m, 4H), 7.15 (m, 6H), 6.87 (s, 1H), 5.57-5.32 (m, 2H), 5.11-4.96 (m, 2H), 4.86 (d, J=4.8 Hz, 1H), 4.71 (s, 1H), 4.52 (s, 1H), 3.86-3.54 (m, 2H), 3.12-2.89 (m, 2H), 2.22 (m, 2H), 2.01 (s, 2H), 1.55 (m, 3H), 0.93 (dd, J=17.1, 6.2 Hz, 6H). 13C NMR (75 MHz, CDCl$_3$) δ 173.74, 172.10, 170.94, 155.98, 136.48, 136.32, 129.37, 128.48, 128.09, 127.83, 126.79, 66.84, 59.53, 55.48, 49.01, 47.42, 41.63, 39.20, 38.61, 28.27, 25.03, 24.59, 23.28, 21.86. ESI-MS (M+H)$^+$ m/z 509.3. HR ESI-MS (M+H)$^+$ m/z=509.2761 (calcd for C$_{28}$H$_{37}$N$_4$O$_5$: 509.2764)

Z-Phe-Leu-Pro-OMe (ZL0176)

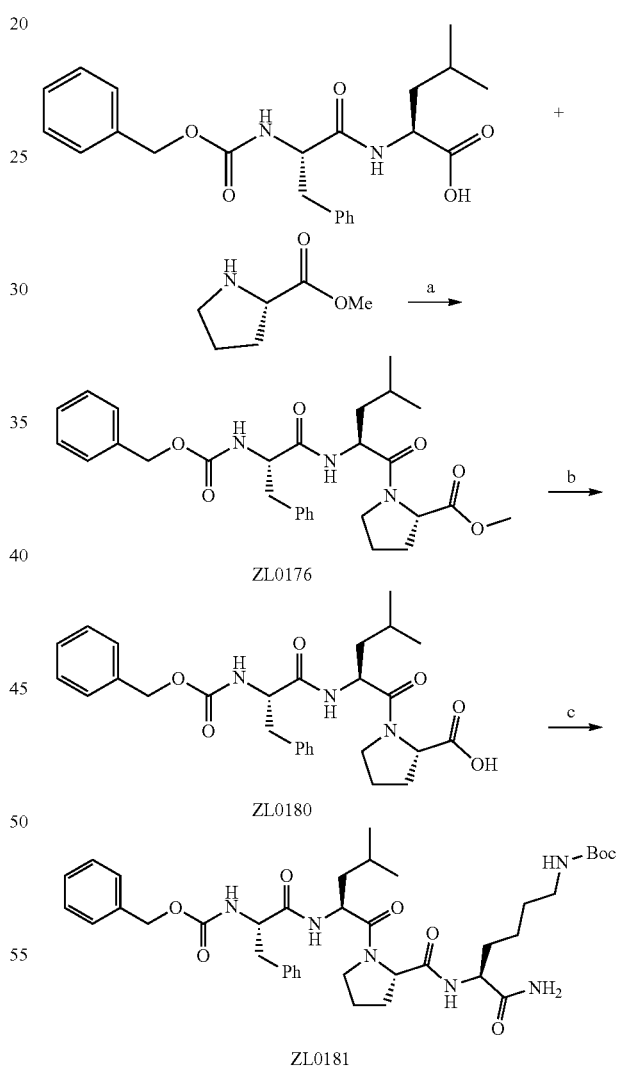

ZL0176

ZL0180

ZL0181

Reagents and conditions:
a HBTU, HOBt, DIEA, DCM, rt, quant.;
b LiOH·H$_2$O, CH$_3$OH/H$_2$O, rt, quant.;
c tert-butyl (S)-(5,6-diamino-6-oxohexyl)carbamate, HBTU, HOBt, DIEA, DCM, rt, 69%.

To a solution of Z-Phe-Leu-OH (1000 mg, 2.43 mmol) and Pro-OMe (483 mg, 2.9 mmol) in 20 mL DCM, HBTU (2700 mg, 7.29 mmol), HOBt (328 mg. 2.43 mmol) and DIEA (1567 mg, 12 mmol) were added. The mixture was stirred at rt. for 18 hrs. The solution was washed with 1 N NaHSO$_4$, saturated NaHCO$_3$ and brine. After drying over anhydrous Na$_2$SO$_4$, the solution was concentrated and purified with silica gel column (DCM/MeOH=100/1 to 50/1) to obtain ZL0176 (1500 mg, quant.) as a white foam. $^1$H NMR (300 MHz, CDCl3) δ 7.39-7.29 (m, 5H), 7.27-7.22 (m, 3H), 7.16 (m, 2H), 6.70 (d, J=8.1 Hz, 1H), 5.31 (d, J=8.2 Hz, 1H), 5.07 (d, J=3.3 Hz, 2H), 4.78 (td, J=8.6, 5.2 Hz, 1H), 4.48 (m, 2H), 3.76 (m, 1H), 3.73 (s, 3H), 3.67-3.58 (m, 1H), 3.08 (d, J=6.1 Hz, 2H), 2.29-2.15 (m, 1H), 2.12-1.94 (m, 3H), 1.70-1.41 (m, 3H), 0.98 (d, J=6.2 Hz, 3H), 0.92 (d, J=6.4 Hz, 3H). $^{13}$C NMR (300 MHz, CDCl$_3$) δ 172.34, 170.74, 170.55, 136.26, 129.38, 128.55, 128.50, 128.12, 128.02, 126.94, 67.02, 58.71, 52.21, 49.07, 46.85, 41.70, 28.98, 24.88, 24.49, 23.26, 21.92. ESI-MS (M+H)$^+$ m/z 524.3. HR ESI-MS (M+H)$^+$ m/z=524.2753 (calcd for C$_{29}$H$_{38}$N$_3$O$_6$: 524.2761).

Z-Phe-Leu-Pro-OH (ZL0180)

To a solution of ZL0176 (1271 mg, 2.43 mmol) in 15 mL CH$_3$OH at 0° C., LiOH.H$_2$O (162 mg, 3.85 mmol) in 5 mL H$_2$O was added. The solution was allowed to stir at 0° C. for overnight, and then acidated to pH=3 by 1N NaHSO$_4$. The mixture was extracted by DCM and the organic layer was dried over Na$_2$SO$_4$. After concentration, ZL0180 (1340 mg, quant.) was obtained as a white foam. $^1$H NMR (300 MHz, CDCl$_3$) δ 7.53-7.30 (m, 5H), 7.25-7.10 (m, 5H), 5.67 (d, J=8.0 Hz, 1H), 5.10 (d, J=2.8 Hz, 2H), 4.80 (dd, J=15.3, 7.1 Hz, 1H), 4.57-4.43 (m, 2H), 3.74 (m, 1H), 3.60 (m, 1H), 3.09 (m, 2H), 2.30-1.98 (m, 4H), 1.55 (m, 3H), 0.94 (d, J=6.1 Hz, 3H), 0.90 (d, J=6.4 Hz, 3H). ESI-MS (M+Na)$^+$ m/z 532.2. HR ESI-MS (M+Na)$^+$ m/z=532.2423 (calcd for C$_{28}$H$_{35}$N$_3$O$_6$Na: 532.2424).

Example 7. Synthesis of Compounds of Formula IV

Preparation of certain compounds of Formula IV, are exemplified by the following syntheses.

Boc-Leu-Pro-Lys(Boc)NH$_2$ (ZL0143)

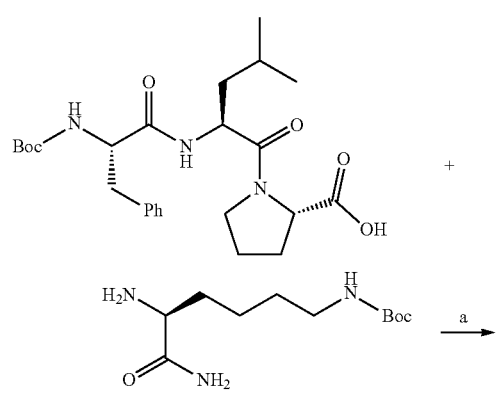

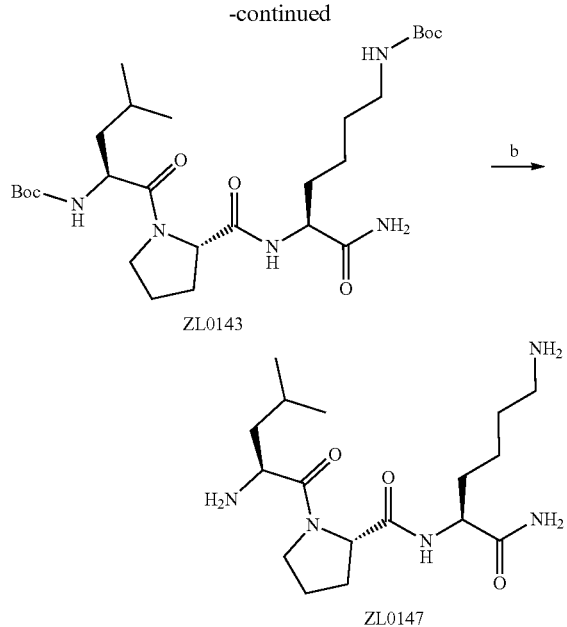

Reagents and conditions:
a HBTU, HOBt, DIEA, DCM, rt, quant.;
b TFA, DCM, rt, quant.

To a solution of Boc-Leu-Pro-OH (230 mg, 0.7 mmol) and Lys(Boc)-NH$_2$ (296 mg, 1.05 mmol) in 5 mL DCM, HBTU (796 mg, 2.1 mmol), HOBt (94 mg. 0.7 mmol) and DIEA (452 mg, 3.5 mmol) were added. The mixture was stirred at rt. for 18 hrs. The mixture was washed with 1 N NaHSO$_4$, saturated NaHCO$_3$ and brine. After drying over anhydrous Na$_2$SO$_4$, the solution was concentrated and purified with silica gel column (Hexane/EtOAc=10/1 to 7/1) to obtain ZL0143 (414 mg, quant.) as a light yellow foam. $^1$H NMR (300 MHz, CDCl3) δ 6.74 (s, 1H), 6.10 (s, 1H), 5.43 (d, J=7.6 Hz, 1H), 5.15 (s, 1H), 4.42 (m, 3H), 3.77 (s, 1H), 3.58 (d, J=7.0 Hz, 1H), 3.07 (d, J=5.6 Hz, 2H), 2.22-1.56 (m, 7H), 1.42 (m, 24H), 0.95 (dd, J=9.5, 6.7 Hz, 6H). $^{13}$C NMR (75 MHz, CDCl$_3$) δ 174.42, 173.34, 171.61, 156.13, 155.82, 79.76, 79.08, 60.39, 52.82, 50.87, 47.39, 41.50, 40.11, 31.47, 29.31, 28.46, 28.36, 28.16, 25.24, 24.65, 23.34, 22.63, 21.59.

Boc-Leu-Pro-Lys(Boc)NH$_2$ (ZL0143)

To a solution of Boc-Leu-Pro-OH (230 mg, 0.7 mmol) and Lys(Boc)-NH$_2$ (296 mg, 1.05 mmol) in 5 mL DCM, HBTU (796 mg, 2.1 mmol), HOBt (94 mg. 0.7 mmol) and DIEA (452 mg, 3.5 mmol) were added. The mixture was stirred at rt. for 18 hrs. The mixture was washed with 1 N NaHSO$_4$, saturated NaHCO$_3$ and brine. After drying over anhydrous Na$_2$SO$_4$, the solution was concentrated and purified with silica gel column (Hexane/EtOAc=10/1 to 7/1) to obtain ZL0143 (414 mg, quant.) as a light yellow foam. $^1$H NMR (300 MHz, CDCl3) δ 6.74 (s, 1H), 6.10 (s, 1H), 5.43 (d, J=7.6 Hz, 1H), 5.15 (s, 1H), 4.42 (m, 3H), 3.77 (s, 1H), 3.58 (d, J=7.0 Hz, 1H), 3.07 (d, J=5.6 Hz, 2H), 2.22-1.56 (m, 7H), 1.42 (m, 24H), 0.95 (dd, J=9.5, 6.7 Hz, 6H). $^{13}$C NMR (75 MHz, CDCl3) δ 174.42, 173.34, 171.61, 156.13, 155.82, 79.76, 79.08, 60.39, 52.82, 50.87, 47.39, 41.50, 40.11, 31.47, 29.31, 28.46, 28.36, 28.16, 25.24, 24.65, 23.34, 22.63, 21.59.

H-Leu-Pro-Lys(H)-NH$_2$ (ZL0147)

To a solution of Boc-Leu-Pro-Lys(Boc)-NH$_2$ (374 mg, 0.63 mmol) in 4 mL DCM, 1.0 mL TFA was added. The mixture was allowed to stir for 2 hours at rt. Then the solution was concentrated to get the crude product ZL0147 (240 mg, quant.) as a yellow foam. ¹H NMR (300 MHz, MeOD) δ 4.51 (m, 1H), 4.34 (dd, J=9.0, 4.8 Hz, 1H), 4.27-4.17 (m, 1H), 3.80-3.69 (m, 1H), 3.59 (m, 1H), 2.97 (t, J=6.9 Hz, 2H), 2.28 (m, 1H), 2.18-1.95 (m, 3H), 1.92-1.80 (m, 2H), 1.78-1.68 (m, 4H), 1.53 (dd, J=16.5, 9.3 Hz, 2H), 1.38 (dd, J=6.0, 3.3 Hz, 1H), 1.09-0.93 (m, 6H).
Boc-Leu-Pro-Lys(Fmoc)-OMe (ZL0170)
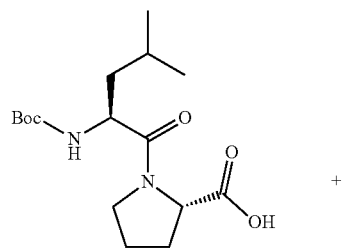
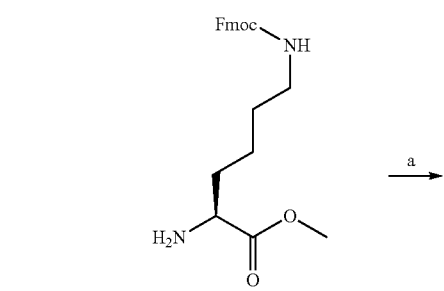
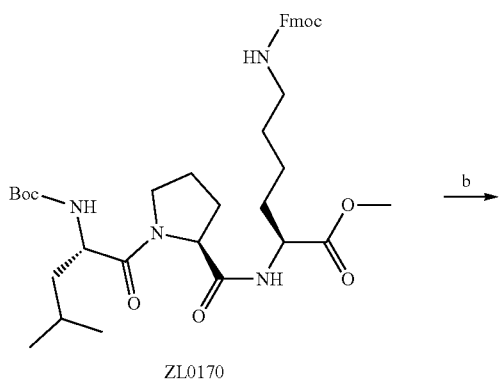
ZL0170
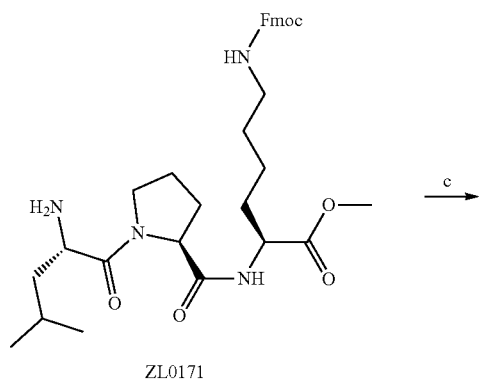
ZL0171
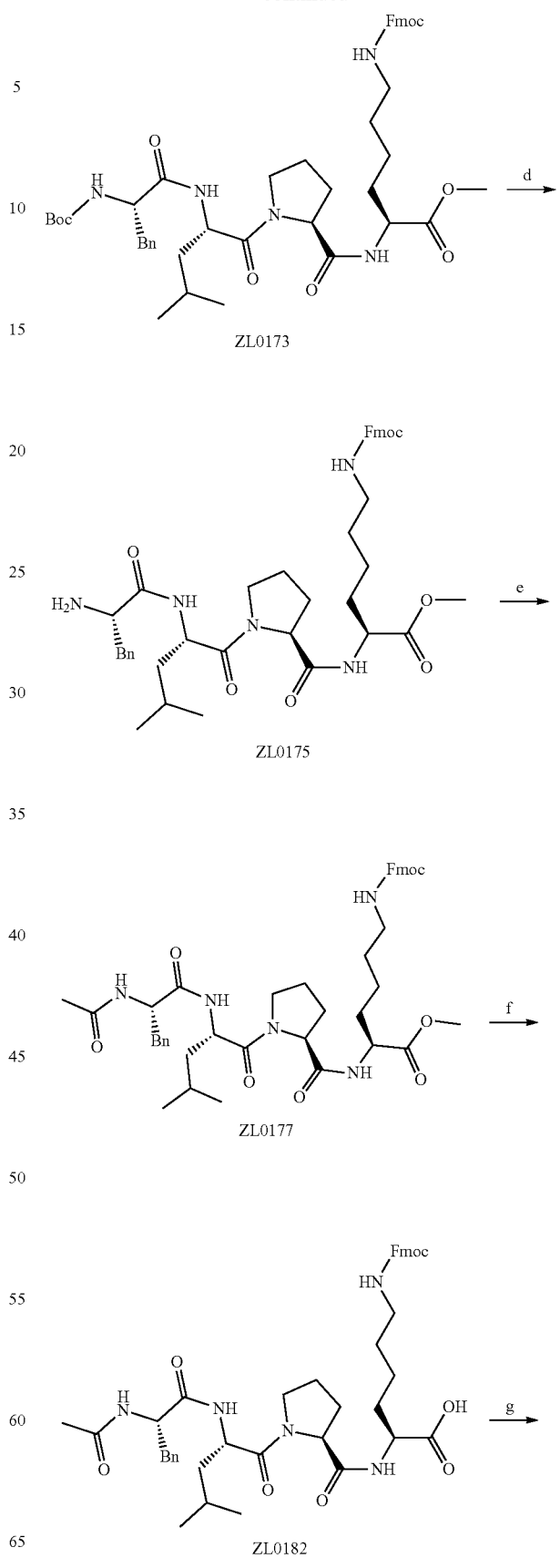

47
-continued

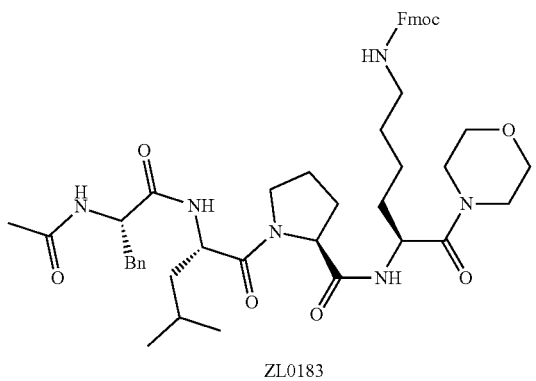

ZL0183

Reagents and conditions:
a HBTU, HOBt, DIEA, DCM, rt, quant.;
b TFA, DCM, rt, 87%;
c (tert-butoxycarbonyl)-L-phenylalanine, HBTU, HOBt, DIEA, DCM, rt, 81%;
d TFA, DCM, rt, quant.;
e CH₃COCl, Et₃N, DCM, rt, 91%;
f LiOH·H₂O, CH₃OH/H₂O, rt, 91%.
g morpholine, HBTU, HOBt, DIEA, DCM, rt, quant.

To a solution of Boc-Leu-Pro-OH (755 mg, 2.3 mmol) and Lys(Boc)-OMe (964 mg, 2.3 mmol) in 5 mL DCM, HBTU (2615 mg, 6.9 mmol), HOBt (310 mg. 2.3 mmol) and DIEA (1483 mg, 11.5 mmol) were added. The mixture was stirred at rt. for 18 hrs. The mixture was washed with 1N NaHSO₄, saturated NaHCO₃ and brine. After drying over anhydrous Na₂SO₄, the solution was concentrated and purified with silica gel column (Hexane/EtOAc=20/1 to 10/1) to obtain ZL0170 (1.6 g, quant.) as a colorless oil. $^1$H NMR (300 MHz, CDCl3) δ 7.77 (d, J=7.5 Hz, 2H), 7.62 (d, J=7.3 Hz, 2H), 7.40 (t, J=7.4 Hz, 2H), 7.32 (d, J=7.4 Hz, 2H), 7.03 (d, J=7.6 Hz, 1H), 5.80 (s, 1H), 5.32 (d, J=9.0 Hz, 1H), 4.50 (m, 5H), 4.28 (t, J=7.0 Hz, 1H), 3.80 (m, 1H), 3.74 (s, 3H), 3.60 (m, 1H), 3.30-3.06 (m, 2H), 2.21 (m, 2H), 2.06-1.42 (m, 13H), 1.30 (s, 9H), 0.97 (dd, J=11.8, 6.6 Hz, 6H). $^{13}$C NMR (75 MHz, CDCl₃) δ 173.15, 172.57, 171.02, 156.56, 155.62, 144.07, 141.30, 127.62, 127.00, 125.16, 119.91, 79.59, 77.27, 66.65, 60.07, 52.37, 52.00, 50.29, 47.31, 42.21, 40.28, 31.58, 28.96, 27.84, 25.17, 24.59, 23.36, 21.91, 21.81. ESI-MS (M+H)⁺ m/z 693.4. HR ESI-MS (M+H)⁺ m/z=693.3857 (calcd for C₃₈H₅₃N₄O₈: 693.3863).

H-Leu-Pro-Lys(Fmoc)-OMe (ZL0171)

To a solution of Boc-Leu-Pro-Lys(Fmoc)-OMe (2.3 mmol) in 4 mL DCM, 1.0 mL TFA was added. The mixture was allowed to stir at rt. for 2 hrs. Then the solution was concentrated to get the crude product ZL0171 (1.47 g, 87%) as a white foam. $^1$H NMR (300 MHz, CDCl₃) δ 7.78 (d, J=7.4 Hz, 2H), 7.59 (d, J=6.8 Hz, 2H), 7.40 (t, J=7.4 Hz, 2H), 7.33 (t, J=6.9 Hz, 2H), 7.15 (d, J=8.7 Hz, 1H), 6.53 (s, 1H), 4.72-4.08 (m, 6H), 3.78-3.61 (m, 4H), 3.55-3.40 (m, 1H), 3.15 (s, 2H), 2.21-1.24 (m, 13H), 0.93 (t, J=6.8 Hz, 6H). $^{13}$C NMR (75 MHz, CDCl₃) δ 172.65, 171.16, 169.16, 157.91, 156.74, 143.94, 141.29, 127.76, 127.08, 125.04, 120.00, 77.27, 67.47, 60.74, 52.32, 51.15, 50.46, 47.72, 47.11, 40.94, 39.79, 31.58, 29.31, 27.85, 25.08, 23.86, 22.99, 21.87. ESI-MS (M+Na)⁺ m/z 615.3. HR ESI-MS (M+Na)⁺ m/z=615.3164 (calcd for C₃₃H₄₄N₄O₆Na: 615.3159).

48
Ac-Leu-Pro-Lys(Fmoc)-OMe (ZL0172)

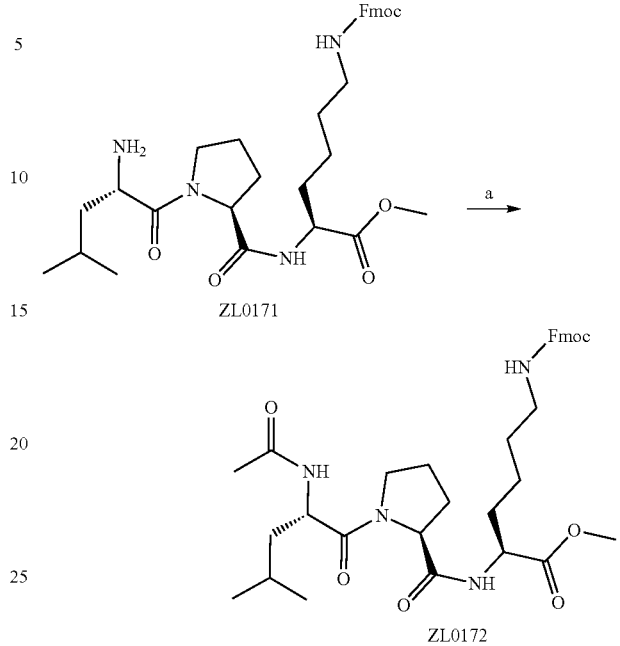

Reagents and conditions:
a CH₃COCl, Et₃N, DCM, rt, 81%.

To a solution of ZL0171 (150 mg, 0.253 mmol) and Et₃N (128 mg, 1.265 mmol) in 5 mL DCM, CH₃COCl (60 mg, 0.759 mmol) was added at 0° C. The solution was allowed to stir at rt. for overnight. The solution was washed with 1N NaHSO₄, saturated NaHCO₃ and brine. After drying over anhydrous Na₂SO₄, the solution was concentrated and purified with silica gel column (CHCl₃/CH₃OH=50/1 to 20/1) to obtain ZL0172 (130 mg, 81%) as a colorless oil. $^1$H NMR (300 MHz, CDCl₃) δ 8.40 (d, J=8.6 Hz, 0.53H), 7.78 (d, J=7.5 Hz, 2H), 7.60 (d, J=7.2 Hz, 2H), 7.41 (t, J=7.4 Hz, 2H), 7.33 (t, J=7.3 Hz, 2H), 7.03 (d, J=7.8 Hz, 0.33H), 6.87 (s, 0.56H), 6.67 (d, J=8.2 Hz, 0.57H), 6.44 (d, J=8.5 Hz, 0.35H), 5.61 (s, 0.35H), 4.91-4.76 (m, 1H), 4.67-4.22 (m, 5H), 3.92 (m, 1H), 3.76 (s, 3H), 3.65-3.55 (m, 1H), 3.35-3.10 (m, 2H), 2.27-1.93 (m, 7H), 1.76-1.31 (m, 8H), 1.02-0.86 (m, 6H).

We claim:
1. A compound of Formula I or a pharmaceutically acceptable salt thereof, wherein:

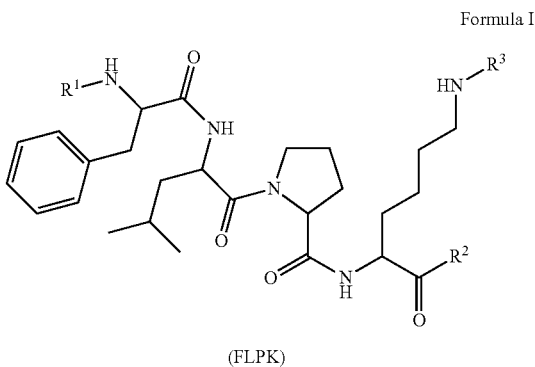

Formula I (FLPK)

R¹ and R³ are independently selected from H, alkyl, arylalklyl, —(C=O)R⁴, —(C=O)OR⁵, or Fmoc
  where R⁴ is alkyl, arylalkyl, or aryl;
  where R⁵ is alkyl, arylalkyl, or aryl;
R² is H, —OH, alkoxy, or —NR⁶R⁷;
  where R⁶ and R⁷ are independently selected from H, alkyl, aryl, or heteroaryl; or
  R⁶ and R⁷ are optionally joined to form a N-containing heterocycle with 1-4 heteroatoms; and
wherein if R² is OH, then R¹ and R³ are not both hydrogen.

2. The compound of claim 1, wherein R¹ is —(C=O)R⁴, wherein R⁴ is methyl.

3. The compound of claim 1, wherein R¹ is —(C=O)OR⁵ and R⁵ is benzyl; or R¹ is —(C=O)R⁴ and R⁴ is phenyl.

4. The compound of claim 1, wherein R³ is H; or —(C=O)OR⁵, wherein is R⁵ is t-butyl; or Fmoc.

5. The compound of claim 1, wherein R² is —NR⁶R⁷.

6. The compound of claim 1, wherein R² is methoxy.

7. The compound of claim 1, wherein the compound is one of:

ZL0173

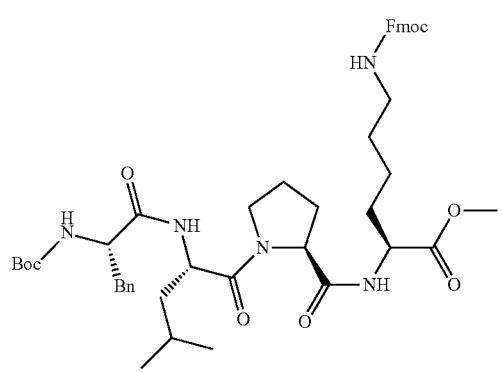

ZL0175

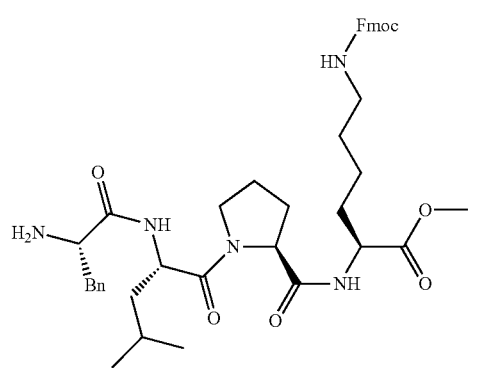

ZL0177

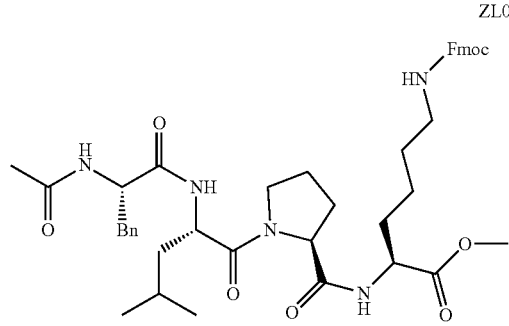

ZL0182

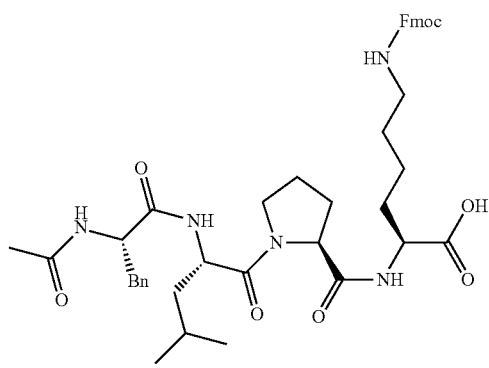

ZL0183

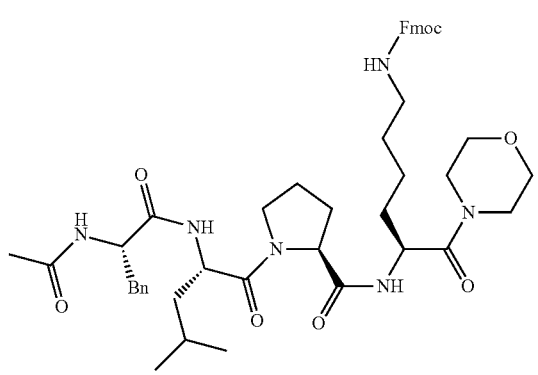

ZL0184

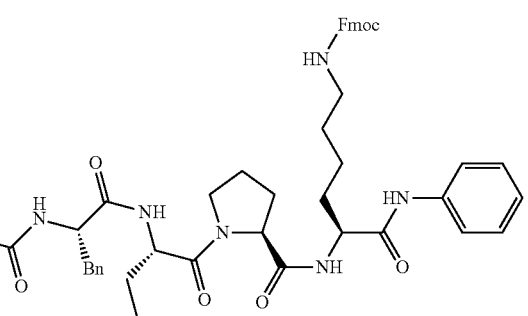

ZL0185

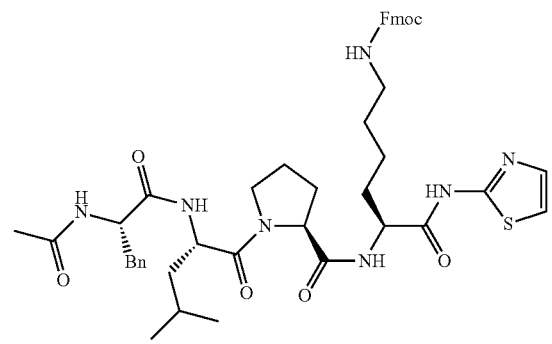

-continued

ZL0181

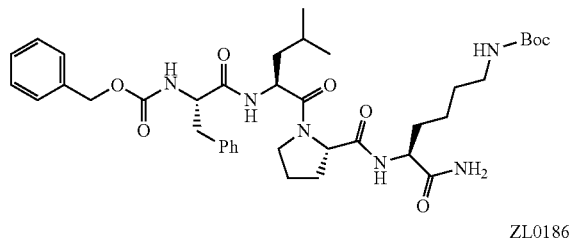

ZL0186

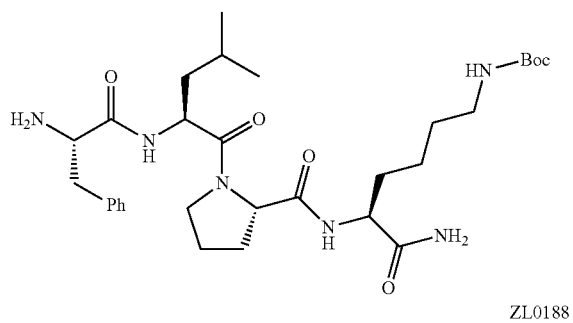

ZL0188

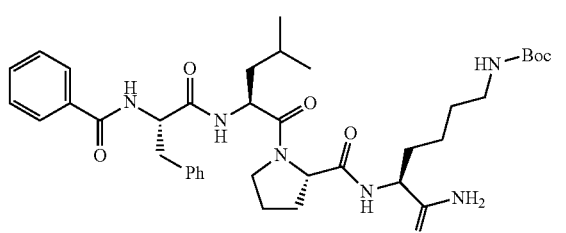

ZL0192

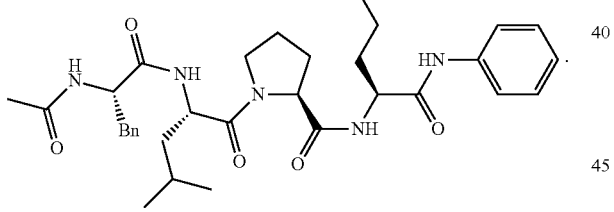

8. A compound of Formula IV or a pharmaceutically acceptable salt thereof, wherein:

Formula IV

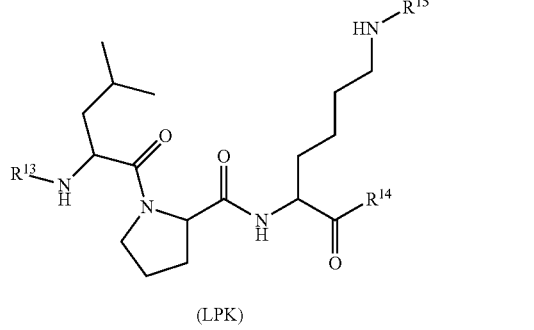

(LPK)

$R^{13}$ and $R^{15}$ are independently selected from H, alkyl, arylalklyl, —(CO)$R^4$, —(CO)O$R^5$, or Fmoc, where $R^4$ is alkyl, arylalkyl, or aryl, where $R^5$ is alkyl, arylalkyl, or aryl;

$R^{14}$ is H, —OH, alkoxy, or —N$R^6R^7$, where $R^6$ and $R^7$ are independently selected from H, alkyl, aryl, or heteroaryl; or $R^6$ and $R^7$ are optionally joined to form a N-containing heterocycle with 1-4 heteroatoms; and wherein if $R^{14}$ is OH, then $R^{13}$ and $R^{15}$ are not both hydrogen.

9. The compound of claim 8, wherein $R^{13}$ is H, —(CO)$R^4$, or —(CO)O$R^5$.

10. The compound of claim 9, wherein $R^{13}$ is acetyl or Boc.

11. The compound of claim 8, wherein $R^{14}$ is —NH2 or methoxy.

12. The compound of claim 8, wherein $R^{15}$ is H, Boc, or Fmoc.

13. The compound of claim 8, wherein the compound is one of:

ZL0143

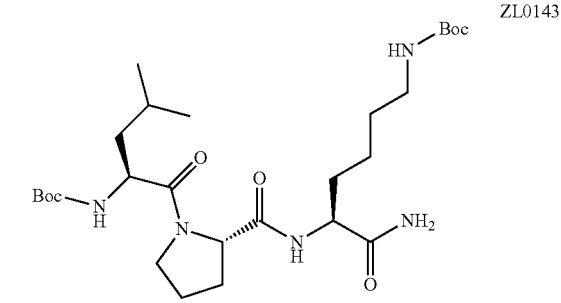

ZL0170

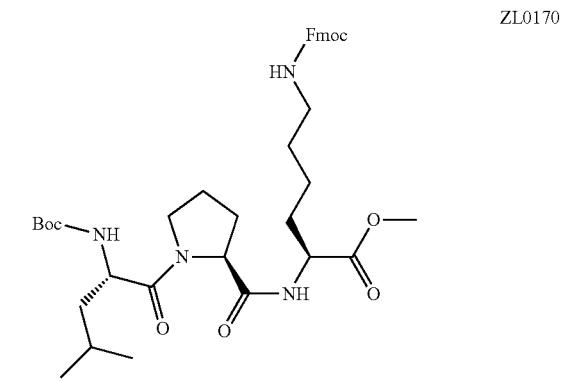

ZL0147

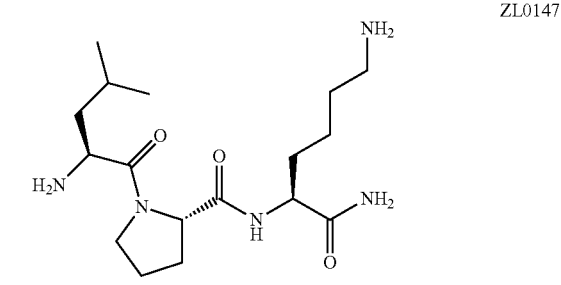

-continued

ZL0171

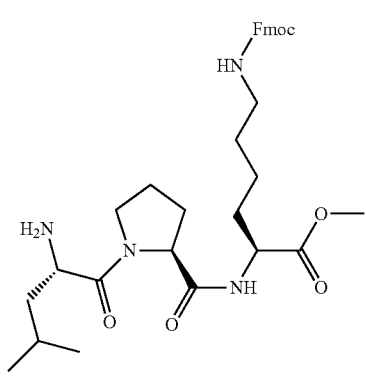

ZL0172

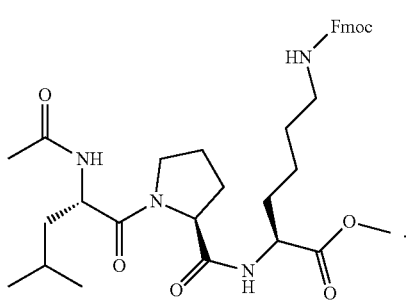

14. A method of inhibiting one or more Nav1.6 Channels, comprising contacting one or more cells with one or more compounds of Formulas I and/or IV:

Formula I (FLPK)

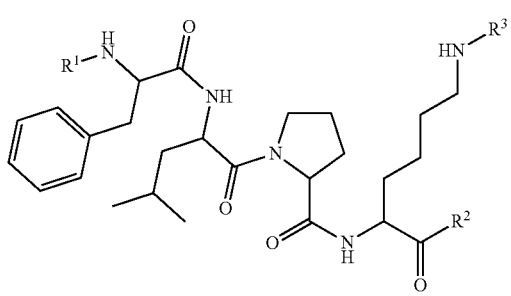

wherein $R^1$ and $R^3$ are independently selected from H, alkyl, arylalklyl, —(C=O)$R^4$, —(C=O)O$R^5$, or Fmoc where $R^4$ is alkyl, arylalkyl, or aryl;

where $R^5$ is alkyl, arylalkyl, or aryl;

$R^2$ is H, —OH, alkoxy, or —N$R^6R^7$;

where $R^6$ and $R^7$ are independently selected from H, alkyl, aryl, or heteroaryl; or $R^6$ and $R^7$ are optionally joined to form a N-containing heterocycle with 1-4 heteroatoms; and wherein if $R^2$ is OH, then $R^1$ and $R^3$ are not both hydrogen;

Formula IV (LPK)

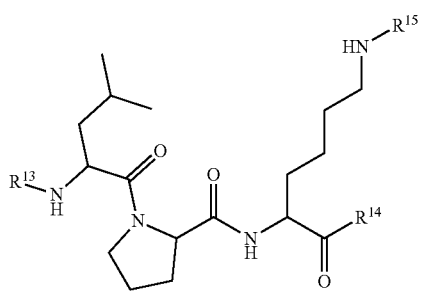

wherein $R^{13}$ and $R^{15}$ are independently selected from H, alkyl, arylalklyl, —(CO)$R^4$, —(CO)O$R^5$, or Fmoc, where $R^4$ is alkyl, arylalkyl, or aryl, where $R^5$ is alkyl, arylalkyl, or aryl;

$R^{14}$ is H, —OH, alkoxy, or —N$R^6R^7$, where $R^6$ and $R^7$ are independently selected from H, alkyl, aryl, or heteroaryl; or $R^6$ and $R^7$ are optionally joined to form a N-containing heterocycle with 1-4 heteroatoms; and wherein if $R^{14}$ is OH, then $R^{13}$ and $R^{15}$ are not both hydrogen.

15. The method of claim 14, further comprising inhibiting said Nav1.6 Channel in presence of one or more accessory proteins.

16. The method of claim 15, wherein said accessory protein is FGF13 and/or FGF14.

* * * * *